US007417133B2

(12) United States Patent
Jestin et al.

(10) Patent No.: US 7,417,133 B2
(45) Date of Patent: Aug. 26, 2008

(54) **METHODS FOR OBTAINING THERMOSTABLE ENZYMES, DNA POLYMERASE I VARIANTS FROM *THERMUS AQUATICUS* HAVING NEW CATALYTIC ACTIVITIES, METHODS FOR OBTAINING THE SAME, AND APPLICATIONS OF THE SAME**

(75) Inventors: Jean-Luc Jestin, Paris (FR); Sophie Vichier-Guerre, La Celle Saint Cloud (FR)

(73) Assignee: Institut Pasteur, Paris (FR)

( * ) Notice: Subject to any disclaimer, the term of this patent is extended or adjusted under 35 U.S.C. 154(b) by 406 days.

(21) Appl. No.: 10/787,219

(22) Filed: Feb. 27, 2004

(65) Prior Publication Data

US 2005/0191635 A1    Sep. 1, 2005

(51) Int. Cl.
    *C07H 21/04*    (2006.01)
(52) U.S. Cl. .................................... 536/23.2
(58) Field of Classification Search ................ 536/23.1, 536/23.2
    See application file for complete search history.

(56) References Cited

U.S. PATENT DOCUMENTS

| 5,618,711 | A   | 4/1997  | Gelfand et al. |
| 6,495,673 | B1  | 12/2002 | Neri et al. |
| 6,627,424 | B1* | 9/2003  | Wang .......................... 435/194 |
| 6,632,645 | B1  | 10/2003 | Gu et al. |
| 2005/0191635 | A1 | 9/2005 | Jestin et al. |

FOREIGN PATENT DOCUMENTS

EP    1 152 062    7/2001

OTHER PUBLICATIONS

Li et al. PNAS, vol. 96, pp. 6491-9496, Aug. 1999.*
U.S. Appl. No. 10/590,810, filed Aug. 25, 2006, Jestin, et al.
Gang Xia, et al., "Directed evolution of novel polymerase activities: Mutation f a DNA polymerase into an efficient RNA polymerase", PNAS, May 14, 2002, vol. 99, No. 10, pp. 6597-6602.
B. Villbrandt, et al., "Investigations on the thermostability and function of truncated *Thermus aquaticus* DNA polymerase fragments", Protein Engineering, vol. 10, No. 11, pp. 1281-1288, 1997.
Frances C. Lawyer, et al., "Isolation, Characterization, and Expression in *Escherichia coli* of the DNA Polymerase Gene from *Thermus aquaticus*", The Journal of Biological Chemistry, vol. 264, No. 11, Issue of Apr. 15, 1989, pp. 6427-6437.
Heike Strobe, et al., "Efficient Display of Two Enzymes on Filamentous Phage Using an Improved Signal Sequence", Molecular Biotechnology, vol. 24, No. 1, May 2003.
Sophie Vichier-Guerre, et al., "Iterative Cycles of In Vitro Protein Selection for DNA Polymerase Activity", Biocatalysis and Biotransformation, 2003, vol. 21 (2). pp. 75-78.

* cited by examiner

*Primary Examiner*—Gary Benzion
*Assistant Examiner*—Cynthia Wilder
(74) *Attorney, Agent, or Firm*—Oblon, Spivak, McClelland, Maier & Neustadt, P.C.

(57) ABSTRACT

The present invention provides a method for obtaining thermostable enzymes. The present invention also provides variants of DNA polymerase I from *Thermus aquaticus*. The present invention further provides methods of identifying mutant DNA polymerases having enhanced catalytic activity. The present invention also provides polynucleotides, expression systems, and host cells encoding the mutant DNA polymerases. Still further, the present invention provides a method to carry out reverse transcriptase-polymerase chain reaction (RT-PCR) and kits to facilitate the same.

17 Claims, 3 Drawing Sheets a b c d e f g    h i j k l m n r q p o n m l k j i h g f e d c b a

METHODS FOR OBTAINING THERMOSTABLE ENZYMES, DNA POLYMERASE I VARIANTS FROM *THERMUS AQUATICUS* HAVING NEW CATALYTIC ACTIVITIES, METHODS FOR OBTAINING THE SAME, AND APPLICATIONS OF THE SAME

CROSS-REFERENCE TO RELATED APPLICATIONS

Not Applicable.

BACKGROUND OF THE INVENTION

1. Field of the Invention

The present invention provides a method for obtaining thermostable enzymes. The present invention also provides variants of DNA polymerase I from *Thermus aquaticus*. The present invention further provides methods of identifying mutant DNA polymerases having enhanced catalytic activity. The present invention also provides polynucleotides, expression systems, and host cells encoding the mutant DNA polymerases. Still further, the present invention provides a method to carry out reverse transcriptase-polymerase chain reaction (RT-PCR) and kits to facilitate the same.

2. Discussion of the Background

Filamentous phage display is commonly used as a method to establish a link between a protein expressed as a fusion with a phage coat protein and its corresponding gene located within the phage particle (Marks et al., *J. Biol. Chem.* (1992) 267, 16007-16010). The use of filamentous phage particles as a chemical reagent provides further a strategy to create a complex between an enzyme, its gene and a substrate (Jestin et al., *Angew. Chem. Int. Ed.* (1999) 38, 1124-1127). This substrate can be cross-linked on the surface of filamentous phage using the nucleophilic properties of coat proteins. If the enzyme is active, conversion of the substrate to the product yields a phage particle cross-linked with the product, which can be captured by affinity chromatography (see discussion in Vichier-Guerre & Jestin, *Biocat. & Biotransf.* (2003) 21, 75-78).

Several similar approaches based on product formation for the isolation of genes encoding enzymes using phage display have been described in the literature for various enzymes (Fastrez et al., (2002) In: Brackmann, S. and Johnsson, K. eds., *Directed Molecular Evolution of Proteins* (Wiley VCH, Weinheim), pp 79-110). These in vitro selections of proteins for catalytic activity are well suited for use with large repertoires of about $10^8$ proteins or more. Several libraries of enzyme variants on phage have been constructed and catalytically active proteins with wild type like activities have been isolated (Atwell & Wells (1999) *Proc. Natl. Acad. Sci. USA* 96, 9497-9502; Heinis et al. (2001) *Prot. Eng.* 14, 1043-1052; Ponsard et al. (2001) *Chembiochem.* 2, 253-259; Ting et al. (2001) *Biopol.* 60, 220-228.). Mutants with different substrate specificities have been also obtained (Xia et al. (2002) *Proc. Natl. Acad. Sci. USA* 99, 6597-6602.). In these studies, the fraction of active variants in the libraries can be large and it remains unclear how rare an enzyme can be in the initial protein library so as to be selected after iterative selection cycles. Accordingly, there remains a critical need for an efficient process for making and identifying thermostable enzymes possessing a desired catalytic activity.

Reverse transcriptases are enzymes that are present generally in certain animal viruses (i.e., retroviruses), which are used in vitro to make complementary DNA (cDNA) from an mRNA template. Practically, reverse transcriptases have engendered significant interest for their use in reverse transcriptase-polymerase chain reaction (RT-PCR). As such, these proteins lend themselves to be a model system for development of an efficient method of making thermostable enzymes having a desired activity.

RNA generally contains secondary structures and complex tertiary sections, accordingly it is highly desired that the RNA be copied in its entirety by reverse transcription to ensure that integrity of cDNA is maintained with high accuracy. However, due to the often complicated secondary and tertiary structures of RNA, the denaturation temperatures are generally about 90° C. and, as such, the reverse transcriptase must be capable of withstanding these extreme conditions while maintaining catalytic efficiency.

The classically utilized enzymes for RT-PCR have been isolated from the AMV (Avian myeloblastosis virus) or MMLV (Moloney murine leukemia virus); however, these enzymes suffer from a critical limitation in that they are not thermostable. In fact, the maximum temperature tolerated by most commercially available reverse transcriptases is about 70° C.

One common approach to overcome this limitation in the existing technology with the previously described polymerases has been the use of a protein chaperones in addition to the polymerase. However, this method leads to problems associated with environmental compatibility metal ion requirements, multi-stage procedures, and overall inconvenience. Accordingly, an alternative strategy has been to use thermostable reverse transcriptases. This approach makes it possible to perform multiple denaturation and reverse transcription cycles using only a single enzyme.

To this end, the DNA-dependent DNA polymerase I of *Thermus aquaticus* (i.e., Taq polymerase), is thermostable and has reverse transcriptase activity only in the presence of manganese. However, when the manganese ion concentration is maintained in the millimolar range the fidelity of the enzyme is affected. It has been suggested that the thermostable DNA-dependent DNA polymerase of *Bacillus stearothermophilus* has reverse transcriptase activity, even in absence of magnesium, but in this case it is necessary to add a thermostable DNA polymerase for the PCR.

Therefore, there remains a critical need for high efficiency, thermostable enzymes that are capable of catalyzing reverse transcription and subsequent DNA polymerization in "one-pot" RT-PCR. Accordingly, the present invention provides an isolated population of thermostable reverse transcriptases, which are active in absence of manganese, by directed evolution of the Stoffel fragment of the Taq polymerase.

SUMMARY OF THE INVENTION

It is an object of the present invention to provide a method of identifying thermostable mutant polypeptides having a catalytic activity by:

a) packaging a vector in which a gene or fragment thereof encoding variants of a catalytic domain responsible for the catalytic activity fused to a gene encoding a phage coat protein, b) isolation and purification of phage particles;

c) heating the phage-mutant polypeptide at a temperature ranging from 50° C. to 90° C. for a time ranging from less than 1 minute to several hours d) cross-linking a specific substrate with a phage particle e) forming a reaction product from the substrate catalyzed by the thermostable mutant protein on phage, wherein the temperature is optionally regulated to be the same or greater or lower than the temperature of (c)

f) selecting the phage particles comprising a variant nucleotidic sequence encoding for the catalytic domain responsible for the catalytic activity at the regulated temperature, by capturing the reaction product or screening for said reaction product, g) infecting *E. coli* with the phage particles selected at step (f), h) incubating the infected *E. coli;* and i) assessing catalytic activity of the proteins corresponding to isolated genes.

It is an object of the present invention to provide a thermostable mutant DNA polymerase having at least 80% homology to the Stoffel fragment (SEQ ID NO: 26) of DNA polymerase I obtained from *Thermus aquaticus*.

To this end, the present invention provides thermostable polypeptides having at least 80% homology to SEQ ID NO: 26, wherein said polypeptide has at least one mutation selected from the group consisting of a mutation in amino acids 461 to 490 of SEQ ID NO: 26 (corresponding to amino acids 738 to 767 of the Taq polymerase wild-type sequence), A331T, S335N, M470K (position 747 of the Taq polymerase wild-type sequence), M470R (position 747 of the Taq polymerase wild-type sequence), F472Y (position 749 of the Taq polymerase wild-type sequence), M484V (position 761 of the Taq polymerase wild-type sequence), M484T (position 761 of the Taq polymerase wild-type sequence), and W550R (position 827 of the Taq polymerase wild-type sequence), and wherein said polypeptide has improved DNA polymerase activity and retains 5'-3' exonuclease activity. In an object of the present invention, the 3'-5' exonuclease activity of the mutant polypeptide is inactive.

In an object of the present invention, the thermostable mutant DNA polymerase also has a mutation at one or more position selected from A331, L332, D333, Y334, and S335 of SEQ ID NO: 26 (positions 608-612 of the Taq polymerase wild-type sequence).

In a particular object of the present invention, the mutant DNA polymerase has one of the following sequences: SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

Further, in another object of the present invention are polynucleotides that encode for the aforementioned thermostable mutant DNA polymerases.

In yet another object of the present invention is a kit for DNA amplification, which contains: (a) one or more of the aforementioned thermostable mutant DNA polymerases; (b) a concentrated buffer solution, wherein when said concentrated buffer is admixed with the isolated polypeptide the overall buffer concentration is 1×; (c) one or more divalent metal ion (e.g., $Mg^{2+}$ or $Mn^{2+}$); and (d) deoxyribonucleotides.

In yet another object of the present invention is a method of reverse transcribing an RNA by utilizing the inventive thermostable mutant DNA polymerases.

In still a further object of the present invention is a phage-display method for identifying thermostable mutant DNA polymerases in which the Stoffel fragment has been mutated, while the DNA polymerase activity and 5'-3' exonuclease activity has been maintained and/or enhanced.

The above objects highlight certain aspects of the invention. Additional objects, aspects and embodiments of the invention are found in the following detailed description of the invention.

BRIEF DESCRIPTION OF THE FIGURES

A more complete appreciation of the invention and many of the attendant advantages thereof will be readily obtained as the same becomes better understood by reference to the following Figures in conjunction with the detailed description below.

Figure 1:
FIG. 1 shows the reverse transcriptase activity of phage-polymerases assessed as obtained after different rounds of selection in the presence of $Mg^{2+}$ or $Mn^{2+}$ ions. The lane labels correspond to the following.
Figure 1:

| $MnCl_2$ | $MgCl_2$ |
|---|---|
| a: phage-polymerases of round 6 | h: phage-polymerases of round 6 |
| b: phage-polymerases of round 5 | i: phage-polymerases of round 5 |
| c: phage-polymerases of round 4 | j: phage-polymerases of round 4 |
| d: phage-polymerases of round 3 | k: phage-polymerases of round 3 |
| e: phage-polymerases of round 2 | l: phage-polymerases of round 2 |
| f: phage-polymerases of round 1 | m: phage-polymerases of round 1 |
| g: phage-polymerases of initial population | n: phage-polymerases of initial population |

Figure 2:
Figure 2:
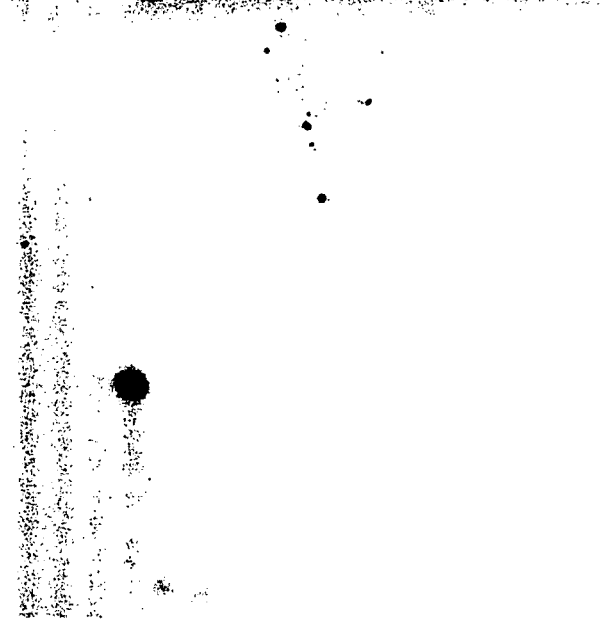

FIG. 2 shows the reverse transcriptase activity of phage-polymerases assessed as obtained after different rounds of selection in the presence of $Mg^{2+}$ ions. The lane designations in FIG. 2 are as follows:

| Phage-polymerase heated at 65° C. for 5 min. | Phage-polymerase not preheated |
|---|---|
| a: phage-polymerases of initial population | h: phage-polymerases of initial population |
| b: phage-polymerases of round 1 | i: phage-polymerases of round 1 |
| c: phage-polymerases of round 2 | j: phage-polymerases of round 2 |
| d: phage-polymerases of round 3 | k: phage-polymerases of round 3 |
| e: phage-polymerases of round 4 | l: phage-polymerases of round 4 |
| f: phage-polymerases of round 5 | m: phage-polymerases of round 5 |
| g: phage-polymerases of round 6 | n: phage-polymerases of round 6 |
| | o: control AMV-RT, 1 U |
| | p: control AMV-RT, 0.1 U |
| | q: control AMV-RT, 0.01 U |
| | r: control AMV-RT, 0.001 U |

Figure 3:
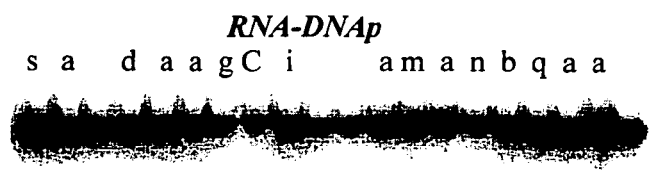
Figure 3:
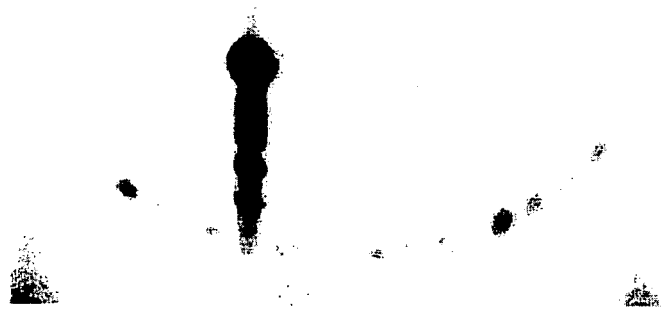

FIG. 3 shows the reverse transcriptase activity of various monoclonal phage-polymerases obtained after round 6 in the presence of $Mg^{2+}$ ions. The lane designations in FIG. 3 are as follows: s=SEQ ID NO: 38; a=SEQ ID NO: 20; d=SEQ ID NO: 24; g=SEQ ID NO: 28; C=AMV-RT; i=SEQ ID NO: 30; m=SEQ ID NO: 32; n=SEQ ID NO: 34; b=SEQ ID NO: 22; and q=SEQ ID NO: 36.

Figure 4:
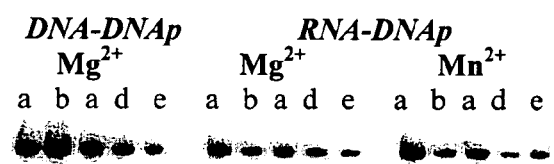
Figure 4:
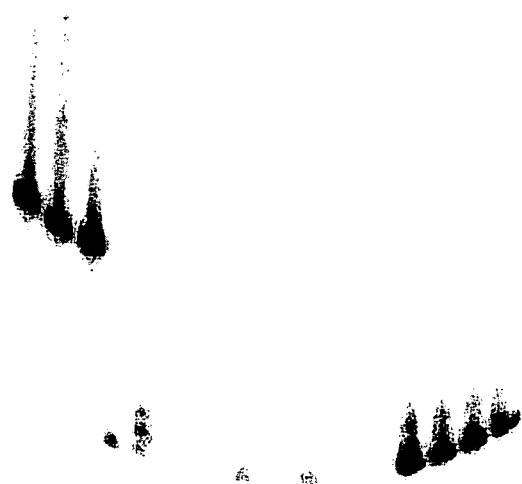

FIG. 4 shows the reverse transcriptase activities and the polymerase activities of monoclonal phage-polymerases obtained after the round 6 in the presence of $Mg^{2+}$ or $Mn^{2+}$ ions. The lane designations in FIG. 4 are as follows: a=SEQ ID NO: 20; b=SEQ ID NO: 22; d=SEQ ID NO: 24; and e=SEQ ID NO: 26.

Figure 5:
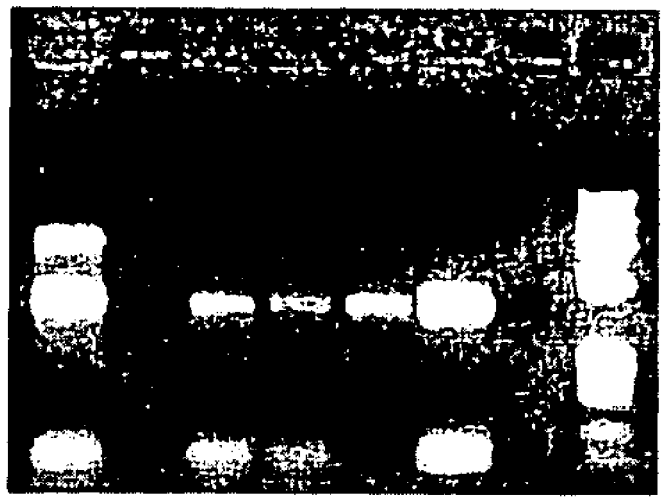

FIG. 5 shows purified mutant RT-polymerases a, b, and d used in polymerase chain reaction. The lanes in the gel appearing in FIG. 5 include the three clones corresponding on clones a, b and d on FIG. 4. In addition, the positive control was performed using the Stoffel fragment polymerase e and commercially Taq polymerase (Promega). The lanes in FIG. 5 are as follows:

lane 1: Taq
lane 2: a=SEQ ID NO: 20
lane 3: b=SEQ ID NO: 22 lane 4: d=SEQ ID NO: 24
lane 5: e=SEQ ID NO: 26
lane 6: Molecular weight marker

Figure 6:
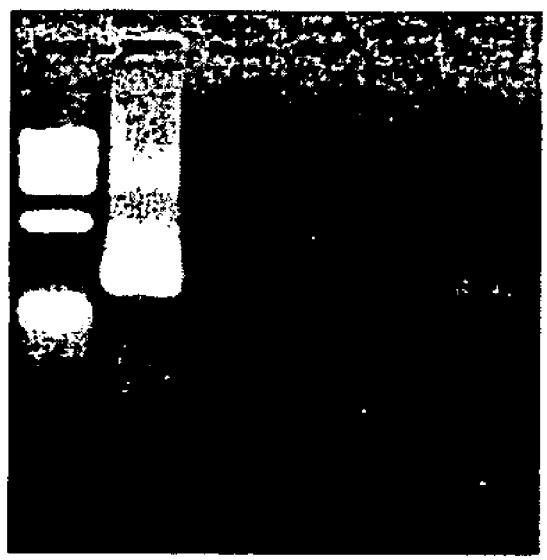

FIG. 6 shows purified mutant RT-polymerases a, b, and d used in RT-polymerase chain reaction. The lanes in the gel appearing in FIG. 6 include the three clones corresponding to clones a, b and d on FIG. 4. In addition, the positive control was performed using the Stoffel fragment polymerase e and the phage-polymerase of AMV-RT (Promega). The lanes in FIG. 6 are as follows:
lane 1: molecular weight marker
lane 2: control AMV-RT
lane 3: b=SEQ ID NO: 22
lane 4: a=SEQ ID NO: 20
lane 5: e=SEQ ID NO: 26
lane 6: d=SEQ ID NO: 24

DETAILED DESCRIPTION OF THE INVENTION

Unless specifically defined, all technical and scientific terms used herein have the same meaning as commonly understood by a skilled artisan in enzymology, biochemistry, cellular biology, molecular biology, and the medical sciences.

All methods and materials similar or equivalent to those described herein can be used in the practice or testing of the present invention, with suitable methods and materials being described herein. All publications, patent applications, patents, and other references mentioned herein are incorporated by reference in their entirety. In case of conflict, the present specification, including definitions, will control. Further, the materials, methods, and examples are illustrative only and are not intended to be limiting, unless otherwise specified.

The present invention provides a method of identifying thermostable mutant polypeptides having a catalytic activity comprising:

a) packaging a vector in which a gene or fragment thereof encoding variants of a catalytic domain responsible for the catalytic activity fused to a gene encoding a phage coat protein, b) isolation and purification of phage particles;

c) heating the phage-mutant polypeptide at a temperature ranging from 50° C. to 90° C., preferably from 55° C. to 65° C., more preferably at 65° C. for a time ranging from 30 seconds to several hours, preferably from 1 minute to 3 hours, more preferably from 5 minutes to 2 hours, most preferably 10 minutes to 1 hour d) cross-linking a specific substrate with a phage particle e) forming a reaction product from the substrate catalyzed by the thermostable mutant polypeptide on phage, wherein the temperature is optionally regulated to be the same or greater or lower than the temperature of (c) (i.e., from 25° C. to 70° C., preferably from 37° C. to 70° C. and more preferably at 65° C.).

f) selecting the phage particles comprising a variant nucleotidic sequence encoding for the catalytic domain responsible for the catalytic activity at the regulated temperature, by capturing the reaction product or screening for said reaction product, g) infecting E. coli with phage particles selected at (f)

h) incubating the infected E. coli; and i) assessing catalytic activity of the proteins corresponding to isolated genes.

In the embodiment above, the gene or fragment thereof encoding variants of a catalytic domain may be directly or indirectly fused to the gene encoding a phage coat protein. When the gene or fragment thereof encoding variants of a catalytic domain and the gene encoding a phage coat protein are indirectly fused it is preferred that the fusion be through a peptide or polypeptide linker.

Within this above-recited embodiment, steps (a) to (h) may be repeated 0 to 20 times, preferably 1 to 15 times, more preferably 2 to 10 times, most preferably 3 to 7 times The method comprising a single cycle (repeated 0 times) is particularly adapted to high throughput screening, when steps are repeated from 3 to 7 times, the method is better adapted for classical empirical screening.

The peptide utilized within this embodiment is selected from the group consisting of:

a flexible linker such as a glycine rich linker such as $(SG_4)n$ (SEQ ID NO: 39), Human calmodulin (SEQ ID NO: 46, the DNA encoding SEQ ID NO:46 is SEQ ID NO:56), and Hexahistidine binding single chain variable fragment (Grütter M. G., *J. Mol. Biol.* 2002, 318, 135-147.) consisting of (i) Anti-His Tag Antibody 3D5 Variable Heavy Chain (SEQ ID NO: 47)

(ii) Linker (SEQ ID NO: 48)

(iii) Anti-His Tag Antibody 3D5 Variable Light Chain (SEQ ID NO: 49).

Moreover, the polypeptide linker is selected from the group consisting of: any protein binding the substrate at high temperature, any catalytic domain such as exonuclease 5' to 3' (from *Thermus thermophilus*, SEQ ID NO: 50), or 3' to 5'(from *E. coli*, SEQ ID NO: 51), Catalytic domain of *Bacillus circulans* cyclodextringlycosyltransferase (SEQ ID NO: 52, the DNA is in SEQ ID NO:57), Catalytic domain of *Bordetella pertussis* adenylate cyclase(SEQ ID NO: 53—the DNA is in SEQ ID NO:58), *Bacillus amyloliquefaciens* serine protease subtilisin (SEQ ID NO: 54—the DNA is in SEQ ID NO:59), and Catalytic domain of *Bacillus subtilis* lipase A (SEQ ID NO: 55, Quax W. J. 2003, 101, 19-28 *J. Biotechnol.*).

As used in the present invention, the cross-linking between the specific substrate of the catalytic domain of the polypeptide with the phage particle is made by a cross-linking agent selected from the group consisting of a: maleimidyl group, iodoacetyl group, disulfide derivative and any other thermostable link (conducting to a stable protein-protein interaction or protein-molecule interaction).

In a preferred embodiment, the catalytic domain may be the catalytic domain of an enzyme selected from the group consisting of: a polymerase, an alpha-amylase (substrate such as starch), a lipase (substrate such as ester), a protease (modified or not modified peptide or polypeptide as substrate), a cyclodextringlycosyltransferase, and an adenylate cyclase.

In another embodiment, the assessment of the catalytic activity of step (f) is made by means of a DNA polymerization.

In yet another embodiment of the present invention, step (b) may be performed after (e) of cross-linking or during (h) of assessing catalytic activity.

As a general method for the isolation of thermostable enzymes and their genes the following should be noted:

First, the gene encoding variants of a catalytic domain are fused to the gene encoding a phage coat protein (such as filamentous phage g3, g6, g7, g9 or g8 protein or of other phage/virus particles) either directly or using a peptide or polypeptide linker such as a short peptide sequence or a protein or a protein domain. These genes encoding phage coat proteins may be fused either at the 3' or at the 5' terminus depending on whether the N- or the C-termini of the proteins are located on the outside of the particle.

This is done either using a phage vector or a phagemid vector used with a helper phage.

Second, the phage-variant enzymes may be heated at a preferred temperature of 65° C. for 1 minute or for several hours as appropriate. This step can be performed before or after the substrate cross-linking (maleimidyl group derivatised substrate (DNA primer) crosslinked to the phage particle) and catalysis (DNA polymerisation) steps. Catalysis is preferably at 65° C. for 2 minutes, but can be done at any temperature between 0° C. and 100° C. Crosslinking is typically performed for 2 hours at 37° C., but can be done at other temperatures (higher temperature may increase maleimidyl hydrolysis versus maleimidyl phage cross-linking).

It is worth noting that the link between the gene and the corresponding enzyme variants is unaltered by high temperatures and the phage particle are still infective and the genes selected can be amplified by *E. coli* after infection (cf. for example, Kristensen P, Winter G. Proteolytic selection for protein folding using filamentous bacteriophages. Fold Des. 1998;3(5):321-8)

By way of example of the aforementioned embodiments, the present invention relates to a purified, thermostable DNA polymerase purified from *Thermus aquaticus* and recombinant means for producing the enzyme. Thermostable DNA polymerases are useful in many recombinant DNA techniques, especially nucleic acid amplification by the polymerase chain reaction (PCR)

Directed protein-evolution strategies generally make use of a link between a protein and the encoding DNA. In phage-display technology, this link is provided by fusion of the protein with a coat-protein that is incorporated into the phage particle containing the DNA. Optimization of this link can be achieved by adjusting the signal sequence of the fusion.

Linking of a gene to its corresponding polypeptide is a central step in directed protein evolution toward new functions. Filamentous bacteriophage particles have been extensively used to establish this linkage between a gene of interest and its protein expressed as a fusion product with a phage coat protein for incorporation into the phage particle. Libraries of proteins displayed on phage can be subjected to in vitro selection to isolate proteins with desired properties together with their genes.

Creating a link between a gene and a single corresponding protein was achieved by making use of a phagemid for expression of the fusion protein and of a helper phage for assembly of the phage particles. This approach, yielding a monovalent display of protein, was found to be essential to avoid avidity effects or chelate effects, which introduce strong biases during in vitro selections for affinity. However, it also produces phage particles that do not display any protein of interest and which thereby represent a background in evolution experiments.

To optimize the link between a gene and a single corresponding protein, several methods have been used. For example, the periplasmic factor Skp was found to improve the display of single-chain Fv antibodies on filamentous phage (Bothmann, H. and Plückthun, A. (1998) Selection for a periplasmic factor improving phage display and functional periplasmic expression. Nat. Biotech. 16, 376-380.). In a previous study, the present inventors showed that specific signal sequences for optimal display on phage of the Taq DNA polymerase I Stoffel fragment can be isolated from a library of more than $10^7$ signal sequences derived from pelB (Jestin, J. L., Volioti, G. and Winter, G. (2001). Improving the display of proteins on filamentous phage. Res. Microbiol. 152, 187-191). Signal sequences, once translated, are recognized by the bacterial protein export machinery. The polypeptide is then exported in the bacterial periplasm before cleavage of the signal peptide by the signal peptidase, thereby releasing the mature protein.

A short sequence, m (SG$_4$CG$_4$; SEQ ID NO: 39), at the C-terminus of the signal sequence, was initially introduced as a potential cross-linking site of substrates on phage that may be useful for selections by catalytic activity. This glycine-rich sequence may also be important for preventing structure formation at the peptidase cleavage site or for defining two independently folding units in the pre-protein. The glycine-rich sequence may then improve the signal sequence processing and finally lead to a greater ratio of protein fusions on phage. The present inventors, therefore, evaluated the effect of a selected signal sequence on the display of proteins on phage, as well as the effect of the m sequence at the C-terminus of the signal peptide.

In an embodiment of the present invention is a method of identifying thermostable mutant polymerases derived from the Stoffel fragment of Taq comprising a) packaging a vector in which a polynucleotide encoding a phage coat protein is fused to a polynucleotide encoding a protein having at least 80% identity to SEQ ID NO: 26 into a phage b) expressing the fusion protein;

c) isolation (selection) of phage particles;

d) infecting *E. coli* and incubating the infected *E. coli*;

e) detecting the fusion protein;

f) assessing polymerase activity.

In this method, evolutionarily advantageous mutants may be identified by repeating steps (b)-(f) 0 to 25 times, preferably 0-20 times, more preferably 1-15 times, a most preferably 2 to 10 times. The method comprising one cycle (repeated 0 times) is particularly adapted to high throughput screening, when steps are repeated from 3 to 7 times, the method is better adapted for classical emprirical screening.

In a preferred embodiment, the phage coat protein has a sequence of SEQ ID NO: 39.

By way of example, Applicants provide the following exemplary discussion of the phage-display method of the present invention and refer to Strobel et al, Molec. Biotech. 2003, vol. 24, pp. 1-9, which is incorporated herein by reference in its entirety:

The amino acid signal sequences are:

| | | |
|---|---|---|
| pelB: | MKYLLPTAAAGLLLLAAQPAMA; | (SEQ ID NO: 41) |
| 17: | MKTLLAMVLVGLLLLPPGPSMA; | (SEQ ID NO: 42) |
| 110: and | MRGLLAMLVAGLLLLPIAPAMA; | (SEQ ID NO: 43) |
| 112: | MRRLLVIAAGLLLLLAPPTMA. | (SEQ ID NO: 44) |

The present inventors goal was to increase the display of proteins at the surface of filamentous phages. As model proteins, the present inventors chose the catalytic domains of adenylate cyclases from *E. coli* (ACE) and from *B. pertussis* (ACB). The present inventors also examined the display of two different enzymes, an adenylate cyclase and the Stoffel fragment of Taq DNA polymerase I, incorporated into phage particles as single polypeptide fusion products with minor coat protein p3. In this work, the present inventors evaluated the effects of two signal peptides (pelB and 17) and of the short peptide (m; SEQ ID NO: 39) at the N-terminus of the fusion of these enzymes with p3. One other construct, deriving from the selected signal peptide 112, is also mentioned here, and the data are summarized together with previously published data for the selected signal sequences 110 and 112 (2).

The phage particles were produced by using a helper phage, KM13 (6), for assembly of the particles, and by using phagemids pHEN1 (5), pHEN117, and pHEN1112 (2) encoding the p3 fusion proteins. These phagemid vectors differ in their signal sequence: pelB is from *Erwinia caratovora* pectate lyase B (7), whereas signal sequences 17, 110, and 112, were selected from a library of more than $10^7$ signal sequences for optimal display of the Stoffel fragment on filamentous phage (2). For all 17 phagemids encoding the different fusion proteins described in this work, the present inventors observed standard titers of infective particles, which were all in the range of $1.4 \times 10^{10}$-$7.8 \times 10^{10}$ phages/mL of culture medium. Furthermore, enzymatic activities were detected for all phage-cyclase particles by thin layer chromatography and by HPLC (data not shown).

The efficiency of protein display on phage was evaluated through two approaches. The first makes use of the engineered helper phage KM13 (6) to measure the fraction of infective phage particles that display a fusion product. The p3 fusion protein provided by the phagemid and the p3 protein provided by the helper phage compete for incorporation into the phage particles. The helper phage p3 is engineered so as to contain a protease cleavage site between domains 2 and 3 of p3. In phage particles that contain only helper p3 copies, no full p3 copy is available for bacterial infection after protease treatment: the phage particles are noninfective. If a phage particle has incorporated a p3 fusion protein, one copy of the three-p3 domains remains after protease cleavage, and is sufficient for infection of *E. coli*. The trypsin-resistant fraction of phage is therefore a measure of protein display on infective phages. With this method, the display of fusion proteins was found to vary over more than two orders of magnitude for each cyclase, depending on the signal sequence and on neighboring sequences. Among the phagemid vectors containing the selected signal sequence 17, three of the four fusion proteins that the present inventors studied (AC-p3 and AC-Stoffel-p3, where AC is the adenylate cyclase catalytic domain of *E. coli* or *B. pertussis*) were remarkably well incorporated into phage particles: more than one phage particle out of ten displayed an enzyme. No more than one particle in 300 displayed the *E. coli* cyclase fused to the Stoffel fragment and to protein 3, and better display of this protein could not be found among the constructs tested.

The peptide m, $SG_4CG_4$, at the N-terminus of the mature fusion protein, was found to increase the display of *B. pertussis* cyclase-polymerase fusion on phage, by 100-fold for signal sequence 17 and by 10-fold for pelB. For this fusion, the worst display ratios are significantly improved with peptide m. Display of *B. pertussis* cyclase on phage was high in all cases, such that a marginal improvement due to the m peptide was found for signal sequence 17, and improvement within the limits of experimental error for pelB. Concerning the *E. coli* cyclase protein, peptide m decreases the latter's display by a factor of 30 to 40. For the *E. coli* cyclase-polymerase fusion, peptide m showed no significant effect with the signal sequence pelB and a small improvement with signal sequence 17.

Significant effects of the signal sequence on phage display were detected for three of the four fusions in the present inventors' study: from 5- to about 20-fold improvements in display on phage were noted for substitution of pelB by signal sequence 17. In the case of the *B. pertussis* cyclase-p3 fusion protein, incorporation of the fusion protein into phage particles was high, whether the signal sequence was pelB, 17, or 112. Indeed, for the selected signal sequence 112, up to 40% of infective phage particles displayed an enzyme at the surface of filamentous phage.

When two enzymes were simultaneously displayed on phage (either *E. coli* or *B. pertussis* adenylate cyclase and the Stoffel fragment polymerase), the present inventors noted that the incorporation of p3 fusion products was significantly reduced in most cases. Remarkably, about half of the infective phage particles displayed a *B. pertussis* adenylate Cyclase-Stoffel fragment polymerase-p3 protein fusion when the selected signal sequence 17 and the short N-terminal peptide m were present in the construct.

The second approach to estimating the level of fusion proteins incorporated into phage particles relies on the detection of p3 domain 3 by a monoclonal antibody (8) after SDS-PAGE and Western blotting of denatured phage particles. These results are in accordance with the data the present inventors obtained by measuring the trypsin-resistant fraction of infective phages. All fusion products expressed on phage and which correspond to a trypsin-resistant fraction of phage higher than 0.1 are indeed observed by Western blot analysis.

The present inventors aim to direct the evolution of adenylate cyclases by in vitro selection using a chemistry involving filamentous phage. This should provide a tool for the engineering of adenylate cyclases as well as a strategy for the functional cloning of this class of enzymes. Recent in vitro selection methods for catalytic activity using phage display have been designed as affinity chromatography methods for the reaction product linked to the phage enzyme that catalyzed the reaction from substrate to product. These selection methods were established with enzymes such as nuclease (9), DNA polymerase (10), peptidase (11,12), peptide ligase (13), and beta-lactamase (14). They require an efficient display of enzyme on phage and a method to link the substrate/product to phage-enzymes.

In the work reported here, the present inventors investigated the display of adenylate cyclases from *B. pertussis* and from *E. coli* on filamentous phage, and the display of two independent enzymes, an adenylate cyclase and the Taq DNA polymerase I Stoffel fragment. The Stoffel fragment (15) could be used as a tool to establish an in vitro selection for cyclase activity as follows: the polymerase domain may serve as an anchor of the substrate ATP on phage through double-stranded DNA used as a linker with a high affinity for the fusion protein. Another approach to cross-linking substrate and phage involves introduction of the thiol group of a cysteine residue within peptide m ($SG_4CG_4$), at the N-terminus of the mature fusion protein and at the C-terminus of the fusion protein's signal sequence (10).

The signal sequences 17, 110, and 112, used in the present inventors' study had been selected from large libraries of pelB mutants for optimal display of the Stoffel fragment-p3 protein fused to the peptide m (2). It was therefore important to further investigate which sequence context was essential for selection of these signal sequences, either the short peptide m or the entire gene. Interestingly, the present inventors found that the presence or the absence of this short peptide, $SG_4CG_4$, can yield up to 100-fold increases in the display of a fusion protein on filamentous phage. This strong effect was observed for the *B. pertussis* cyclase-Stoffel-p3 fusion as well as for the *E. coli* cyclase-p3 fusion in the case of the signal sequence 17 (Table 2). Of further note is that the signal sequences 17 and 112, yield generally better levels of protein display on phage than does pelB (FIG. 3). This improved display of proteins might be ascribed to the different targeting modes of the signal sequences. These selected signal sequences that improve the display of proteins on phage should therefore be useful in other systems.

Our study highlights the important effects of the signal sequence and of a short peptide at the C-terminus of the signal sequence on the display of proteins on phage. Apart from the previously stated conclusions that the selected signal sequence 17 often yields an improved display as compared with pelB, and that sequence m can have drastic effects on the level of protein display, the set of protein fusions described here is not sufficient to define any further rules about sequences and optimal display of proteins on phage. Indeed, incorporation of a fusion protein into a phage particle is the result of a complex sequence of events involving fusion gene transcription and translation, folding, and export of the fusion protein, as well as cleavage of the signal sequence.

Two approaches, however, can be envisaged for efficient display of proteins on bacteriophage. First, directed signal peptide evolution experiments can be undertaken for any defined protein so as to isolate a signal sequence for optimal display on phage. This approach was described previously in the case of the Stoffel fragment of Taq DNA polymerase I (2). A more straightforward and quicker approach consists of the screening of several phagemid vectors that differ in their signal sequences and, more generally, in their regulatory sequences. In this report the present inventors have shown that for three of the four fusion proteins tested, excellent cyclase display levels can be obtained: more than one phage in ten displays an enzyme. Such display levels for large proteins should be useful for further approaches to directed protein evolution.

With use of the phagemid strategy, almost every particle expresses a p3 copy provided by the phagemid if no gene fusion has been engineered or if the insert from the gene fusion has been deleted. On the contrary, about one phage particle in a thousand incorporates large fusion proteins such as cyclase-Stoffel fragment-p3 fusions. This indicates that for an equal mixture of two genes, thousand-fold differences in expression of the corresponding proteins on phage particles can be obtained. This bias may be of no importance if enrichment factors per selection round are much larger than $10^3$, but it may otherwise significantly alter the outcome of evolution experiments. Similar protein expression levels on phage of different genes would be useful to minimize biases introduced by successive amplifications in evolution experiments. The use of sets of phagemid vectors that differ by their signal sequences and by neighboring sequences might be of interest for better representation of protein libraries on filamentous phage. Additionally, the display of two distinct enzymes on single phage particles might be useful to direct their coevolution, especially in the case of two enzymes involved in the same metabolic pathway with an unstable reaction intermediate.

By insertion or by deletion of the short peptide sequence $SG_4CG_4$ (m; SEQ ID NO: 39) at the C-terminus of the signal sequence, the present inventors have shown that two enzymes can be very efficiently expressed as single polypeptides on the surface of filamentous bacteriophage by using the phagemid strategy. The model proteins described in this study are the catalytic domains of adenylate cyclases of *B. pertussis* or of *E. coli*, fused or not fused to the Stoffel-fragment DNA polymerase.

On average, the present inventors found the best display levels for the selected signal sequence 17, which had been previously selected from a large library for optimal display on phage of the Stoffel fragment, and not for the commonly used signal sequence pelB. Yet the present inventors observed striking differences in display levels of these enzymes on the surfaces of phage particles, depending on the short N-terminal peptide m. The findings reported here should be useful for the display of large and of cytoplasmic proteins on filamentous phage particles, and more generally for protein engineering using phage display.

The term "thermostable" enzyme refers to an enzyme that is stable over a temperature range of approximately 55° C. to 105° C. In particular, thermostable enzymes in accordance with the present invention are heat resistant and catalyze the template directed DNA synthesis. Preferably, the activity of the thermostable enzymes of the present is at least 50% of activity, preferably at least 75%, more preferably at least 85%, of the wild-type enzyme activity over the same temperature range. In a particularly preferred embodiment, the thermostable enzyme of the present invention exhibits at least 50% of activity, preferably at least 75%, more preferably at least 85%, of the wild-type enzyme activity when said wild-type enzyme activity is measured under optimal conditions. Moreover, it is preferable that the "thermostable" enzyme does not become irreversibly denatured when subjected to the elevated temperatures and incubation time for denaturation of double-stranded nucleic acids, as well as the repetitive cycling between denaturation, annealing, and extension inherent to PCR-based techniques.

As used herein, the term "reduced" or "inhibited" means decreasing the activity of one or more enzymes either directly or indirectly. The definition of these terms also includes the reduction of the in vitro activity, either directly or indirectly, of one or more enzymes.

The term "enhanced" as used herein means increasing the activity or concentration one or more polypeptides, which are encoded by the corresponding DNA. Enhancement can be achieved with the aid of various manipulations of the bacterial cell, including mutation of the protein, replacement of the expression regulatory sequence, etc.

In order to achieve enhancement, particularly over-expression, the number of copies of the corresponding gene can be increased, a strong promoter can be "operably linked," or the promoter- and regulation region or the ribosome binding site which is situated upstream of the structural gene can be mutated. In this regard, the term "operably linked" refers to the positioning of the coding sequence such that a promoter, regulator, and/or control sequence will function to direct the expression of the protein encoded by the coding sequence located downstream therefrom.

Expression cassettes that are incorporated upstream of the structural gene act in the same manner. In addition, it is possible to increase expression by employing inducible promoters. A gene can also be used which encodes a corresponding enzyme with a high activity. Expression can also be improved by measures for extending the life of the mRNA. Furthermore, preventing the degradation of the enzyme increases activity as a whole. Moreover, these measures can optionally be combined in any desired manner. These and other methods for altering gene activity in a plant are known as described, for example, in Methods in Plant Molecular Biology, Maliga et al, Eds., Cold Spring Harbor Laboratory Press, New York (1995). The definition of these terms also includes the enhancement of the in vitro activity, either directly or indirectly, of one or more enzymes.

A gene (polynucleotide) can also be used which encodes a corresponding or variant polymerase having at least 80% identity to SEQ ID NO: 26. These gene (polynucleotides) can have various mutations. For example, a mutation of one or more amino acids in amino acids 461 to 490 of SEQ ID NO: 26. Further examples of mutations include mutations at positions M470, F472, M484, and W550 A331, and S335. In a preferred embodiment, these mutations are A331T, S335N, M470K, M470R, F472Y, M484V, M484T, and W550R. In a particularly preferred embodiment, the polynucleotides of the present invention encode polypeptides having one or more of the aforementioned mutations and share at least 85% identity, at least 90% identity, at least 95% identity, or at least 97.5% identity to the polypeptide of SEQ ID NO: 26. Moreover, polynucleotides of the present invention encode polypeptides that have DNA polymerase activity and/or 5'-3' exonuclease activity. More particularly, the polynucleotides of the present invention encode polypeptides that are capable of catalyzing the reverse transcription of mRNA.

In the present invention, the polynucleotide may encode a polypeptide contain at least one mutation at a position selected from the group consisting of A331, L332, D333, Y334, and S335. The polynucleotide may encode a polypeptide of the present invention which has amino acid sequence selected from the group consisting of SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

Within the context of the present application, the preferred polynucleotides possess a polynucleotide sequence selected from the group consisting of SEQ ID NO: 19, SEQ ID NO: 21, SEQ ID NO: 23, SEQ ID NO: 27, SEQ ID NO: 29, SEQ ID NO: 31, SEQ ID NO: 33, SEQ ID NO: 35, and SEQ ID NO: 37.

Within the scope of the present invention are also polynucleotides that are homologous to the aforementioned sequences. In the context of the present application, a polynucleotide sequence is "homologous" with the sequence according to the invention if at least 80%, preferably at least 90%, more preferably 95%, and most preferably 97.5% of its base composition and base sequence corresponds to the sequence according to the invention. It is to be understood that, as evinced by the Examples of the present invention and the phage-display method highlighted herein, screening of theoretical mutations within the scope of the present invention would require nothing more than a technician's level of skill in the art. More specifically, as is routine in the art, with the identification of a candidate sequence the artisan would assay and screen one or all possible permutations of the said sequence to identify mutants possessing the same or better DNA polymerase activity, reverse transcriptase activity, and/or 5'-3' exonuclease activity.

The expression "homologous amino acids" denotes those that have corresponding properties, particularly with regard to their charge, hydrophobic character, steric properties, etc.

Homology, sequence similarity or sequence identity of nucleotide or amino acid sequences may be determined conventionally by using known software or computer programs such as the BestFit or Gap pairwise comparison programs (GCG Wisconsin Package, Genetics Computer Group, 575 Science Drive, Madison, Wis. 53711). BestFit uses the local homology algorithm of Smith and Waterman, Advances in Applied Mathematics 2: 482-489 (1981), to find the best segment of identity or similarity between two sequences. Gap performs global alignments: all of one sequence with all of another similar sequence using the method of Needleman and Wunsch, J. Mol. Biol. 48:443-453 (1970). When using a sequence alignment program such as BestFit, to determine the degree of sequence homology, similarity or identity, the default setting may be used, or an appropriate scoring matrix may be selected to optimize identity, similarity or homology scores. Similarly, when using a program such as BestFit to determine sequence identity, similarity or homology between two different amino acid sequences, the default settings may be used, or an appropriate scoring matrix, such as blosum45 or blosum80, may be selected to optimize identity, similarity or homology scores.

The terms "isolated" or "purified" means separated from its natural environment.

The term "polynucleotide" refers in general to polyribonucleotides and polydeoxyribonucleotides, and can denote an unmodified RNA or DNA or a modified RNA or DNA.

The term "polypeptides" is to be understood to mean peptides or proteins that contain two or more amino acids that are bound via peptide bonds. A "polypeptide" as used herein is understood to mean a sequence of several amino acid residues linked by peptide bonds. Such amino acids are known in the art and encompass the unmodified and modified amino acids. In addition, one or more modifications known in the art such as glycosylation, phosphorylation, etc may modify the polypeptide.

The term "homologous" as used herein is understood to mean two or more proteins from the same species or from a different species. Within the meaning of this term, said two or more polypeptides share at least 80% identity to the polypeptide of SEQ ID NO: 26 and can have the mutations discussed herein. In a particularly preferred embodiment, the polypeptides of the present invention have one or more of the aforementioned mutations and share at least 85% identity, at least 90% identity, at least 95% identity, or at least 97.5% identity to the polypeptide of SEQ ID NO: 26. Moreover, the polypeptides of the present invention have DNA polymerase activity and/or 5'-3' exonuclease activity. More particularly, the polypeptides of the present invention are capable of catalyzing the reverse transcription of mRNA.

In the present invention, the polypeptide may contain one or more mutations, such as A331, L332, D333, Y334, and S335. The isolated polypeptide of the present invention has an amino acid sequence selected from the group consisting of SEQ ID NO: 20, SEQ ID NO: 22, SEQ ID NO: 24, SEQ ID NO: 28, SEQ ID NO: 30, SEQ ID NO: 32, SEQ ID NO: 34, SEQ ID NO: 36, and SEQ ID NO: 38.

In an embodiment of the present invention are mutations concerning alanine in position 331 (A331), and serine in position 335 (S335) that may have particular importance derived from the fact that they are surrounding the aspartic acid D in position 333 which is responsible for the chelation of $Mn^{2+}$ or $Mg^{2+}$. Thus, in one embodiment of the present invention, mutations of one or more amino acids 10 amino acids upstream and/or 10 amino acids downstream of this site are provided.

The expression "homologous amino acids" denotes those that have corresponding properties, particularly with regard to their charge, hydrophobic character, steric properties, etc.

Moreover, one skilled in the art is also aware of conservative amino acid replacements such as the replacement of glycine by alanine or of aspartic acid by glutamic acid in proteins as "sense mutations" which do not result in any fundamental change in the activity of the protein, i.e. which are functionally neutral. It is also known that changes at the N- and/or C-terminus of a protein do not substantially impair the function thereof, and may even stabilize said function. As such, these conservative amino acid replacements are also envisaged as being within the scope of the present invention.

The present invention also relates to DNA sequences that hybridize with the DNA sequence that encodes a corresponding or variant polymerase having at least 80% homology to SEQ ID NO: 26, the polypeptides having the mutations described herein. The present invention also relates to DNA sequences that are produced by polymerase chain reaction (PCR) using oligonucleotide primers that result from the DNA sequence that encodes a corresponding or variant polymerase having at least 80% homology to SEQ ID NO: 26, wherein the polypeptide has at least one mutation as described herein, or fragments thereof. Oligonucleotides of this type typically have a length of at least 15 nucleotides.

The terms "stringent conditions" or "stringent hybridization conditions" includes reference to conditions under which a polynucleotide will hybridize to its target sequence, to a detectably greater degree than other sequences (e.g., at least 2-fold over background). As used herein, stringent hybridization conditions are those conditions which allow hybridization between polynucleotides that are 80%, 85%, 90%, 95%, or 97.5% homologous as determined using conventional homology programs, an example of which is UWGCG sequence analysis program available from the University of Wisconsin. (Devereaux et al., Nucl. Acids Res. 12: 387-397 (1984)). Stringent conditions are sequence-dependent and will be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing).

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C.

Specificity is typically the function of post-hybridization washes, the critical factors being the ionic strength and temperature of the final wash solution. For DNA—DNA hybrids, the Tm can be approximated from the equation of Meinkoth and Wahl, Anal. Biochem., 138:267-284 (1984): Tm=81.5° C. +16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization and/or wash conditions can be adjusted to hybridize to sequences of the desired identity. For example, if sequences with approximately 90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution) it is preferred to increase the SSC concentration so that a higher temperature can be used. An extensive guide to the hybridization of nucleic acids is found in Current Protocols in Molecular Biology, Chapter 2, Ausubel, et al., Eds., Greene Publishing and Wiley-Interscience, New York (2000).

Thus, with the foregoing information, the skilled artisan can identify and isolated polynucleotides, which are substantially similar to the present polynucleotides. In isolating such a polynucleotide, the polynucleotide can be used as the present polynucleotide in, for example, to express a polypeptide having DNA polymerase activity and 5'-3' exonuclease activity.

One embodiment of the present invention is methods of screening for polynucleotides, which have substantial homology to the polynucleotides of the present invention, preferably those polynucleotides encoding a polypeptide having DNA polymerase activity and/or 5'-3' exonuclease activity.

The polynucleotide sequences of the present invention can be carried on one or more suitable plasmid vectors, as known in the art for bacteria or the like.

Host cells useful in the present invention include any cell having the capacity to be infected or transfected by phages or vectors comprising the polynucleotide sequences encoding the enzymes described herein and, preferably also express the thermostable enzymes as described herein. Suitable host cells for expression include prokaryotes, yeast, archae, and other eukaryotic cells. Appropriate cloning and expression vectors for use with bacterial, fungal, yeast, and mammalian cellular hosts are well known in the art, e.g., Pouwels et al. Cloning Vectors: A Laboratory Manual, Elsevier, N.Y. (1985). The vector may be a plasmid vector, a single or double-stranded phage vector, or a single or double-stranded RNA or DNA viral vector. Such vectors may be introduced into cells as polynucleotides, preferably DNA, by well known techniques for introducing DNA and RNA into cells. The vectors, in the case of phage and viral vectors also may be and preferably are introduced into cells as packaged or encapsulated virus by well known techniques for infection and transduction. Viral vectors may be replication competent or replication defective. In the latter case viral propagation generally will occur only in complementing host cells. Cell-free translation systems could also be employed to produce the enzymes using RNAs derived from the present DNA constructs.

Prokaryotes useful as host cells in the present invention include gram negative or gram positive organisms such as *E. coli* or *Bacilli*. In a prokaryotic host cell, a polypeptide may include a N-terminal methionine residue to facilitate expression of the recombinant polypeptide in the prokaryotic host cell. The N-terminal Met may be cleaved from the expressed recombinant polypeptide. Promoter sequences commonly used for recombinant prokaryotic host cell expression vectors include β-lactamase and the lactose promoter system.

Expression vectors for use in prokaryotic host cells generally comprise one or more phenotypic selectable marker genes. A phenotypic selectable marker gene is, for example, a gene encoding a protein that confers antibiotic resistance or that supplies an autotrophic requirement. Examples of useful expression vectors for prokaryotic host cells include those derived from commercially available plasmids such as the cloning vector pBR322 (ATCC 37017). pBR322 contains genes for ampicillin and tetracycline resistance and thus provides simple means for identifying transformed cells. To construct an expression vector using pBR322, an appropriate promoter and a DNA sequence are inserted into the pBR322 vector.

Other commercially available vectors include, for example, pKK223-3 (Pharmacia Fine Chemicals, Uppsala, Sweden) and pGEM1 (Promega Biotec, Madison, Wis., USA).

Promoter sequences commonly used for recombinant prokaryotic host cell expression vectors include β-lactamase (penicillinase), lactose promoter system (Chang et al., Nature 275:615, (1978); and Goeddel et al., Nature 281:544, (1979)), tryptophan (trp) promoter system (Goeddel et al., Nucl. Acids Res. 8:4057, (1980)), and tac promoter (Maniatis, Molecular Cloning: A Laboratory Manual, Cold Spring Harbor Laboratory, p. 412 (1982)).

Yeasts useful as host cells in the present invention include those from the genus *Saccharomyces, Pichia, K. Actinomycetes* and *Kluyveromyces.* Yeast vectors will often contain an origin of replication sequence from a 2μ yeast plasmid, an autonomously replicating sequence (ARS), a promoter region, sequences for polyadenylation, sequences for transcription termination, and a selectable marker gene. Suitable promoter sequences for yeast vectors include, among others, promoters for metallothionein, 3-phosphoglycerate kinase (Hitzeman et al., J. Biol. Chem. 255:2073, (1980)) or other glycolytic enzymes (Holland et al., Biochem. 17:4900, (1978)) such as enolase, glyceraldehyde-3-phosphate dehydrogenase, hexokinase, pyruvatee decarboxylase, phosphofructokinase, glucose-6-phosphate isomerase, 3-phosphoglycerate mutase, pyruvate kinase, triosephosphate isomerase, phosphoglucose isomerase, and glucokinase. Other suitable vectors and promoters for use in yeast expression are further described in Fleer et al., Gene, 107:285-195 (1991). Other suitable promoters and vectors for yeast and yeast transformation protocols are well known in the art.

Yeast transformation protocols are known to those of skill in the art. One such protocol is described by Hinnen et al., *Proceedings of the National Academy of Sciences USA,* 75:1929 (1978). The Hinnen protocol selects for Trp.sup.+ transformants in a selective medium, wherein the selective medium consists of 0.67% yeast nitrogen base, 0.5% casamino acids, 2% glucose, 10 μg/ml adenine, and 20 μg/ml uracil.

Mammalian or insect host cell culture systems well known in the art could also be employed to express recombinant polypeptides, e.g., Baculovirus systems for production of heterologous proteins in insect cells (Luckow and Summers, Bio/Technology 6:47 (1988)) or Chinese hamster ovary (CHO) cells for mammalian expression may be used. Transcriptional and translational control sequences for mammalian host cell expression vectors may be excised from viral genomes. Commonly used promoter sequences and enhancer sequences are derived from Polyoma virus, Adenovirus 2, Simian Virus 40 (SV40), and human cytomegalovirus. DNA sequences derived from the SV40 viral genome may be used to provide other genetic elements for expression of a structural gene sequence in a mammalian host cell, e.g., SV40 origin, early and late promoter, enhancer, splice, and polyadenylation sites. Viral early and late promoters are particularly useful because both are easily obtained from a viral genome as a fragment which may also contain a viral origin of replication. Exemplary expression vectors for use in mammalian host cells are well known in the art.

The enzymes of the present invention may, when beneficial, be expressed as a fusion protein that has the enzyme attached to a fusion segment. The fusion segment often aids in protein purification, e.g., by permitting the fusion protein to be isolated and purified by affinity chromatography. Fusion proteins can be produced by culturing a recombinant cell transformed with a fusion nucleic acid sequence that encodes a protein including the fusion segment attached to either the carboxyl and/or amino terminal end of the enzyme.

In one embodiment, it may be advantageous for propagating the polynucleotide to carry it in a bacterial or fungal strain with the appropriate vector suitable for the cell type. Common methods of propagating polynucleotides and producing proteins in these cell types are known in the art and are described, for example, in Maniatis et al., Molecular Cloning: A Laboratory Manual, Cold Spring Harbor Laboratory Press, New York (1982) and Sambrook et al., Molecular Cloning: A Laboratory Manual, Cold Spring Harbor Laboratory Press, New York (1989).

In one embodiment of the present invention are monoclonal phages:

1. SJL q deposited as CNCM I-3168 in the Collection Nationale de Cultures de Microorganismes (CNCM) on Feb. 27, 2004.

2. SJL d deposited as CNCM I-3169 in the Collection Nationale de Cultures de Microorganismes (CNCM) on Feb. 27, 2004.

3. SJL I deposited as CNCM I-3170 in the Collection Nationale de Cultures de Microorganismes (CNCM) on Feb. 27, 2004.

4. SJL s deposited as CNCM I-3171 in the Collection Nationale de Cultures de Microorganismes (CNCM) on Feb. 27, 2004.

5. SJL b deposited as CNCM I-3172 in the Collection Nationale de Cultures de Microorganismes (CNCM) on Feb. 27, 2004.

6. SJL n deposited as CNCM I-3173 in the Collection Nationale de Cultures de Microorganismes (CNCM) on Feb. 27, 2004.

7. SJL g deposited as CNCM I-3174 in the Collection Nationale de Cultures de Microorganismes (CNCM) on Feb. 27, 2004.

8. SJL m deposited as CNCM I-3175 in the Collection Nationale de Cultures de Microorganismes (CNCM) on Feb. 27, 2004.

9. SJL a deposited as CNCM I-3176 in the Collection Nationale de Cultures de Microorganismes (CNCM) on Feb. 27, 2004.

The phage strains I-3168 through I-3176 described above were deposited under the terms of the Budapest Treaty at CNCM on Feb. 27, 2004. The address of the CNCM (Collection Nationale De Cultures De Micro-organisms) is Institut Pasteur, 28, rue du Dr. Roux, 75724 Paris Cédex 15, France.

In an embodiment of the present invention is a kit for amplifying DNA containing:

an isolated thermostable polypeptide, wherein said polypeptide has at least 80% homology to SEQ ID NO: 26, wherein said polypeptide has at least one mutation at a position selected from the group consisting of M470, F472, M484, and W550, more preferably selected from the group consisting of M470K, M470R, F472Y, M484V, M484T, and W550R, and wherein said polypeptide has DNA polymerase activity and 5'-3' exonuclease activity;

a concentrated buffer solution, wherein when said concentrated buffer is admixed with the isolated polypeptide the overall buffer concentration is 1×;

one or more divalent metal ions; and
deoxyribonucleotides.

In this embodiment, the preferred divalent metal ion is $Mg^{2+}$ or $Mn^{2+}$. In this connection, the concentration of the divalent metal ion ranges from 0.1 to 5 mM, preferably from 1 to 3 mM, more preferably from 2 to 2.5 mM. However, if the reaction is performed in a phosphate buffer, a buffer containing EDTA, or a buffer containing any other magnesium chelator, the concentration of magnesium may be increased to up to 100 mM.

For the kit of the present invention the isolated thermostable polypeptide may be in a form selected from the group consisting of a lyophilized form, a solution form in a suitable buffer or carrier, and a frozen form in a suitable buffer or carrier.

The kit of the present invention may also include a 5' to 3' exonuclease and/or a 3' to 5' exonuclease. A preferred 5' to 3' exonuclease has a sequence as in SEQ ID NO: 50 (the DNA is in SEQ ID NO:60) and the 3' to 5' exonuclease as in SEQ ID NO: 51 (the DNA is in SEQ ID NO:61).

With respect to the suitable buffer or carrier, the following components may be used: Tris-HCl, KCl, Triton-X100, dimethylsulfoxide, tetramethyl ammonium chloride, etc.

In the present invention, the concentrated buffer solution corresponds to a stock solution that has a concentration ranging from 1.5× to 10×, where the concentration is measured in relation to the final reaction concentration (1×). To this end, the buffer solution (1×) contains the following components: 10 mM Tris-HCl, pH at 25° C. of 9, 50 mM KCl, 0.1% Triton-X100.

For the kit according to the present invention, the stock concentration of the deoxyribonucleotides ranges from 50 µM to 200 mM, preferably from 75 µM to 150 mM, more preferably 100 µM to 100 mM, for each dNTP. Moreover, the concentration of each dNTP in the PCR reaction according to the present invention should range from 10 µM to 500 µM, preferably from 25 µM to 400 µM, more preferably 50 µM to 300 µM. As used in the present invention, the term "deoxyribonucleotides" includes: dATP, dCTP, dGTP, and dTTP. It is to be understood that within the scope of the present invention, the kit may include in place of or in addition to the aforementioned components, RNA precursors, minor ("rare") bases, and/or labelled bases.

In another embodiment of the present invention is a method of amplifying DNA from a culture and/or purified stock solution of DNA and/or mRNA by utilizing a thermostable polypeptide according to the present invention. To this end, protocols for conducting PCR and RT-PCR would be readily appreciated by the skilled artisan. However, for sake of completeness, the artisan is directed to the following exemplary references for protocols for conducting PCR and RT-PCR (See, for example, Rougeon, F, et al. (1975) *Nucl. Acids Res.*, 2, 2365-2378; Rougeon, F, et al. (1976) *Proc. Natl. Acad. Sci. USA*, 73, 3418-3422; Grabko, V. I., et al. (1996) *FEBS Letters*, 387, 189-192; and Perler, F., et al. (1996) *Adv. Prot. Chem.*, 48, 377-435)

With reference to reverse transcribing an RNA, a preferred method includes:

a) providing a reverse transcription reaction mixture comprising said RNA, a primer, a divalent cation, and an isolated thermostable polypeptide comprising an amino acid sequence having at least 80% homology to SEQ ID NO: 26, wherein said polypeptide has at least one mutation at a position selected from the group consisting of M470, F472, M484, and W550, more preferably selected from the group consisting of M470K, M470R, F472Y, M484V, M484T, and W550R, and wherein said polypeptide has DNA polymerase activity and 5'-3' exonuclease activity in a suitable buffer; and b) treating said reaction mixture at a temperature and under conditions suitable for said isolated polypeptide to initiate synthesis of an extension product of said primer to provide a cDNA molecule complementary to said RNA.

It is to be understood that the skilled artisan would appreciate that the thermal cycling should be optimized to account for variations in the enzyme selected, the template to be reverse transcribed, the primers to be used to facilitate amplification (i.e., with respect to the melting and annealing temperatures), and the relative concentrations to be used for each of the reaction components. Such optimization is well within the purview of the skilled artisan; however, exemplary protocols may include the following:

TABLE 2

PCR protocols

|  | a | b | c | d | e | # of repeated Cycles |
|---|---|---|---|---|---|---|
| PCR 1 | 94° C., 3' | 94° C., 1' | 66° C., 1' | 72° C., 2' | 72° C., 15' | b-d = 30 |
| PCR 2 | 94° C., 3' | 94° C., 1' | 62° C., 1' | 72° C., 2' | 72° C., 15' | b-d = 30 |
| PCR 3 | 94° C., 3' | 94° C., 30" | 59° C., 30" | 72° C., 1' | 72° C., 15' | b-d = 30 |
| PCR 4 | 94° C., 3' | 94° C., 30" | 68° C., 1.5' | 68° C., 6' |  | b-c = 35 |
| PCR 5 | 94° C., 1' | 94° C., 30" | 70° C., 30" | 72° C., 1' | 72° C., 15' | b-d = 25 |
| PCR 6 | 94° C., 3' | 94° C., 30" | 59° C., 30" | 72° C., 1' | 72° C., 15' | b-d = 35 |
| PCR 7 | 94° C., 3' | 94° C., 1' | 58° C., 1' | 72° C., 2' | 72° C., 15' | b-d = 35 |

Moreover, it is to be understood that contemplated in the present invention is that with the polypeptide of the present invention the skilled artisan would appreciate that the buffer components and buffer concentrations should also be optimized. To this end, in a preferred embodiment, the kit of the present invention may be utilized.

As used above, the phrases "selected from the group consisting of," "chosen from," and the like include mixtures of the specified materials.

In one embodiment of a method of obtaining a thermostable variant enzyme is provided. This method comprises the following:

a) screening enzymes expressed at the surface of phage particles and identifying at least a thermostable variant conserving its active;

catalytic domain at regulated temperature according to the method of identifying thermostable mutant polypeptides having a catalytic activity as described herein, b) isolating and sequencing a DNA encoding said identified thermostable variant;

c) preparing a vector comprising the DNA of step (b);

d) transfecting or infecting cells with the vector obtained at step c);

e) expressing the thermostable variant enzyme from the cells and optionally, f) recovering, isolating and purifying said thermostable variant enzyme expressed at step (e).

Where a numerical limit or range is stated herein, the endpoints are included. Also, all values and subranges within a numerical limit or range are specifically included as if explicitly written out.

Having generally described this invention, a further understanding can be obtained by reference to certain specific examples, which are provided herein for purposes of illustration only, and are not intended to be limiting unless otherwise specified.

EXAMPLES

Materials and Methods

Buffers

Buffer A (1x):

50 mM Tris-HCl at pH 8.3 at 25° C., 50 mM KCl, 10 mM $MgCl_2$, 0.5 mM spermidine, 10 mM dithiothreitol Buffer B (1x):

20 mM Tris-HCl at pH 8.8 at 25° C., 10 mM KCl, 10 mM $(NH_4)_2SO_4$, 2 mM $MgSO_4$, 0.1% Triton X-100, 0.1 g/l BSA Buffer C (1x):

10 mM Tris-HCl at pH 9.0 at 25° C., 50 mM KCl, 1.5 mM $MgCl_2$, 0.1% Triton X-100

Synthesis of Substrates for Selection

Deoxyoligonucleotides were prepared by solid phase synthesis on a DNA synthesizer (EXPEDITE™, Millipore). The 5'-maleimidyl derivatized primer TAA CAC GAC AAA GCG CAA GAT GTG GCG T (SEQ ID NO: 13) was synthesized as described previously (Jestin J. L., Kristensen P., Winter G., A method for the selection of catalysis using phage display and proximity coupling. Angew. Chem. Int. Ed. 1999, 38, 8, 1124-1127) purified on a C18 reverse phase HPLC column, and characterized by electrospray mass spectroscopy 8998.4/8999.9 (measured/calculated). 5-[-N—[N—(N-biotinyl-ε-aminocaproyl)-γ-aminobutyryl]-3-aminoallyl]-2'deoxy-uridine-5'-triphosphate (biotin-dUTP) was purchased from Sigma and the other deoxynucleotide triphosphates dATP, dCTP and dGTP were obtained from Roche-Boehringer.

Library Construction

Three phagemids libraries were mixed for phage preparation. The first two libraries (I: FseI/NotI and II: PstI/NheI) derive from mutagenic PCR amplification of the wild-type Taq gene in the presence of manganese [I: reference(Fromant, Blanquet, Plateau, Anal. Biochem., 224, 347-353, 1995) with $MnCl_2$: 0.5 mM; II: reference (Cadwell, Joyce, PCR methods and amplifications, Mutagenic PCR, 3, S136-S140) with four distinct $MnCl_2$ concentrations (0.5, 0.35, 0.25 and 0.125 mM)] using following primers (I) SEQ ID NO: 1 and SEQ ID NO: 2, PCR 1, or (II) SEQ ID NO: 3 and SEQ ID NO: 4, PCR 2 (for primers: see Table 1, and for cycle settings: see Table 2).

The third phagemids library (III) was constructed by oligonucleotide assembly using the wild-type Taq gene. First, four PCR fragments were prepared using Taq polymerase (PCR 3, see Table 2), the wild-type Stoffel fragment gene as template and the following primer pairs (5-6), (7-8), (9-10) and (11-2) in buffer C 1X (for primers: see Table 1).

After purification with the QIAquick PCR Purification kit (QIAGEN), the four PCR fragments were assembled in a second PCR round using the kit GC-Advantage obtained from Clontech under PCR 4 (see Table 2), using buffer D 1X. The crude PCR product was then amplified by PCR using PCR 5 protocol, the GC-Advantage kit, and the primers 1 and 2 in buffer D 1X. Subsequently, the product was purified using the QIAquick Gel extraction gel (QIAGEN).

Buffer D 1X 40 mM Tricine-KOH (pH 9,2)

15 mM KOAc 3.5 mM Mg(OAc)2

5% DMSO 3.75 μg/ml BSA 0.005% Noninet P-40

0.005% Tween-20

After subcloning into pHEN1 vectors using restriction sites FseI/NotI or PstI/NheI, $1.1 \times 10^7$ distinct clones were obtained by electroporation in E. coli strain TG1.

TABLE 1

| | Oligonuleotides and primers |
|---|---|
| SEQ ID NO: | Oligonucleotide sequences |
| 1 | TAACAATAGGCCGGCCACCCCTTC |
| 2 | GAGTTTTTGTTCTGCGGC |
| 3 | TTTAATCATCTGCAGTACCGGGAGCTC |
| 4 | TTCATTCTTGCTAGCTCCTGGGAGAGGC |
| 5 | CCG GCC ACC CCT TC(C AR/A VY)C TCA AC(C AR/A VY)CGG GAC CAG CTG GAA AG |
| 6 | GGA TGA GGT CCG GCA A(YT G/RB T) (YT G/RB T)AA T(YT G/RB T)GG TGC T CT TCA GCT T(YT G/RB T)GA GCT CCC GGT ACT GCA GG |
| 7 | CAA CCA GAC GGC CAC G(CA R/AV Y)AC GGG CAG GCT A(CA R/AV Y)AG CTC C(CA R/AV Y)CC CAA CCT CCA GAA CAT CC |
| 8 | CCG CCT CCC GCA C(YT G/RB T)CT TCA C(YT G/RB T)GG CCT CTA GGT CTG GCA C |
| 9 | CCT GCA GTA CCG GGA GCT C(CA R/AV Y)AA GCT GAA GAG CAC C(CA R/AV Y)AT T(CA R/AV Y)(CA R/AV Y)TT GCC GGA CCT CAT CC |

TABLE 1-continued

Oligonuleotides and primers

| SEQ ID NO: | Oligonucleotide sequences |
|---|---|
| 10 | GGA TGT TCT GGA GGT TGG G(YTG/RBT)GG AGC T(YTG/RBT)TA GCC TGC CCG T(YTG/RBT)CG TGG CCG TCT GGT TG |
| 11 | GTG CCA GAC CTA GAG GCC (CAR/AVY) GTG AAG (CAR/AVY) GTG CGG G AG GCG G |
| 12 | AAA UAC AAC AAU AAA ACG CCA CAU CUU GCG |
| 13 | TAA CAC GAC AAA GCG CAA GAT GTG GCG T |
| 14 | AAA TAC AAC AAT AAA ACG CCA CAT CTT GCG |
| 15 | TTCATTCTTGCTAGCTCCTGGGAGAGGC |
| 16 | GAG AAG ATC CTG CAG TAC CGG GAG C |
| 17 | GACCAAC ATCAAGACTGCC |
| 18 | TTGGCCAGGAACTTGTCC |

TABLE 2

PCR cycles

| | a | b | c | d | e | # of repeated Cycles |
|---|---|---|---|---|---|---|
| PCR 1 | 94° C., 3' | 94° C., 1' | 66° C., 1' | 72° C., 2' | 72° C., 15' | b-d = 30 |
| PCR 2 | 94° C., 3' | 94° C., 1' | 62° C., 1' | 72° C., 2' | 72° C., 15' | b-d = 30 |
| PCR 3 | 94° C., 3' | 94° C., 30" | 59° C., 30" | 72° C., 1' | 72° C., 15' | b-d = 30 |
| PCR 4 | 94° C., 3' | 94° C., 30" | 68° C., 1.5' | 68° C., 6' | | b-c = 35 |
| PCR 5 | 94° C., 1' | 94° C., 30" | 70° C., 30" | 72° C., 1' | 72° C., 15' | b-d = 25 |
| PCR 6 | 94° C., 3' | 94° C., 30" | 59° C., 30" | 72° C., 1' | 72° C., 15' | b-d = 35 |
| PCR 7 | 94° C., 3' | 94° C., 1' | 58° C., 1' | 72° C., 2' | 72° C., 15' | b-d = 35 |

Phage Preparation and Selection

For phage preparation, *E. coli* TG1 transformed by the phagemid library and grown to an optical density of 0.3 at 600 nm were infected by a twenty-fold excess of helper phage. Phage particles were produced at 30° C. for 19 hours in a 2×TY medium containing 100 mg/l ampicillin, 25 mg/l kanamycin. After removal of bacteria by two centrifugation (4000 rpm, 4° C.), phage particles in the supernatant were purified by two precipitations in 4% polyethyleneglycol in 0.5 M NaCl, resuspended in 1 ml of PBS (pH 7.4), and dialyzed four times against PBS over a period of 24 hours. The pH of the final solution was raised to pH 8.

The protocol for selection was as described previously (Jestin J. L., Kristensen P., Winter G. A method for the selection of catalysis using phage display and proximity coupling. Angew. Chem. Int. Ed. 1999, 38, 8, 1124-1127; Vichier-Guerre S., Jestin J. L. Iterative cycles of in vitro protein selection for DNA polymerase activity, *Biocat. & Biotransf.* 2003, 21, 75-78), except that $10^{10}$ infectious phages particles were used after heating at 65° C. for 5 minutes and that DNA polymerization was done at 65° C.

Substrate cross-linking on phage was done by incubating the phage particles with 10 µM maleimidyl-derivatized primer, 50 µM RNA template of SEQ ID NO: 12 in the presence of 10 mM magnesium chloride at 37° C. for 2 hours and polymerization during 2 minutes at 65° C. after addition of 3 µM biotin-dUTP and 1 µM dVTP.

The reactions were blocked by addition of one volume of 0.25 M ethylene diamine tetra-acetate. The phage mixture was added to 200 µl of streptavidin-coated superparamagnetic beads (Dynabeads M-280, Dynal). After 30 minutes at room temperature, the beads were washed seven times and resuspended in 200 µl PBS.

The phage-bead mixture was incubated for 10 min at 37° C. after addition of one-tenth, in volume, of trypsin (0.1 g/l). 1.8 mL of *E. coli* TG1 was then added for infection during 25 min at 37° C. Bacteria were plated on 530 cm² Petri dishes (Corning). After 12 hours at 30° C., bacteria were scraped from the plate with a 2×TY medium containing ampicillin and about $2 \times 10^9$ cells were used for preparation of the phage particles.

RT-polymerization and Polymerization Activity Assay Using Phage-polymerase

In the following examples, the activity of the different mutant phage-polymerases was assayed by incorporation of radiolabeled dTTP.

Example 1

Polyclonal Phage-polymerases (FIG. 1)

In this example, the reverse transcriptase activity of phage-polymerases was assessed as obtained after different rounds of selection in the presence of $Mg^{2+}$ or $Mn^{2+}$ ions. In these experiments, two reverse transcription (RT) mixes were used. The final concentration of each component in a reaction was: 10 μM RNA (SEQ ID NO: 12); 5 μM DNA (SEQ ID NO: 13); 0.25 mM dNTP; 3 mM MgCl$_2$ or 2.5 mM MnCl$_2$.

Each 1.9 μl aliquot of the reaction mix was further added to 15 μl of phage-polymerases (10$^8$ particles) after a given selection round heated for 5 min at 65° C. The solutions were then incubated at 37° C. for 15 min. The reactions were stopped by adding 15 μl of EDTA/formamide containing denaturation solution, heating for 3 min. at 94° C., and placed on ice. The incorporation of alpha $^{32}$P-dTTP was determined on 20% polyacrylamide gel; 15 μl of the final reaction volume were loaded.

The lane designations in FIG. 1 are as follows:

| MnCl$_2$ | MgCl$_2$ |
|---|---|
| a: phage-polymerases of round 6 | h: phage-polymerases of round 6 |
| b: phage-polymerases of round 5 | i: phage-polymerases of round 5 |
| c: phage-polymerases of round 4 | j: phage-polymerases of round 4 |
| d: phage-polymerases of round 3 | k: phage-polymerases of round 3 |
| e: phage-polymerases of round 2 | l: phage-polymerases of round 2 |
| f: phage-polymerases of round 1 | m: phage-polymerases of round 1 |
| g: phage-polymerases of initial population | n: phage-polymerases of initial population |

This experiment demonstrated that:
A RT-activity is present using phage-polymerase obtained after round 5 (i) or 6 (h) of selection in presence of Mg$^{2+}$.
A high RT-activity was detected at the round 3 (d) in the presence of Mn$^{2+}$ and for further rounds.

Example 2

Polyclonal Phage-polymerases (FIG. 2)

In this example, the reverse transcriptase activity of phage-polymerases was assessed as obtained after different rounds of selection in the presence of Mg$^{2+}$ ions. In these experiments, a reverse transcription (RT) mix was used. The final concentration of each component in a reaction was: 10 μM RNA (SEQ ID NO: 12); 5 μM DNA (SEQ ID NO: 13); 0.25 mM dNTP; 3 mM MgCl$_2$.

Each 1.2 μl aliquot of the reaction mix was further mixed with 15 μl of phage-polymerase polymerases (10$^8$ particles) after one round of selection round, either not preheated or heated 5 min at 65° C. before reaction of polymerization. The solutions were then incubated at 37° C. for 15 min. The reactions were stopped by adding 15 μl of the denaturation solution, heating for 3 min. at 94° C. and placing on ice.

The incorporation of alpha $^{32}$P-dTTP was determined on 20% polyacrylamide gel; 15 μl of the final reaction volume were loaded. The positive control was performed with addition of different concentration of commercial AMV reverse transcriptase (Promega).

The lane designations in FIG. 2 are as follows:

| Phage-polymerase heated at 65° C. for 5 min. | Phage-polymerase not preheated |
|---|---|
| a: phage-polymerases of initial population | h: phage-polymerases of initial population |
| b: phage-polymerases of round 1 | i: phage-polymerases of round 1 |
| c: phage-polymerases of round 2 | j: phage-polymerases of round 2 |
| d: phage-polymerases of round 3 | k: phage-polymerases of round 3 |

-continued

| Phage-polymerase heated at 65° C. for 5 min. | Phage-polymerase not preheated |
|---|---|
| e: phage-polymerases of round 4 | l: phage-polymerases of round 4 |
| f: phage-polymerases of round 5 | m: phage-polymerases of round 5 |
| g: phage-polymerases of round 6 | n: phage-polymerases of round 6 |
| | o: control AMV-RT, 1 U |
| | p: control AMV-RT, 0.1 U |
| | q: control AMV-RT, 0.01 U |
| | r: control AMV-RT, 0.001 U |

This experiment demonstrated that:
A RT-activity is present using phage-polymerase obtained after round 5 or 6 of selection preheated for 5 min. at 65° C. (f and g) or not (m and n) as in FIG. 1 in presence of Mg$^{2+}$.
A high RT-activity was detected using 1 unit of AMV-RT (o) but no activity was detected using decreasing concentration of AMV-RT.

Example 3

Monoclonal Phage-polymerases (FIG. 3)

In this example, the reverse transcriptase activity of various monoclonal phage-polymerases obtained after round 6 in the presence of Mg$^{2+}$ ions was assessed. In these experiments, a reverse transcription (RT) mix was prepared in which the final concentration of each component in a reaction was: 10μM RNA (SEQ ID NO: 12); 5 μM DNA (SEQ ID NO: 13); 0.25 mM dNTP; 3 mM MgCl$_2$.

Each 1.45 μl aliquot of the reaction mix was further mixed with 15 μl of phage-polymerase heated for 5 min at 65° C. The solutions were then incubated at 37° C. for 20 min. The reactions were stopped by adding 15 μl of denaturation solution, heating for 3 min. at 94° C., and placed on ice.

The incorporation of alpha $^{32}$P-dTTP was determined on a 20% polyacrylamide gel; 15 μl of the final reaction volume were loaded. The positive control was performed using the AMV-RT (Promega), lane C.

The different monoclonal phage-polymerases were obtained among the phage-polymerases of round 6. The phage-polymerases present various DNA-polymerase RNA-dependant activities. The lane designations in FIG. 3 are as follows: s=SEQ ID NO: 38; a=SEQ ID NO: 20; d=SEQ ID NO: 24; g=SEQ ID NO: 28; C=AMV-RT; i=SEQ ID NO: 30; m=SEQ ID NO: 32; n=SEQ ID NO: 34; b=SEQ ID NO: 22; and q=SEQ ID NO: 36.

The clones a, b, and d possess a high RT-activity, which were further studied as reported in FIG. 4. Randomly chosen clones from the selected populations were assayed for monoclonal phage-polymerase reverse transcriptase activity and that further sequencing of the corresponding mutant genes revealed identical sequences (for example, 7 clones reported on the figure were found to have the same sequence noted a).

Example 4

Monoclonal Phage-polymerases (FIG. 4)

In this example, the reverse transcriptase and the polymerase activities of monoclonal phage-polymerases obtained after the round 6 in the presence of Mg$^{2+}$ or Mn$^{2+}$ ions was assessed. In these experiments, the final concentration of each component in a reaction was:

10 µM RNA (SEQ ID NO: 12); 5 µM DNA (SEQ ID NO: 13); 0.25 mM dNTP; 3 mM MgCl$_2$ or 2.5 mM MnCl$_2$; and 1 µM DNA (SEQ ID NO: 14); 1 µM DNA (SEQ ID NO: 13); 0.25 mM dNTP; 3 mM MgCl$_2$ or 2.5 mM MnCl$_2$ 2 µl aliquots of the reaction mix were further added to 15 µl of each phage-polymerase pre-heated for 5 min at 65° C. The solutions were then incubated at 37° C. for 15 min. The reactions were stopped by adding 15 µl of denaturation solution, heating 3 min. at 94° C., and placed on ice.

The incorporation of alpha $^{32}$P-dTTP was determined on polyacrylamide gel; 15 µl of the final reaction volume were loaded. The positive control was performed using the phage Stoffel fragment (e).

The lane designations in FIG. 4 are as follows: a=SEQ ID NO: 20; b=SEQ ID NO: 22; d=SEQ ID NO: 24; and e=SEQ ID NO: 26.

Three families of phage polymerase were characterized among the phage-polymerases of round 6.

The phage-polymerases a and b present a high DNA-polymerase DNA-dependent activity, which is higher than that of Stoffel phage-polymerase.

The phage-polymerases b and d present a high DNA-polymerase RNA-dependent activity, which is higher than that of the Stoffel phage-polymerase e (not detectable, see figure) or than the phage-polymerase a, whatever the conditions in the presence of magnesium or of manganese.

The phage-polymerase d shows a poor DNA-polymerase DNA-dependent activity, which is lower than the activity of the Stoffel phage-polymerase.

Construction and Overproducing Clones

Three phagemids corresponding to clones a, b and d on FIG. 4 were isolated from individual colonies of *E. coli* strain TG1. The plasmid DNA was prepared and purified using Wizard Plus miniprep kits. The phagemids were cleaved with NcoI and NotI restriction endonucleases. The fragments were dephosphorylated with alkaline phosphatase, purified on QIAgen QIAquick and ligated into expression vector pET-28b(+) (Novagen) that had been cleaved with NcoI and NotI and containing a sequence for the thrombin cleavage site between the NotI and XhoI restriction sites (GCGGCCG-CACTGGTGCCGCGCGGCAGC CTCGAG; SEQ ID NO: 45).

Recombinant plasmids were transformed in *E. coli* strain BL21 pLysS and plated on 2YT media with kanamycin and chloramphenicol. Correct plasmid constructions were initially identified by restriction analysis of plasmid miniprep.

*E. coli* strain BL21, used as a host for recombinant plasmids to over produce the mutant RT-polymerase, was grown in 2YT medium supplemented with 10 µg/ml kanamycin and 25 µg/ml chloramphenicol to propagate plasmids and 1 mM of isopropyl-1-thio-β-D-galactopyranoside (IPTG) to induce production of enzyme.

Purification of Mutant RT-polymerases

Mutants were prepared from 500 ml batches of cells. 2YT media plus kanamycin and chloramphenicol was inoculated with bacteria (containing a recombinant plasmid) freshly picked on a plate and grown at 37° C. to an absorbance at 600 nm of approximately 0.5. Subsequently, IPTG was added to a final concentration of 1 mM and the cultures were allowed to further grow for 5 h.

Cells were harvested by centrifugation at 15000 g and 4° C. for 10 min., resuspended in 30 ml of lysis buffer (50 mM Na$_2$HPO$_4$, 300 mM NaCl, 5 mM imidazole, pH=8), lysed 3 times for 45 sec by ultrasound. Cell debris were removed by centrifugation at 10000 g and 4° C. for 15 min.

Mutant RT polymerases were recovered from this clarified lysate and purified using Ni-NTA agarose (QIAGEN).

Example 5

Purified Mutant RT-polymerases a, b, and d Used in Polymerase Chain Reaction (FIG. 5)

After purification on Ni-NTA agarose, the mutant polymerases were dialyzed in buffer Tris 100 mM, pH=8 and stored at 4° C.

| PCR mix | |
|---|---|
| Component | Amount |
| Buffer B 10X (*) | 20 µl |
| MgCl$_2$ 25 mM | 10 µl |
| primer 15 (50 µM) | 4 µl |
| primer 16 (50 µM) | 4 µl |
| dNTP 25 mM | 2 µl |
| Water | 157.5 µl |
| Template (Stoffel fragment gene) | 2 µl |
| Pfu polymerase (3 U/µl) | 0.5 µl |

(*) See Buffer B composition above

The PCR was performed using 19 µl of PCR mix and 0.6 µl of mutant-polymerase, a, b and d.

The lanes in the gel appearing in FIG. 5 include the three clones corresponding to clones a, b and d on FIG. 4. In addition, the positive control was performed using the Stoffel fragment polymerase e and commercial Taq DNA polymerase (Promega). The lanes in FIG. 5 are as follows:

lane 1: Taq
lane 2: a=SEQ ID NO: 20
lane 3: b=SEQ ID NO: 22
lane 4: d=SEQ ID NO: 24
lane 5: e=SEQ ID NO: 26
lane 6: Molecular weight marker Example 6

Purified Mutant RT-polymerases a, b, and d Used in RT-polymerase Chain Reaction (FIG. 6)

The positive control was performed using the phage-polymerase of AMV-RT (Promega).

These studies were performed using the three clones corresponding on clones a, b and d in FIG. 4.

The reverse transcription was performed at 65° C. during 1 h using the following conditions.

| Control RT mix | |
|---|---|
| Component | Amount |
| RNA from rabbit globin (sigma), 20 µg/ml | 1 µl |
| primer 17 (5 µM) | 0.4 µl |
| primer 18 (5 µM) | 0.4 µl |
| buffer A (**)AMV-RT 5X | 3 µl |
| dNTP 2.5 mM | 0.8 µl |
| AMV-RT 10 U/µl | 3 µl |
| water | 6.4 µl |

(**) See buffer A composition above

RT mix

| Component | Amount |
| --- | --- |
| RNA from rabbit globin (sigma), 20 µg/ml | 1 µl |
| primer 17 (5 µM) | 0.4 µl |
| primer 18 (5 µM) | 0.4 µl |
| MgCl$_2$ 25 mM | 0.75 |
| buffer C (***) | 1.5 µl |
| dNTP 2.5 mM | 0.8 µl |
| mutant polymerase a, b, d or the Stoffel fragment e | 3 µl |
| water | 7.15 µl |

(***) See buffer C composition above

The PCR was performed using PCR 7 (see table 2) and following conditions.

PCR mix

| Component | Amount |
| --- | --- |
| Buffer B 10x | 20 µl |
| primer 17 (50 µM) | 4 µl |
| primer 18 (50 µM) | 4 µl |
| dNTP | 2 µl |
| water | 164.5 µl |
| Taq DNA polymerase (5 U/µl) | 5 µl |
| Pfu polymerase (3 U/µl) | 0.5 µl |

19 µl aliquot of the PCR mix was added to 1 µl of the RT reaction product.

A RT-PCR product of 372 bp was detectable using mutant RT-polymerases b and d.

The lanes in the gel appearing in FIG. 6 include the three clones corresponding to clones a, b and d on FIG. 4. In addition, the positive control was performed using the Stoffel fragment polymerase e and the commercial AMV-RT (Promega).

The lanes in FIG. 6 are as follows:
lane 1: molecular weight marker
lane 2: control AMV-RT
lane 3: b=SEQ ID NO: 22
lane 4: a=SEQ ID NO: 20
lane 5: e=SEQ ID NO: 26
lane 6: d=SEQ ID NO: 24

Summary of the Taq Sequence Variants Above

In the N-terminus of the purified proteins, the signal sequence is not taken in account, the peptide having the sequence MASG$_4$CG$_4$ (SEQ ID NO: 39) has been introduced upstream the sequence SPKA (amino acids 13-16 of SEQ ID NO: 26), which correspond to the Stoffel fragment beginning (S being the amino acid occupying the position number 290 in the Taq polymerase sequence).

In the C-terminus of the purified proteins, the sequence AAALVPRGSLEH$_6$ (SEQ ID NO: 40) comprising a site of cleavage by thrombin, as well as a polyhistidine tag has been introduced to facilitate further purification of the protein.

| Mutations Assessment | Phage | SEQ ID NO: |
| --- | --- | --- |
| M761V* | "s" | 38 |
| M761T, D547G, I584V | "a" | 20 |
| W827R | "m" | 32 |
| W827R, E520G, A608T | "b" | 22 |
| W827R, A517V, T664S, F769S | "g" | 28 |
| M747K, Q698L, P816L | "n" | 34 |
| M747R, W604R, S612N, V730L, R736Q, S739N, N483Q, S486Q, T539N, Y545Q, D547T, P548Q, A570Q, D578Q, A597T | "d" | 24 |
| F749Y, A568V | "i" | 30 |
| F749Y, P550Q, R556S, V740E, V819A | "q" | 36 |

*The mutation designations above, e.g., M761V, refer to the wild-type sequence of Taq polymerase. M761V would correspond to M484V of SEQ ID NO: 26 and M761T would correspond to M484T of SEQ ID NO: 26.

Numerous modifications and variations on the present invention are possible in light of the above teachings. It is, therefore, to be understood that within the scope of the accompanying claims, the invention may be practiced otherwise than as specifically described herein.

REFERENCES

1. Bothmann, H. and Plückthun, A. (1998) Selection for a periplasmic factor improving phage display and functional periplasmic expression. *Nat. Biotech.* 16, 376-380.

2. Jestin, J. L., Volioti, G. and Winter, G. (2001) Improving the display of proteins on filamentous phage. *Res. Microbiol.* 152, 187-191.

3. Holland, M. M., Leib, T. K., and Gerlt, J. A. (1988) Isolation and characterization of a small catalytic domain released from the adenylate cyclase from *Escherichia coli* by digestion with trypsin. *J Biol. Chem.* 263, 14661-14668.

4. Ladant, D., Glaser, P., and Ullmann, A. (1992) Insertional mutagenesis of *Bordetella pertussis* adenylate cyclase. *J. Biol. Chem.* 267, 2244-2250.

5. Hoogenboom, H. R., Griffiths, A. D., Johnson, K. S., et al. (1991) Multi-subunit proteins on the surface of filamentous phage: methodologies for displaying antibody Fab heavy and light chains. *Nucl. Acids Res.* 19, 4133-4137.

6. Kristensen, P. and Winter, G. (1998) Proteolytic selection for protein folding using filamentous bacteriophages. *Fold. Design* 3, 321-328.

7. Lei, S. P., Lin, H. C., Wang, S. S., Callaway, J., et al. (1987) Characterization of the *Erwinia carotovora*; pelB gene and its product pectate lyase. *J. Bacteriol.* 169, 4379-4383.

8. Tesar, M., Beckmann, C., Rottgen, P., et al. (1995) Monoclonal antibody against pIII of filamentous phage: an immunological tool to study pill fusion protein expression in phage display systems. *Immunotechnology* 1, 53-64.

9. Pedersen, H., Hölder, S., Sutherlin, D. P., et al. (1998) A method for directed evolution and functional cloning of enzymes. *Proc. Natl. Acad. Sci. USA* 95, 10523-10528.

10. Jestin, J. L., Kristensen, P., and Winter, G. (1999) A method for the selection of catalytic activity using phage display and proximity coupling. *Angew. Chem. Int. Ed.* 38, 1124-1127.

11. Dematris, S., Huber, A., et al. (1999) A strategy for the isolation of catalytic activities from repertoires of enzymes displayed on phage. *J. Mol. Biol.* 286, 617-633.

12. Heinis, C., Huber, A. et al. (2001) Selection of catalytically active biotin ligase and trypsin mutants by phage display. *Protein Eng.* 14, 1043-1052.

13. Atwell, S. and Wells, J. A. (1999) Selection for improved subtiligases by phage display. *Proc. Natl. Acad. Sci. USA* 96, 9497-9502.

14. Ponsard, I., Galleni, M., Soumillion, P., Fastrez, J., Selection of metalloenzymes by catalytic activity using phage display and catalytic elution. *Chembiochem.* 2, 253-259.

15. Lawyer, F. C., Stoffel, S., Saiki, R. K., et al. (1989) Isolation, characterisation and expression in *E. coli* of the DNA polymerase gene from *Thermus aquaticus. J. Biol. Chem.* 264, 6427-6437.

16. Marks et al., (1992) Molecular evolution of proteins on filamentous phage, Mimicking the strategy of the immune system. *J. Biol. Chem.* 267, 16007-16010.

17. Vichier-Gurre & Jestin, (2003) Iterative cycles of in vitro protein selection for DNA polymerase activity, *Biocat. &Biotransf.* 21, 75-78.

18. Fastrez et al., (2002) Investigation of phage display for the directed evolution of enzymes," In: Brackmann, S. and Johnsson, K. eds., *Directed Molecular Evolution of Proteins* (Wiley VCH, Weinheim), pp 79-110

19. Ponsard et al. (2001) Selection of metalloenzymes by catalytic activity using phage display and catalytic elution. *Chembiochem.* 2, 253-259.

20. Ting et al. (2001) Phage-display evolution of tyrosine kinases with altered nucleotide specificity. *Biopol.* 60, 220-228.

21. Xia et al. (2002) Directed evolution of novel polymerase activities: mutation of a DNA polymerase into an efficient RNA polymerase. *Proc. Natl. Acad. Sci. USA* 99, 6597-6602.

22. Rougeon, F., Kourilsky, P., Mach, B. Insertion of a rabbit beta-globin gene sequence into an *E. coli* plasmid *Nucl. Acids Res.,* 1975, 2, 2365-2378.

23. Rougeon, F., Mach, B. Stepwise biosynthesis in vitro of globin genes from globin mRNA by DNA polymerase of avian myeloblastosis virus *Proc. Natl. Acad. Sci. USA,* 1976, 73, 3418-3422.

24. Grabko, V. I., Chistyakova, L. G., Lyapustin, V. N., Korobko, V. G., Miroshnikov, A. I., Reverse transcription, amplification and sequencing of poliovirus RNA by Taq DNA polymerase *FEBS Letters,* 1996, 387, 189-192.

25. Perler, F., Kumar, S., Kong, H. Thermostable DNA polymerases *Adv. Prot. Chem.,* 1996, 48, 377-435.

The invention claimed is:

1. An isolated polynucleotide which encodes a thermostable polypeptide having DNA polymerase activity comprising:
   an amino acid sequence having at least 95% identity to the amino acid sequence of SEQ ID NO: 26,
   wherein said polypeptide has a mutation at residue 484 of the amino acid sequence of SEQ ID NO: 26 which replaces the methionine residue (Met) with a different amino acid residue.

2. The isolated polynucleotide of claim 1, which encodes a polypeptide having one of the following mutations: M484V or M484T.

3. The isolated polynucleotide of claim 1, wherein said polypeptide further comprises at least one mutation selected from the group consisting of A331T, S335N, M470K, M470R, F472Y, and W550R.

4. The isolated polynucleotide of claim 1, wherein said polypeptide further comprises at least one other mutation in amino acids 461 to 490 of SEQ ID NO: 26, or at a position selected from the group consisting of A331, L332, D333, Y334, S335, M470, F472, W550, L332, D333, and Y334.

5. The isolated polynucleotide of claim 1, wherein said polypeptide has at least 97.5% identity to the amino acid sequence of SEQ ID NO: 26.

6. The isolated polynucleotide of claim 1, wherein said polypeptide comprises at least two mutations of the amino acid sequence of SEQ ID NO: 26.

7. The isolated polynucleotide of claim 1, which comprises SEQ ID NO: 19.

8. The isolated polynucleotide of claim 1, wherein said polypeptide comprises SEQ ID NO: 20.

9. The isolated polynucleotide of claim 1, consisting of SEQ ID NO: 19, or SEQ ID NO: 37.

10. An isolated polynucleotide that is fully complementary to the polynucleotide of claim 1.

11. An isolated polynucleotide which hybridizes under stringent conditions to the polynucleotide of claim 1; and which encodes a polypeptide that has a mutation at residue 484 of the amino acid sequence of SEQ ID NO: 26 which replaces the methionine residue (Met) with a different amino acid residue;
   wherein said stringent conditions comprise washing in 0.1×SSC at a temperature of 68° C.

12. A vector comprising the isolated polynucleotide of claim 1.

13. The vector of claim 12, wherein said polynucleotide is operably linked to a heterologous expression sequence.

14. An isolated host cell comprising to isolated polynucleotide of claim 1.

15. A monoclonal phage selected from the group consisting of SJL s (CNCM I-3171), and SJL a (CNCM I-3176).

16. An isolated recombinant host cell comprising the phage of claim 15.

17. The isolated polynucleotide of claim 1 which encodes a polypeptide having DNA polymerase activity and reverse transcriptase activity in the absence of manganese.

* * * * *

SEQUENCE LISTING

```
<160> NUMBER OF SEQ ID NOS: 61

<210> SEQ ID NO 1
<211> LENGTH: 24
<212> TYPE: DNA
<213> ORGANISM: Artificial Sequence
<220> FEATURE:
<223> OTHER INFORMATION: Synthetic DNA

<400> SEQUENCE: 1
taacaatagg ccggccaccc cttc                                                 24

<210> SEQ ID NO 2
<211> LENGTH: 18
<212> TYPE: DNA
<213> ORGANISM: Artificial Sequence
<220> FEATURE:
<223> OTHER INFORMATION: Synthetic DNA

<400> SEQUENCE: 2 gagttttttgt tctgcggc                                                       18

<210> SEQ ID NO 3
<211> LENGTH: 27
<212> TYPE: DNA
<213> ORGANISM: Artificial Sequence
<220> FEATURE:
<223> OTHER INFORMATION: Synthetic DNA

<400> SEQUENCE: 3
tttaatcatc tgcagtaccg ggagctc                                              27

<210> SEQ ID NO 4
<211> LENGTH: 28
<212> TYPE: DNA
<213> ORGANISM: Artificial Sequence
<220> FEATURE:
<223> OTHER INFORMATION: Synthetic DNA

<400> SEQUENCE: 4
ttcattcttg ctagctcctg ggagaggc                                             28
```

<210> SEQ ID NO 5
<211> LENGTH: 43
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (15)..(15)
<223> OTHER INFORMATION: n represents the following sequences in a 1:1
      relative abundance: C and A, in the trimer sequence CAR and AVY,
      respectively
<220> FEATURE:
<221> NAME/KEY: misc_feature
<222> LOCATION: (16)..(16)
<223> OTHER INFORMATION: n represents the following sequences in a 1:1
      relative abundance: A and V, in the trimer sequence CAR and AVY,
      respectively
<220> FEATURE:
<221> NAME/KEY: misc_feature
<222> LOCATION: (17)..(17)
<223> OTHER INFORMATION: n represents the following sequences in a 1:1
      relative abundance: R and Y, in the trimer sequence CAR and AVY,
      respectively
<220> FEATURE:
<221> NAME/KEY: misc_feature
<222> LOCATION: (24)..(24)
<223> OTHER INFORMATION: n represents the following sequences in a 1:1
      relative abundance: C and A, in the trimer sequence CAR and AVY,
      respectively
<220> FEATURE:
<221> NAME/KEY: misc_feature
<222> LOCATION: (25)..(25)
<223> OTHER INFORMATION: n represents the following sequences in a 1:1
      relative abundance: A and V, in the trimer sequence CAR and AVY,
      respectively
<220> FEATURE:
<221> NAME/KEY: misc_feature
<222> LOCATION: (26)..(26)
<223> OTHER INFORMATION: n represents the following sequences in a 1:1
      relative abundance: R and Y, in the trimer sequence CAR and AVY,
      respectively

<400> SEQUENCE: 5
ccggccaccc cttcnnnctc aacnnncggg accagctgga aag                        43

<210> SEQ ID NO 6
<211> LENGTH: 65
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (17)..(17)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (18)..(18)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (19)..(19)
<223> OTHER INFORMATION: n represents the following sequences in a 1:1
      relative abundance: G and T, in the trimer sequence YTG and RBT,
      respectively
<220> FEATURE:
<221> NAME/KEY: misc_feature
<222> LOCATION: (20)..(20)
<223> OTHER INFORMATION: n represents the following sequences in a 1:1
      relative abundance: Y and R, in the trimer sequence YTG and RBT,
      respectively

```
<220> FEATURE:
<221> NAME/KEY: misc_feature
<222> LOCATION: (21)..(21)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (22)..(22)
<223> OTHER INFORMATION: n represents the following sequences in a 1:1
      relative abundance: G and T, in the trimer sequence YTG and RBT,
      respectively
<220> FEATURE:
<221> NAME/KEY: misc_feature
<222> LOCATION: (26)..(26)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (27)..(27)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (28)..(28)
<223> OTHER INFORMATION: n represents the following sequences in a 1:1
      relative abundance: G and T, in the trimer sequence YTG and RBT,
      respectively
<220> FEATURE:
<221> NAME/KEY: misc_feature
<222> LOCATION: (44)..(44)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (45)..(45)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (46)..(46)
<223> OTHER INFORMATION: n represents the following sequences in a 1:1
      relative abundance: G and T, in the trimer sequence YTG and RBT,
      respectively

<400> SEQUENCE: 6
ggatgaggtc cggcaannnn nnaatnnngg tgctcttcag cttnnngagc tcccggtact        60
gcagg                                                                    65

<210> SEQ ID NO 7
<211> LENGTH: 62
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (17)..(17)
<223> OTHER INFORMATION: n represents the following sequences in a 1:1
      relative abundance: C and A, in the trimer sequence CAR and AVY,
      respectively
<220> FEATURE:
<221> NAME/KEY: misc_feature
<222> LOCATION: (18)..(18)
<223> OTHER INFORMATION: n represents the following sequences in a 1:1
      relative abundance: A and V, in the trimer sequence CAR and AVY,
      respectively
<220> FEATURE:
<221> NAME/KEY: misc_feature
<222> LOCATION: (19)..(19)
<223> OTHER INFORMATION: n represents the following sequences in a 1:1
      relative abundance: R and Y, in the trimer sequence CAR and AVY,
```

-continued

```
        respectively
<220> FEATURE:
<221> NAME/KEY: misc_feature
<222> LOCATION: (32)..(32)
<223> OTHER INFORMATION: n represents the following sequences in a 1:1
      relative abundance: C and A, in the trimer sequence CAR and AVY,
      respectively
<220> FEATURE:
<221> NAME/KEY: misc_feature
<222> LOCATION: (33)..(33)
<223> OTHER INFORMATION: n represents the following sequences in a 1:1
      relative abundance: A and V, in the trimer sequence CAR and AVY,
      respectively
<220> FEATURE:
<221> NAME/KEY: misc_feature
<222> LOCATION: (34)..(34)
<223> OTHER INFORMATION: n represents the following sequences in a 1:1
      relative abundance: R and Y, in the trimer sequence CAR and AVY,
      respectively
<220> FEATURE:
<221> NAME/KEY: misc_feature
<222> LOCATION: (41)..(41)
<223> OTHER INFORMATION: n represents the following sequences in a 1:1
      relative abundance: C and A, in the trimer sequence CAR and AVY,
      respectively
<220> FEATURE:
<221> NAME/KEY: misc_feature
<222> LOCATION: (42)..(42)
<223> OTHER INFORMATION: n represents the following sequences in a 1:1
      relative abundance: A and V, in the trimer sequence CAR and AVY,
      respectively
<220> FEATURE:
<221> NAME/KEY: misc_feature
<222> LOCATION: (43)..(43)
<223> OTHER INFORMATION: n represents the following sequences in a 1:1
      relative abundance: R and Y, in the trimer sequence CAR and AVY,
      respectively

<400> SEQUENCE: 7
caaccagacg gccacgnnna cgggcaggct annnagctcc nnncccaacc tccagaacat      60
cc                                                                    62

<210> SEQ ID NO 8
<211> LENGTH: 43
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(14)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (15)..(15)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (16)..(16)
<223> OTHER INFORMATION: n represents the following sequences in a 1:1
      relative abundance: G and T, in the trimer sequence YTG and RBT,
      respectively
<220> FEATURE:
<221> NAME/KEY: misc_feature
<222> LOCATION: (23)..(23)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (24)..(24)
<223> OTHER INFORMATION: n represents the following sequences in a 1:1
```

-continued

```
        relative abundance: T and B, in the trimer sequence YTG and RBT,
        respectively
<220> FEATURE:
<221> NAME/KEY: misc_feature
<222> LOCATION: (25)..(25)
<223> OTHER INFORMATION: n represents the following sequences in a 1:1
        relative abundance: G and T, in the trimer sequence YTG and RBT,
        respectively

<400> SEQUENCE: 8
ccgcctcccg cacnnncttc acnnnggcct ctaggtctgg cac                         43

<210> SEQ ID NO 9
<211> LENGTH: 65
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (20)..(20)
<223> OTHER INFORMATION: n represents the following sequences in a 1:1
        relative abundance: C and A, in the trimer sequence CAR and AVY,
        respectively
<220> FEATURE:
<221> NAME/KEY: misc_feature
<222> LOCATION: (21)..(21)
<223> OTHER INFORMATION: n represents the following sequences in a 1:1
        relative abundance: A and V, in the trimer sequence CAR and AVY,
        respectively
<220> FEATURE:
<221> NAME/KEY: misc_feature
<222> LOCATION: (22)..(22)
<223> OTHER INFORMATION: n represents the following sequences in a 1:1
        relative abundance: R and Y, in the trimer sequence CAR and AVY,
        respectively
<220> FEATURE:
<221> NAME/KEY: misc_feature
<222> LOCATION: (38)..(38)
<223> OTHER INFORMATION: n represents the following sequences in a 1:1
        relative abundance: C and A, in the trimer sequence CAR and AVY,
        respectively
<220> FEATURE:
<221> NAME/KEY: misc_feature
<222> LOCATION: (39)..(39)
<223> OTHER INFORMATION: n represents the following sequences in a 1:1
        relative abundance: A and V, in the trimer sequence CAR and AVY,
        respectively
<220> FEATURE:
<221> NAME/KEY: misc_feature
<222> LOCATION: (40)..(40)
<223> OTHER INFORMATION: n represents the following sequences in a 1:1
        relative abundance: R and Y, in the trimer sequence CAR and AVY,
        respectively
<220> FEATURE:
<221> NAME/KEY: misc_feature
<222> LOCATION: (44)..(44)
<223> OTHER INFORMATION: n represents the following sequences in a 1:1
        relative abundance: C and A, in the trimer sequence CAR and AVY,
        respectively
<220> FEATURE:
<221> NAME/KEY: misc_feature
<222> LOCATION: (45)..(45)
<223> OTHER INFORMATION: n represents the following sequences in a 1:1
        relative abundance: A and V, in the trimer sequence CAR and AVY,
        respectively
<220> FEATURE:
<221> NAME/KEY: misc_feature
<222> LOCATION: (46)..(46)
<223> OTHER INFORMATION: n represents the following sequences in a 1:1
        relative abundance: R and Y, in the trimer sequence CAR and AVY,
        respectively
<220> FEATURE:
<221> NAME/KEY: misc_feature
<222> LOCATION: (47)..(47)
<223> OTHER INFORMATION: n represents the following sequences in a 1:1
        relative abundance: C and A, in the trimer sequence CAR and AVY,
```

```
         respectively
<220> FEATURE:
<221> NAME/KEY: misc_feature
<222> LOCATION: (48)..(48)
<223> OTHER INFORMATION: n represents the following sequences in a 1:1
      relative abundance: A and V, in the trimer sequence CAR and AVY,
      respectively
<220> FEATURE:
<221> NAME/KEY: misc_feature
<222> LOCATION: (49)..(49)
<223> OTHER INFORMATION: n represents the following sequences in a 1:1
      relative abundance: R and Y, in the trimer sequence CAR and AVY,
      respectively

<400> SEQUENCE: 9
cctgcagtac cgggagctcn nnaagctgaa gagcaccnnn attnnnnnnt tgccggacct    60
catcc                                                              65

<210> SEQ ID NO 10
<211> LENGTH: 62
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (20)..(20)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (21)..(21)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (22)..(22)
<223> OTHER INFORMATION: n represents the following sequences in a 1:1
      relative abundance: G and T, in the trimer sequence YTG and RBT,
      respectively
<220> FEATURE:
<221> NAME/KEY: misc_feature
<222> LOCATION: (29)..(29)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (30)..(30)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (31)..(31)
<223> OTHER INFORMATION: n represents the following sequences in a 1:1
      relative abundance: G and T, in the trimer sequence YTG and RBT,
      respectively
<220> FEATURE:
<221> NAME/KEY: misc_feature
<222> LOCATION: (44)..(44)
<223> OTHER INFORMATION: n represents the following sequences in a 1:1
      relative abundance: Y and R, in the trimer sequence YTG and RBT,
      respectively
<220> FEATURE:
<221> NAME/KEY: misc_feature
<222> LOCATION: (45)..(45)
<223> OTHER INFORMATION: n represents the following sequences in a 1:1
      relative abundance: T and B, in the trimer sequence YTG and RBT,
      respectively
<220> FEATURE:
<221> NAME/KEY: misc_feature
<222> LOCATION: (46)..(46)
<223> OTHER INFORMATION: n represents the following sequences in a 1:1
``` relative abundance: G and T, in the trimer sequence YTG and RBT,
        respectively

<400> SEQUENCE: 10
ggatgttctg gaggttgggn nnggagctnn ntagcctgcc cgtnnncgtg gccgtctggt    60
tg                                                                  62

<210> SEQ ID NO 11
<211> LENGTH: 43
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (19)..(19)
<223> OTHER INFORMATION: n represents the following sequences in a 1:1
        relative abundance: C and A, in the trimer sequence CAR and AVY,
        respectively
<220> FEATURE:
<221> NAME/KEY: misc_feature
<222> LOCATION: (20)..(20)
<223> OTHER INFORMATION: n represents the following sequences in a 1:1
        relative abundance: A and V, in the trimer sequence CAR and AVY,
        respectively
<220> FEATURE:
<221> NAME/KEY: misc_feature
<222> LOCATION: (21)..(21)
<223> OTHER INFORMATION: n represents the following sequences in a 1:1
        relative abundance: R and Y, in the trimer sequence CAR and AVY,
        respectively
<220> FEATURE:
<221> NAME/KEY: misc_feature
<222> LOCATION: (28)..(30)
<223> OTHER INFORMATION: n is a, c, g, or t
<220> FEATURE:
<221> NAME/KEY: misc_feature
<222> LOCATION: (38)..(38)
<223> OTHER INFORMATION: n represents the following sequences in a 1:1
        relative abundance: C and A, in the trimer sequence CAR and AVY,
        respectively
<220> FEATURE:
<221> NAME/KEY: misc_feature
<222> LOCATION: (39)..(39)
<223> OTHER INFORMATION: n represents the following sequences in a 1:1
        relative abundance: A and V, in the trimer sequence CAR and AVY,
        respectively
<220> FEATURE:
<221> NAME/KEY: misc_feature
<222> LOCATION: (40)..(40)
<223> OTHER INFORMATION: n represents the following sequences in a 1:1
        relative abundance: R and Y, in the trimer sequence CAR and AVY,
        respectively

<400> SEQUENCE: 11
gtgccagacc tagaggccnn ngtgaagnnn gtgcgggagg cgg                     43

<210> SEQ ID NO 12
<211> LENGTH: 30
<212> TYPE: RNA
<213> ORGANISM: Artificial Sequence
<220> FEATURE:
<223> OTHER INFORMATION: Synthetic DNA

<400> SEQUENCE: 12
aaauacaaca auaaaacgcc acaucuugcg                                    30

<210> SEQ ID NO 13
<211> LENGTH: 28
<212> TYPE: DNA
<213> ORGANISM: Artificial Sequence
<220> FEATURE:

<223> OTHER INFORMATION: Synthetic DNA

<400> SEQUENCE: 13
taacacgaca aagcgcaaga tgtggcgt                                        28

<210> SEQ ID NO 14
<211> LENGTH: 30
<212> TYPE: DNA
<213> ORGANISM: Artificial Sequence
<220> FEATURE:
<223> OTHER INFORMATION: Synthetic DNA

<400> SEQUENCE: 14
aaatacaaca ataaaacgcc acatcttgcg                                      30

<210> SEQ ID NO 15
<211> LENGTH: 28
<212> TYPE: DNA
<213> ORGANISM: Artificial Sequence
<220> FEATURE:
<223> OTHER INFORMATION: Synthetic DNA

<400> SEQUENCE: 15
ttcattcttg ctagctcctg ggagaggc                                        28

<210> SEQ ID NO 16
<211> LENGTH: 25
<212> TYPE: DNA
<213> ORGANISM: Artificial Sequence
<220> FEATURE:
<223> OTHER INFORMATION: Synthetic DNA

<400> SEQUENCE: 16
gagaagatcc tgcagtaccg ggagc                                           25

<210> SEQ ID NO 17
<211> LENGTH: 19
<212> TYPE: DNA
<213> ORGANISM: Artificial Sequence
<220> FEATURE:
<223> OTHER INFORMATION: Synthetic DNA

<400> SEQUENCE: 17
gaccaacatc aagactgcc                                                  19

<210> SEQ ID NO 18
<211> LENGTH: 18
<212> TYPE: DNA
<213> ORGANISM: Artificial Sequence
<220> FEATURE:
<223> OTHER INFORMATION: Synthetic DNA

<400> SEQUENCE: 18
ttggccagga acttgtcc                                                   18

<210> SEQ ID NO 19
<211> LENGTH: 1688
<212> TYPE: DNA
<213> ORGANISM: Thermus aquaticus

<400> SEQUENCE: 19
ccatggcctc tggtggcggt ggctgtggtg gcggtggcag ccccaaggcc ctggaggagg     60
ccccctggcc ccgccggaa ggggccttcg tgggctttgt gctttcccgc aaggagccca    120
tgtgggccga tcttctggcc ctggccgccg ccagggggg ccgggtccac cgggccccg     180

-continued

```
agccttataa agccctcagg gacctgaagg aggcgcgggg gcttctcgcc aaagacctga    240
gcgttctggc cctgagggaa ggccttggcc tcccgcccgg cgacgacccc atgctcctcg    300
cctacctcct ggacccttcc aacaccaccc ccgaggggt ggcccggcgc tacggcgggg     360
agtggacgga ggaggcgggg gagcgggccg cccttccga gaggctcttc gccaacctgt     420
ggggaggct tgaggggag gagaggctcc tttggcttta ccgggaggtg gagaggcccc      480
tttccgctgt cctggcccac atggaggcca cgggggtgcg cctggacgtg gcctatctca    540
gggccttgtc cctggaggtg gccgaggaga tcgcccgcct cgaggccgag gtcttccgcc    600
tggccggcca ccccttcaac ctcaactccc gggaccagct ggaaagggtc tcctttgacg    660
agctagggct tccgccatc ggcaagacgg agaagaccgg caagcgctcc accagcgccg     720
ccgtcctgga ggcccttcgc gaggcccacc ccatcgtgga agatcctg cagtaccggg      780
agctcaccaa gctgaagagc acctacattg ccccttgcc ggacctcatc cacccagga     840
cgggccgcct ccacacccgc ttcaaccaga cggccacggc cacgggcagg ctaagtagct    900
ccgatcccaa cctccagaac gtccccgtcc gcaccccgct gggcagagg atccgccggg    960
ccttcatcgc cgaggaggg tggctattgg tggccctgga ctatagccag atagagctca    1020
gggtgctggc ccacctctcc ggcgacgaga acctgatccg ggtcttccag gaggggcggg    1080
atatccacac ggagaccgcc agctggatgt cggcgtccc ccgggaggcc gtggaccccc     1140
tgatgcgccg ggcggccaag accatcaact tcggggtcct ctacggcatg tcggcccacc    1200
gcctctccca ggagctagcc atcccttacg aggaggccca ggccttcatt gagcgctact    1260
ttcagagctt ccccaaggtg cgggcctgga ttgagaagac cctggaggag gtaggaggc    1320
gggggtacgt ggagaccctc ttcggccgcc gccgctacgt gccagaccta gaggcccggg    1380
tgaagagcgt gcgggaggcg gccgagcgca tggccttcaa catgcccgtc agggcaccg    1440
ccgccgacct cacgaagctg gctatggtga agctcttccc caggctggag gaaatggggg    1500
ccaggatgct ccttcaggtc cacgacgagc tggtcctcga ggccccaaaa gaggggcgg    1560
aggccgtggc ccggctggcc aaggaggtca tggggggt gtatccctg gccgtgcccc       1620
tggaggtgga ggtggggata ggggaggact ggctctccgc caaggaggcg gccgcactgg    1680
tgccgcgc                                                           1688
```

<210> SEQ ID NO 20
<211> LENGTH: 562
<212> TYPE: PRT
<213> ORGANISM: Thermus aquaticus

<400> SEQUENCE: 20

```
Met Ala Ser Gly Gly Gly Cys Gly Gly Gly Ser Pro Lys Ala
 1               5                  10                  15

Leu Glu Ala Pro Trp Pro Pro Glu Gly Ala Phe Val Gly Phe
                20                  25                  30

Val Leu Ser Arg Lys Glu Pro Met Trp Ala Asp Leu Ala Leu Ala
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
 65                  70                  75                  80

Val Leu Ala Leu Arg Glu Gly Leu Gly Leu Pro Pro Gly Asp Asp Pro
                85                  90                  95
```

-continued

```
Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Gly Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Val Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
    450                 455                 460

Glu Ala Ala Glu Arg Met Ala Phe Asn Met Pro Val Gln Gly Thr Ala
465                 470                 475                 480

Ala Asp Leu Thr Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
```

515                 520                 525
   Val Met Glu Gly Val Tyr Pro Leu Ala Val Pro Leu Glu Val Glu Val
       530                 535                 540

Gly Ile Gly Glu Asp Trp Leu Ser Ala Lys Glu Ala Ala Ala Leu Val
545                 550                 555                 560

Pro Arg

<210> SEQ ID NO 21
<211> LENGTH: 1688
<212> TYPE: DNA
<213> ORGANISM: Thermus aquaticus

<400> SEQUENCE: 21

```
ccatggcctc tggtggcggt ggctgtggtg gcggtggcag ccccaaggcc ctggaggagg      60
cccccctggcc cccgccggaa ggggccttcg tgggctttgt gctttcccgc aaggagccca    120
tgtgggccga tcttctggcc ctggccgccg ccagggggggg ccgggtccac cgggccccccg   180
agccttataa agccctcagg gacctgaagg aggcgcgggg gcttctcgcc aaagacctga    240
gcgttctggc cctgagggaa ggccttggcc tcccgcccgg cgacgacccc atgctcctcg    300
cctacctcct ggacccttcc aacaccaccc ccgagggggt ggcccggcgc tacggcgggg    360
agtggacgga ggaggcgggg gagcgggccg cccttttccga gggctcttc gccaacctgt    420
ggggggaggct tgagggggag gagaggctcc tttggcttta ccgggaggtg gagaggcccc    480
tttccgctgt cctggcccac atggaggcca cgggggtgcg cctggacgtg gcctatctca    540
gggccttgtc cctggaggtg gccgaggaga tcgcccgcct cgaggccgag gtcttccgcc    600
tggccggcca ccccttcaac ctcaactccc gggaccagct ggaaagggtc ctctttgacg    660
agctagggct tcccgccatc ggcaagacgg agaagaccgg caagcgctcc accagcgccg    720
ccgtcctggg ggcccctccgc gaggcccacc ccatcgtgga aagatcctg cagtaccggg    780
agctcaccaa gctgaagagc acctacattg accccttgcc ggacctcatc caccccagga    840
cgggccgcct ccacacccgc ttcaaccaga cggccacggc cacgggcagg ctaagtagct    900
ccgatcccaa cctccagaac atccccgtcc gcaccccgct gggcagagg atccgccggg     960
ccttcatcgc cgaggagggg tggctattgg tgacctggga ctatagccag atagagctca    1020
gggtgctggc ccacctctcc ggcgacgaga acctgatccg ggtcttccag gaggggcggg    1080
acatccacac ggagaccgcc agctggatgt tcggcgtccc ccgggaggcc gtggacccccc    1140
tgatgcgccg ggcggccaag accatcaact tcggggtcct ctacggcatg tcggcccacc    1200
gcctctccca ggagctagcc atcccttacg aggaggccca ggccttcatt gagcgctact    1260
ttcagagctt ccccaaggtg cgggcctgga ttgagaagac cctggaggag gcaggaggc    1320
gggggtacgt ggagaccctc ttcggccgcc gccgctacgt gccagaccta gaggcccggg    1380
tgaagagcgt gcgggaggcg gccgagcgca tggccttcaa catgcccgtc cagggcaccg    1440
ccgccgacct catgaagctg gctatggtga agctcttccc caggctggag gaaatggggg    1500
ccaggatgct ccttcaggtc cacgacgagc tggtcctcga ggccccaaaa gaggggcgg    1560
aggccgtggc ccggctggcc aaggaggtca tggagggggt gtatcccctg ccgtgccccc    1620
tggaggtgga ggtgggggata ggggaggaca ggctctccgc caaggaggcg gccgcactgg    1680
tgccgcgc                                                              1688
```

<210> SEQ ID NO 22
<211> LENGTH: 562

```
<212> TYPE: PRT
<213> ORGANISM: Thermus aquaticus

<400> SEQUENCE: 22

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Ala Leu Ala
            35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
    195                 200                 205

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Ala
225                 230                 235                 240

Val Leu Gly Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
    275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Thr Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
    355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400
```

Leu Ser Gln Glu Leu Ala Ile Pro Tyr Glu Glu Ala Gln Ala Phe Ile
              405                 410                 415

Glu Arg Tyr Phe Gln Ser Phe Pro Lys Val Arg Ala Trp Ile Glu Lys
          420                 425                 430

Thr Leu Glu Glu Gly Arg Arg Arg Gly Tyr Val Glu Thr Leu Phe Gly
      435                 440                 445

Arg Arg Arg Tyr Val Pro Asp Leu Glu Ala Arg Val Lys Ser Val Arg
  450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
              485                 490                 495

Glu Met Gly Ala Arg Met Leu Leu Gln Val His Asp Glu Leu Val Leu
          500                 505                 510

Glu Ala Pro Lys Glu Gly Ala Glu Ala Val Ala Arg Leu Ala Lys Glu
      515                 520                 525

Val Met Glu Gly Val Tyr Pro Leu Ala Val Pro Leu Glu Val Glu Val
  530                 535                 540

Gly Ile Gly Glu Asp Arg Leu Ser Ala Lys Glu Ala Ala Ala Leu Val
545                 550                 555                 560

Pro Arg

<210> SEQ ID NO 23
<211> LENGTH: 1688
<212> TYPE: DNA
<213> ORGANISM: Thermus aquaticus

<400> SEQUENCE: 23

```
ccatggcctc tggtggcggt ggctgtggtg gcggtggcag ccccaaggcc ctggaggagg     60
cccccctggcc cccgccggaa ggggccttcg tgggctttgt gctttcccgc aaggagccca    120
tgtgggccga tcttctggcc ctggccgccg ccagggggggg ccgggtccac cgggcccccg    180
agccttataa agccctcagg gacctgaagg aggcgcgggg gcttctcgcc aaagacctga    240
gcgttctggc cctgagggaa ggccttggcc tcccgcccgg cgacgacccc atgctcctcg    300
cctacctcct ggaccttcc aacaccaccc cgagggggt ggcccggcgc tacgcgggg     360
agtggacgga ggaggcgggg gagcgggccg ccctttccga gaggctcttc gccaacctgt    420
gggggaggct tgaggggag gagaggctcc tttggcttta ccggggaggtg gagaggcccc    480
tttccgctgt cctggcccac atggaggcca cgggggtgcg cctggacgtg gcctatctca    540
gggccttgtc cctggaggtg gccgaggaga tcgcccgcct cgaggccgag gtcttccgcc    600
tggccggcca ccccttccaa ctcaaccaac gggaccagct ggaaagggtc ctctttgacg    660
agctagggct tcccgccatc ggcaagacgg agaagaccgg caagcgctcc accagcgccg    720
ccgtcctgga ggccctccgc gaggccacc ccatcgtgga aagatcctg cagtaccggg      780
agctcaacaa gctgaagagc acccaaatta ctcagttgcc ggacctcatc accccaggag    840
cgggccgcct ccacacccgc ttcaaccaga cggccacgca aacgggcagg ctaagtagct    900
cccagcccaa cctccagaac atccccgtcc gcacccccgct tgggcagagg atccgccgga    960
ccttcatcgc cgaggagggg aggctattgg tggccctgga ctataaccag atagagctca   1020
gggtgctggc ccacctctcc ggcgacgaga acctgatccg ggtcttccag gaggggcggg   1080
acatccacac ggagaccgcc agctggatgt tcggcgtccc ccgggaggcc gtggaccccc   1140
```

-continued

```
tgatgcgccg gcggccaag accatcaact tcggggtcct ctacggcatg tcggcccacc    1200
gcctctccca ggagctagcc atcccttacg aggaggccca ggccttcatt gagcgctact    1260
ttcagagctt ccccaaggtg cgggcctgga ttgagaagac cctggaggag gcaggaggc    1320 gggggtacgt ggagaccctc ttcggccgcc gccgctacct gccagaccta gaggcccagg    1380
tgaagaatgt gcgggaggcg gccgagcgca gggccttcaa catgcccgtc cagggcaccg    1440
ccgccgacct catgaagctg gctatggtga agctcttccc caggctggag gaaatggggg    1500
ccaggatgct ccttcaggtc cacgacgagc tggtcctcga ggccccaaaa gaggggcgg    1560 aggccgtggc ccggctggcc aaggaggtca tgggggggt gtatccctg ccgtgcctc      1620 tggaggtgga ggtggggata ggggaggact ggctctccgc caaggaggcg ccgcactgg    1680 tgccgcgc                                                             1688
```

<210> SEQ ID NO 24
<211> LENGTH: 562
<212> TYPE: PRT
<213> ORGANISM: Thermus aquaticus

<400> SEQUENCE: 24

```
Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Gln Leu Asn
        195                 200                 205

Gln Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Asn Lys Leu Lys Ser Thr Gln Ile Thr Gln Leu
            260                 265                 270
```

```
Pro Asp Leu Ile His Pro Arg Thr Gly Arg Leu His Thr Arg Phe Asn
        275                 280                 285

Gln Thr Ala Thr Gln Thr Gly Arg Leu Ser Ser Gln Pro Asn Leu
        290                 295                 300

Gln Asn Ile Pro Val Arg Thr Pro Leu Gly Gln Arg Ile Arg Arg Thr
305                 310                 315                 320

Phe Ile Ala Glu Glu Gly Arg Leu Leu Val Ala Leu Asp Tyr Asn Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
            435                 440                 445

Arg Arg Arg Tyr Leu Pro Asp Leu Glu Ala Gln Val Lys Asn Val Arg
450                 455                 460

Glu Ala Ala Glu Arg Arg Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
            515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Ala Ala Ala Leu Val
545                 550                 555                 560

Pro Arg

<210> SEQ ID NO 25
<211> LENGTH: 1688
<212> TYPE: DNA
<213> ORGANISM: Thermus aquaticus

<400> SEQUENCE: 25
ccatggcctc tggtggcggt ggctgtggtg gcggtggcag ccccaaggcc ctggaggagg      60
ccccctggcc cccgccggaa ggggccttcg tgggctttgt gctttcccgc aaggagccca     120
tgtgggccga tcttctggcc ctggccgccg caggggggg ccgggtccac cgggcccccg     180
agccttataa agccctcagg gacctgaagg aggcgcgggg gcttctcgcc aaagacctga     240
gcgttctggc cctgagggaa ggccttggcc tcccgcccgg cgacgacccc atgctcctcg     300
cctacctcct ggacccttcc aacaccaccc cgaggggggt ggcccggcgc tacggcgggg     360
agtggacgga ggaggcgggg gagcggccg cccttttccga gaggctcttc gccaacctgt     420
gggggaggct tgagggggag gagaggctcc tttggcttta ccgggaggtg gagaggcccc     480
```

-continued

```
tttccgctgt cctggcccac atggaggcca cggggtgcg cctggacgtg gcctatctca      540
gggccttgtc cctggaggtg gccgaggaga tcgcccgcct cgaggccgag gtcttccgcc      600
tggccggcca ccccttcaac ctcaactccc gggaccagct ggaaagggtc ctctttgacg      660
agctagggct tcccgccatc ggcaagacgg agaagaccgg caagcgctcc accagcgccg      720
ccgtcctgga ggcctccgc gaggcccacc ccatcgtgga aagatcctg cagtaccggg       780
agctcaccaa gctgaagagc acctacattg accccttgcc ggacctcatc caccccagga      840
cgggccgcct ccacacccgc ttcaaccaga cggccacggc cacgggcagg ctaagtagct      900
ccgatcccaa cctccagaac atccccgtcc gcaccccgct gggcagagg atccgccggg      960
ccttcatcgc cgaggagggg tggctattgg tggccctgga ctatagccag atagagctca     1020
gggtgctggc ccacctctcc ggcgacgaga acctgatccg ggtcttccag gaggggcggg     1080
acatccacac ggagaccgcc agctggatgt tcggcgtccc ccgggaggcc gtggaccccc     1140
tgatgcgccg ggcggccaag accatcaact tcggggtcct ctacggcatg tcggcccacc     1200
gcctctccca ggagctagcc atcccttacg aggaggccca ggccttcatt gagcgctact     1260
ttcagagctt ccccaaggtg cgggcctgga ttgagaagac cctggaggag ggcaggaggc     1320
gggggtacgt ggagaccctc ttcggccgcc gccgctacgt gccagaccta gaggcccggg     1380
tgaagagcgt gcgggaggcg gccgagcgca tggccttcaa catgcccgtc agggcaccg     1440
ccgccgacct catgaagctg gctatggtga agctcttccc caggctggag gaaatggggg     1500
ccaggatgct ccttcaggtc cacgacgagc tggtcctcga ggccccaaaa gagagggcg     1560
aggccgtggc ccggctggcc aaggaggtca tggagggggt gtatcccctg ccgtgcccc     1620
tggaggtgga ggtggggata ggggaggact ggctctccgc caaggaggcg gccgcactgg     1680
tgccgcgc                                                              1688
```

<210> SEQ ID NO 26
<211> LENGTH: 562
<212> TYPE: PRT
<213> ORGANISM: Thermus aquaticus

<400> SEQUENCE: 26

```
Met Ala Ser Gly Gly Gly Cys Gly Gly Gly Ser Pro Lys Ala
1               5                  10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
```

```
                145                 150                 155                 160
        Ser Ala Val Leu Ala His Met Glu Ala Thr Gly Val Arg Leu Asp Val
                        165                 170                 175

Ala Tyr Leu Arg Ala Leu Ser Leu Glu Val Ala Glu Ile Ala Arg
                    180                 185                 190

Leu Glu Ala Glu Val Phe Arg Leu Ala Gly His Pro Phe Asn Leu Asn
                    195                 200                 205

Ser Arg Asp Gln Leu Glu Arg Val Leu Phe Asp Glu Leu Gly Leu Pro
                210                 215                 220

Ala Ile Gly Lys Thr Glu Lys Thr Gly Lys Arg Ser Thr Ser Ala Ala
        225                 230                 235                 240

Val Leu Glu Ala Leu Arg Glu Ala His Pro Ile Val Glu Lys Ile Leu
                        245                 250                 255

Gln Tyr Arg Glu Leu Thr Lys Leu Lys Ser Thr Tyr Ile Asp Pro Leu
                    260                 265                 270

Pro Asp Leu Ile His Pro Arg Thr Gly Arg Leu His Thr Arg Phe Asn
                    275                 280                 285

Gln Thr Ala Thr Ala Thr Gly Arg Leu Ser Ser Ser Asp Pro Asn Leu
                290                 295                 300

Gln Asn Ile Pro Val Arg Thr Pro Leu Gly Gln Arg Ile Arg Arg Ala
        305                 310                 315                 320

Phe Ile Ala Glu Glu Gly Trp Leu Leu Val Ala Leu Asp Tyr Ser Gln
                        325                 330                 335

Ile Glu Leu Arg Val Leu Ala His Leu Ser Gly Asp Glu Asn Leu Ile
                    340                 345                 350

Arg Val Phe Gln Glu Gly Arg Asp Ile His Thr Glu Thr Ala Ser Trp
                    355                 360                 365

Met Phe Gly Val Pro Arg Glu Ala Val Asp Pro Leu Met Arg Arg Ala
                370                 375                 380

Ala Lys Thr Ile Asn Phe Gly Val Leu Tyr Gly Met Ser Ala His Arg
        385                 390                 395                 400

Leu Ser Gln Glu Leu Ala Ile Pro Tyr Glu Glu Ala Gln Ala Phe Ile
                        405                 410                 415

Glu Arg Tyr Phe Gln Ser Phe Pro Lys Val Arg Ala Trp Ile Glu Lys
                    420                 425                 430

Thr Leu Glu Glu Gly Arg Arg Arg Gly Tyr Val Glu Thr Leu Phe Gly
                    435                 440                 445

Arg Arg Arg Tyr Val Pro Asp Leu Glu Ala Arg Val Lys Ser Val Arg
                450                 455                 460

Glu Ala Ala Glu Arg Met Ala Phe Asn Met Pro Val Gln Gly Thr Ala
        465                 470                 475                 480

Ala Asp Leu Met Lys Leu Ala Met Val Lys Leu Phe Pro Arg Leu Glu
                        485                 490                 495

Glu Met Gly Ala Arg Met Leu Leu Gln Val His Asp Glu Leu Val Leu
                    500                 505                 510

Glu Ala Pro Lys Glu Arg Ala Glu Ala Val Ala Arg Leu Ala Lys Glu
                    515                 520                 525

Val Met Glu Gly Val Tyr Pro Leu Ala Val Pro Leu Glu Val Glu Val
                530                 535                 540

Gly Ile Gly Glu Asp Trp Leu Ser Ala Lys Glu Ala Ala Leu Val
        545                 550                 555                 560

Pro Arg
```

<210> SEQ ID NO 27
<211> LENGTH: 1688
<212> TYPE: DNA
<213> ORGANISM: Thermus aquaticus

<400> SEQUENCE: 27

```
ccatggcctc tggtggcggt ggctgtggtg gcggtggcag ccccaaggcc ctggaggagg      60
cccccctggcc ccgccggaa ggggccttcg tgggctttgt gctttccgc aaggagccca     120
tgtgggccga tcttctggcc ctggccgccg ccagggggg ccgggtccac cgggcccccg     180
agccttataa agccctcagg gacctgaagg aggcgcgggg gcttctcgcc aaagacctga    240
gcgttctggc cctgagggaa ggccttggcc tcccgcccgg cgacgacccc atgctcctcg    300
cctacctcct ggaccttcc aacaccaccc ccgaggggg ggcccggcgc tacgcgggg      360
agtggacgga ggaggcgggg gagcgggccg cccttccga gaggctcttc gccaacctgt    420
ggggaggct tgaggggag gagaggctcc tttggcttta ccgggaggtg gagaggcccc     480
tttccgctgt cctggcccac atggaggcca cggggtgcg cctggacgtg gcctatctca    540
gggccttgtc cctggaggtg gccgaggaga tcgcccgcct cgaggccgag gtcttccgcc    600
tggccggcca ccccttcaac ctcaactccc gggaccagct ggaaagggtc ctctttgacg    660
agctagggct tcccgccatc ggcaagacgg agaagaccgg caagcgctcc accagcgccg    720
tcgtcctgga ggccctccgc gaggcccacc ccatcgtgga agatcctg cagtaccggg      780
agctcaccaa gctgaagagc acctacattg accccttgcc ggacctcatc caccccagga    840
cgggccgcct ccacacccgc ttcaaccaga cggccacggc cacgggcagg ctaagtagct    900
ccgatcccaa cctccagaac atccccgtcc gcaccccgt tgggcagagg atccgccggg    960
ccttcatcgc cgaggagggg tggctattgg tggccctgga ctatagccag atagagctca   1020
gggtgctggc ccacctctcc ggcgacgaga acctgatccg gtcttccag gaggggcggg    1080
acatccacac ggagaccgcc agctggatgt tcggcgtccc ccgggaggcc gtggaccccc   1140
tgatgcgccg ggcggccaag agcatcaact tcgggtcct ctacggcatg tcggcccacc    1200
gcctctccca ggagctagcc atcccttacg aggaggccca ggccttcatt gagcgctact   1260
ttcagagctt ccccaaggtg cgggcctgga ttgagaagac cctggaggag gcaggaggc    1320
gggggtacgt ggagaccctc ttcggccgcc gcgctacgt gccagaccta gaggcccggg   1380
tgaagagcgt gcgggaggcg gccgagcgca tggccttcaa catgcccgtc cagggcaccg   1440
ccgccgacct catgaagctg gctatggtga agctctcccc caggctggag gaaatggggg   1500
ccaggatgct ccttcaggtc cacgacgagc tggtcctcga ggccccaaaa gagggggcgg   1560
aggccgtggc ccggctggcc aaggaggtca tgagggggt gtatcccctg ccgtgcccc   1620
tggaggtgga ggtggggata ggggaggacc ggctctccgc caaggaggcg gccgcactgg   1680
tgccgcgc                                                             1688
```

<210> SEQ ID NO 28
<211> LENGTH: 562
<212> TYPE: PRT
<213> ORGANISM: Thermus aquaticus

<400> SEQUENCE: 28

Met Ala Ser Gly Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

-continued

Val Leu Ser Arg Lys Glu Pro Met Trp Ala Asp Leu Leu Ala Leu Ala
        35                  40                  45

Ala Ala Arg Gly Gly Arg Val His Arg Ala Pro Glu Pro Tyr Lys Ala
 50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
            130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
            210                 215                 220

Ala Ile Gly Lys Thr Glu Lys Thr Gly Lys Arg Ser Thr Ser Ala Val
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Ser Asp Pro Asn Leu
            290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
            370                 375                 380

Ala Lys Ser Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
            435                 440                 445

-continued

```
Arg Arg Arg Tyr Val Pro Asp Leu Glu Ala Arg Val Lys Ser Val Arg
    450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Ser Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Arg Leu Ser Ala Lys Glu Ala Ala Ala Leu Val
545                 550                 555                 560

Pro Arg
```

<210> SEQ ID NO 29
<211> LENGTH: 1688
<212> TYPE: DNA
<213> ORGANISM: Thermus aquaticus

<400> SEQUENCE: 29

| | |
|---|---:|
| ccatggcctc tggtggcggt ggctgtggtg gcggtggcag ccccaaggcc ctggaggagg | 60 |
| cccccctggcc cccgccggaa ggggccttcg tgggctttgt gctttccgc aaggagccca | 120 |
| tgtgggccga tcttctggcc ctggccgccg ccaggggggg ccgggtccac cgggcccccg | 180 |
| agccttataa agccctcagg gacctgaagg aggcgcgggg gcttctcgcc aaagacctga | 240 |
| gcgttctggc cctgagggaa ggccttggcc tcccgcccgg cgacgacccc atgctcctcg | 300 |
| cctacctcct ggacccttcc aacaccaccc cgaggggggt ggcccggcgc tacggcgggg | 360 |
| agtggacgga ggaggcgggg gagcgggccg cccttccga ggctcttc gccaacctgt | 420 |
| gggggaggct tgaggggag gagaggctcc tttggcttta ccggaggtg gagaggcccc | 480 |
| tttccgctgt cctggcccac atggaggcca cgggggtgcg cctggacgtg gcctatctca | 540 |
| gggccttgtc cctggaggtg gccgaggaga tcgcccgcct cgaggccgag gtcttccgcc | 600 |
| tggccggcca ccccttcaac ctcaactccc ggaccagct ggaaagggtc ctctttgacg | 660 |
| agctagggct tcccgccatc ggcaagacgg agaagaccgg caagcgctcc accagcgccg | 720 |
| ccgtcctgga ggccctccgc gaggccaccc catcgtgga agatcctg cagtaccggg | 780 |
| agctcaccaa gctgaagagc acctacattg acccccttgcc ggacctcatc caccccagga | 840 |
| cgggccgcct ccacacccgc ttcaaccaga cggtcacggc cacgggcagg ctaagtagct | 900 |
| ccgatcccaa cctccagaac atccccgtcc gcaccccgct gggcagagg atccgccggg | 960 |
| ccttcatcgc cgaggagggg tggctattgg tggccctgga ctatagccag atagagctca | 1020 |
| gggtgctggc ccacctctcc ggcgacgaga acctgatccg ggtcttccag gaggggcggg | 1080 |
| acatccacac ggagaccgcc agctggatgt tcggcgtccc ccgggaggcc gtggacccccc | 1140 |
| tgatgcgccg ggcggccaag accatcaact tcggggtcct ctacggcatg tcggcccacc | 1200 |
| gcctctccca ggagctagcc atcccttacg aggaggccca ggccttcatt gagcgctact | 1260 |
| ttcagagctt ccccaaggtg cgggcctgga ttgagaagac cctggaggag gcaggaggc | 1320 |
| gggggtacgt ggagaccctc ttcggccgcc gcgctacgt gccagaccta gaggccgg | 1380 |
| tgaagagcgt gcgggaggcg gccgagcgca tggcctacaa catgcccgtc cagggcaccg | 1440 |

-continued

```
ccgccgacct catgaagctg gctatggtga agctcttccc caggctggag gaaatggggg    1500
ccaggatgct ccttcaggtc cacgacgagc tggtcctcga ggccccaaaa gaggggcgg     1560 aggccgtggc ccggctggcc aaggaggtca tggaggggt gtatcccctg ccgtgcccc     1620 tggaggtgga ggtggggata ggggaggact ggctctccgc caaggaggcg ccgcactgg    1680 tgccgcgc                                                              1688
```

```
<210> SEQ ID NO 30
<211> LENGTH: 562
<212> TYPE: PRT
<213> ORGANISM: Thermus aquaticus

<400> SEQUENCE: 30
```

| | | | | | | | | | | | | | | |
|---|---|---|---|---|---|---|---|---|---|---|---|---|---|---|
| Met | Ala | Ser | Gly | Gly | Gly | Cys | Gly | Gly | Gly | Ser | Pro | Lys | Ala |
| 1 | | | | 5 | | | | | 10 | | | | | 15 |
| Leu | Glu | Glu | Ala | Pro | Trp | Pro | Pro | Glu | Gly | Ala | Phe | Val | Gly | Phe |
| | | | 20 | | | | | 25 | | | | | 30 | |
| Val | Leu | Ser | Arg | Lys | Glu | Pro | Met | Trp | Ala | Asp | Leu | Leu | Ala | Leu | Ala |
| | | | | 35 | | | | | 40 | | | | | 45 | |
| Ala | Ala | Arg | Gly | Gly | Arg | Val | His | Arg | Ala | Pro | Glu | Pro | Tyr | Lys | Ala |
| | 50 | | | | | 55 | | | | | 60 | | | | |
| Leu | Arg | Asp | Leu | Lys | Glu | Ala | Arg | Gly | Leu | Leu | Ala | Lys | Asp | Leu | Ser |
| 65 | | | | | 70 | | | | | 75 | | | | | 80 |
| Val | Leu | Ala | Leu | Arg | Glu | Gly | Leu | Gly | Leu | Pro | Pro | Gly | Asp | Asp | Pro |
| | | | | 85 | | | | | 90 | | | | | 95 | |
| Met | Leu | Leu | Ala | Tyr | Leu | Leu | Asp | Pro | Ser | Asn | Thr | Thr | Pro | Glu | Gly |
| | | | 100 | | | | | 105 | | | | | 110 | | |
| Val | Ala | Arg | Arg | Tyr | Gly | Gly | Glu | Trp | Thr | Glu | Glu | Ala | Gly | Glu | Arg |
| | | | | 115 | | | | | 120 | | | | | 125 | |
| Ala | Ala | Leu | Ser | Glu | Arg | Leu | Phe | Ala | Asn | Leu | Trp | Gly | Arg | Leu | Glu |
| | 130 | | | | | 135 | | | | | 140 | | | | |
| Gly | Glu | Glu | Arg | Leu | Leu | Trp | Leu | Tyr | Arg | Glu | Val | Glu | Arg | Pro | Leu |
| 145 | | | | | 150 | | | | | 155 | | | | | 160 |
| Ser | Ala | Val | Leu | Ala | His | Met | Glu | Ala | Thr | Gly | Val | Arg | Leu | Asp | Val |
| | | | | 165 | | | | | 170 | | | | | 175 | |
| Ala | Tyr | Leu | Arg | Ala | Leu | Ser | Leu | Glu | Val | Ala | Glu | Glu | Ile | Ala | Arg |
| | | | 180 | | | | | 185 | | | | | 190 | | |
| Leu | Glu | Ala | Glu | Val | Phe | Arg | Leu | Ala | Gly | His | Pro | Phe | Asn | Leu | Asn |
| | | | | 195 | | | | | 200 | | | | | 205 | |
| Ser | Arg | Asp | Gln | Leu | Glu | Arg | Val | Leu | Phe | Asp | Glu | Leu | Gly | Leu | Pro |
| | 210 | | | | | 215 | | | | | 220 | | | | |
| Ala | Ile | Gly | Lys | Thr | Glu | Lys | Thr | Gly | Lys | Arg | Ser | Thr | Ser | Ala | Ala |
| 225 | | | | | 230 | | | | | 235 | | | | | 240 |
| Val | Leu | Glu | Ala | Leu | Arg | Glu | Ala | His | Pro | Ile | Val | Glu | Lys | Ile | Leu |
| | | | | 245 | | | | | 250 | | | | | 255 | |
| Gln | Tyr | Arg | Glu | Leu | Thr | Lys | Leu | Lys | Ser | Thr | Tyr | Ile | Asp | Pro | Leu |
| | | | 260 | | | | | 265 | | | | | 270 | | |
| Pro | Asp | Leu | Ile | His | Pro | Arg | Thr | Gly | Arg | Leu | His | Thr | Arg | Phe | Asn |
| | | | | 275 | | | | | 280 | | | | | 285 | |
| Gln | Thr | Val | Thr | Ala | Thr | Gly | Arg | Leu | Ser | Ser | Ser | Asp | Pro | Asn | Leu |
| | 290 | | | | | 295 | | | | | 300 | | | | |
| Gln | Asn | Ile | Pro | Val | Arg | Thr | Pro | Leu | Gly | Gln | Arg | Ile | Arg | Arg | Ala |
| 305 | | | | | 310 | | | | | 315 | | | | | 320 |
| Phe | Ile | Ala | Glu | Glu | Gly | Trp | Leu | Leu | Val | Ala | Leu | Asp | Tyr | Ser | Gln |

```
                       325                 330                 335
Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
            355                 360                 365

Met Phe Gly Val Pro Arg Glu Ala Val Asp Pro Leu Met Arg Arg Ala
        370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
    450                 455                 460

Glu Ala Ala Glu Arg Met Ala Tyr Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
        515                 520                 525

Val Met Glu Gly Val Tyr Pro Leu Ala Val Pro Leu Glu Val Glu Val
    530                 535                 540

Gly Ile Gly Glu Asp Trp Leu Ser Ala Lys Glu Ala Ala Leu Val
545                 550                 555                 560
Pro Arg

<210> SEQ ID NO 31
<211> LENGTH: 1688
<212> TYPE: DNA
<213> ORGANISM: Thermus aquaticus

<400> SEQUENCE: 31
ccatggcctc tggtggcggt ggctgtggtg gcggtggcag ccccaaggcc ctggaggagg    60 cccctggcc ccgccggaa ggggccttcg tgggctttgt gctttccgc aaggagccca     120 tgtgggccga tcttctggcc ctggccgccg caggggggg ccgggtccac cgggccccg    180 agccttataa agccctcagg gacctgaagg aggcgcgggg gcttctcgcc aaagacctga    240
gcgttctggc cctgagggaa ggccttggcc tcccgcccgg cgacgacccc atgctcctcg    300
cctacctcct ggacccttcc aacaccaccc cgagggggt ggcccggcgc tacggcgggg    360
agtggacgga ggaggcgggg gagcgggccg cccttccga gaggctcttc gccaacctgt    420
gggggaggct tgaggggag gagaggctcc tttggcttta ccgggaggtg gagaggcccc    480
tttccgctgt cctggcccac atggaggcca cggggtgcg cctggacgtg gcctatctca    540
gggccttgtc cctggaggtg gccgaggaga tcgcccgcct cgaggccgag gtcttccgcc    600
tggccggcca ccccttcaac ctcaactccc gggaccagct ggaaagggtc tcctttgacg    660
agctaggggc tcccgccatc ggcaagacgg agaagaccgg caagcgctcc accagcgccg    720
ccgtcctgga ggccctccgc gaggcccacc ccatcgtgga gaagatcctg cagtaccggg    780
```

-continued

```
agctcaccaa gctgaagagc acctacattg accccttgcc ggacctcatc caccccagga    840
cgggccgcct ccacacccgc ttcaaccaga cggccacggc cacgggcagg ctaagtagct    900
ccgatcccaa cctccagaac atccccgtcc gcaccccgct tgggcagagg atccgccggg    960
ccttcatcgc cgaggagggg tggctattgg tggccctgga ctatagccag atagagctca   1020
gggtgctggc ccacctctcc ggcgacgaga acctgatccg ggtcttccag gaggggcggg   1080
acatccacac ggagaccgcc agctggatgt cggcgtcccc cgggaggcc gtggaccccc    1140
tgatgcgccg ggcggccaag accatcaact tcggggtcct ctacggcatg tcggcccacc   1200
gcctctccca ggagctagcc atcccttacg aggaggccca ggccttcatt gagcgctact   1260
ttcagagctt ccccaaggtg cgggcctgga ttgagaagac cctggaggag gcaggaggc    1320
gggggtacgt ggagaccctc ttcggccgcc gccgctacgt gccagaccta gaggcccggg   1380
tgaagagcgt gcgggaggcg ccgagcgca tggccttcaa catgcccgtc agggcaccg     1440
ccgccgacct catgaagctg ctatggtga agctcttccc caggctggag gaaatggggg    1500
ccaggatgct ccttcaggtc cacgacgagc tggtcctcga ggccccaaaa gaggggcgg    1560
aggccgtggc ccggctggcc aaggaggtca tggaggggt gtatcccctg gccgtgcccc    1620
tggaggtgga ggtggggata ggggaggacc ggctctccgc caaggaggcg ccgcactgg    1680
tgccgcgc                                                           1688
```

<210> SEQ ID NO 32
<211> LENGTH: 562
<212> TYPE: PRT
<213> ORGANISM: Thermus aquaticus

<400> SEQUENCE: 32

```
Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu Ala
        35                  40                      45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205
```

Ser Arg Asp Gln Leu Glu Arg Val Leu Phe Asp Glu Leu Gly Leu Pro
210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
            245                 250                 255

Gln Tyr Arg Glu Leu Thr Lys Leu Lys Ser Thr Tyr Ile Asp Pro Leu
        260                 265                 270

Pro Asp Leu Ile His Pro Arg Thr Gly Arg Leu His Thr Arg Phe Asn
    275                 280                 285

Gln Thr Ala Thr Ala Thr Gly Arg Leu Ser Ser Asp Pro Asn Leu
290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
            325                 330                 335

Ile Glu Leu Arg Val Leu Ala His Leu Ser Gly Asp Glu Asn Leu Ile
        340                 345                 350

Arg Val Phe Gln Glu Gly Arg Asp Ile His Thr Glu Thr Ala Ser Trp
    355                 360                 365

Met Phe Gly Val Pro Arg Glu Ala Val Asp Pro Leu Met Arg Arg Ala
370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
            405                 410                 415

Glu Arg Tyr Phe Gln Ser Phe Pro Lys Val Arg Ala Trp Ile Glu Lys
        420                 425                 430

Thr Leu Glu Glu Gly Arg Arg Arg Gly Tyr Val Glu Thr Leu Phe Gly
    435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Met Lys Leu Ala Met Val Lys Leu Phe Pro Arg Leu Glu
            485                 490                 495

Glu Met Gly Ala Arg Met Leu Leu Gln Val His Asp Glu Leu Val Leu
        500                 505                 510

Glu Ala Pro Lys Glu Gly Ala Glu Ala Val Ala Arg Leu Ala Lys Glu
    515                 520                 525

Val Met Glu Gly Val Tyr Pro Leu Ala Val Pro Leu Glu Val Glu Val
530                 535                 540

Gly Ile Gly Glu Asp Arg Leu Ser Ala Lys Glu Ala Ala Ala Leu Val
545                 550                 555                 560

Pro Arg

<210> SEQ ID NO 33
<211> LENGTH: 1688
<212> TYPE: DNA
<213> ORGANISM: Thermus aquaticus

<400> SEQUENCE: 33
ccatggcctc tggtggcggt ggctgtggtg gcggtggcag ccccaaggcc ctggaggagg    60

```
cccccctggcc ccgccggaa gggggccttcg tgggctttgt gctttcccgc aaggagccca      120
tgtgggccga tcttctggcc ctggccgccg ccagggggg ccgggtccac cgggcccccg       180
agccttataa agccctcagg gacctgaagg aggcgcgggg gcttctcgcc aaagacctga      240
gcgttctggc cctgagggaa ggccttggcc tcccgcccgg cgacgacccc atgctcctcg      300
cctacctcct ggaccccttcc aacaccacccc ccgaggggt ggcccggcgc tacggcgggg    360
agtggacgga ggaggcgggg gagcgggccg ccctttccga gaggctcttc gccaacctgt      420
ggggaggct tgaggggag gagaggctcc tttggcttta ccgggaggtg gagaggcccc        480
tttccgctgt cctggcccac atggaggcca cggggggtgcg cctggacgtg gcctatctca    540
gggccttgtc cctggaggtg gccgaggaga tcgcccgcct cgaggccgag gtcttccgcc     600
tggccggcca cccttcaac ctcaactccc ggaccagct ggaaagggtc ctctttgacg        660
agctagggct tcccgccatc ggcaagacgg agaagaccgg caagcgctcc accagcgccg    720
ccgtcctgga ggccctccgc gaggcccacc ccatcgtgga aagatcctg cagtaccggg      780
agctcaccaa gctgaagagc acctacattg accccttgcc ggacctcatc caccccagga   840
cgggccgcct ccacacccgc ttcaaccaga cggccacggc cacgggcagg ctaagtagct    900
ccgatcccaa cctccagaac atccccgtcc gcaccccgct gggcagagg atccgccggg      960
ccttcatcgc cgaggagggg tggctattgg tggccctgga ctatagccag atagagctca   1020
gggtgctggc ccacctctcc ggcgacgaga acctgatccg ggtcttccag gaggggcggg   1080
acatccacac ggagaccgcc agctggatgt tcggcgtccc ccgggaggcc gtggaccccc   1140
tgatgcgccg ggcggccaag accatcaact tcggggtcct ctacggcatg tcggcccacc   1200
gcctctccca ggagctagcc atcccttacg aggaggccca ggccttcatt gagcgctact   1260
ttctgagctt ccccaaggtg cgggcctgga ttgagaagac cctggaggag gcaggaggc    1320
ggggtacgt ggagaccctc ttcggccgcc gcgctacgt gccagaccta gaggcccggg    1380
tgaagagcgt gcgggaggcg ccgagcgca aggccttcaa catgcccgtc cagggcaccg    1440
ccgccgacct catgaagctg gctatggtga agctcttccc caggctggag gaaatggggg   1500
ccaggatgct ccttcaggtc cacgacgagc tggtcctcga ggccccaaaa gaggggcgg     1560
aggccgtggc ccggctggcc aaggaggtca tggggggggt gtatccctg gccgtgctcc     1620
tggaggtgga ggtggggata ggggaggact ggctctccgc caaggaggcg gccgcactgg   1680
tgccgcgc                                                                                1688

<210> SEQ ID NO 34
<211> LENGTH: 562
<212> TYPE: PRT
<213> ORGANISM: Thermus aquaticus

<400> SEQUENCE: 34

Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
            20                  25                  30

Val Leu Ser Arg Lys Glu Pro Met Trp Ala Asp Leu Leu Ala Leu
        35                  40                  45

Ala Ala Arg Gly Gly Arg Val His Arg Ala Pro Glu Pro Tyr Lys Ala
    50                  55                  60

Leu Arg Asp Leu Lys Glu Ala Arg Gly Leu Leu Ala Lys Asp Leu Ser
65                  70                  75                  80
```

```
Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
        115                 120                 125

Ala Ala Leu Ser Glu Arg Leu Phe Ala Asn Leu Trp Gly Arg Leu Glu
    130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Pro Asp Leu Ile His Pro Arg Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
    370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Leu Ser Phe Pro Lys Val Arg Ala Trp Ile Glu Lys
            420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Val Arg
    450                 455                 460

Glu Ala Ala Glu Arg Lys Ala Phe Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
```

```
                500              505              510
        Glu Ala Pro Lys Glu Gly Ala Glu Ala Val Ala Arg Leu Ala Lys Glu
                    515                  520                  525

Val Met Glu Gly Val Tyr Pro Leu Ala Val Leu Leu Glu Val Glu Val
                    530                  535                  540

Gly Ile Gly Glu Asp Trp Leu Ser Ala Lys Glu Ala Ala Ala Leu Val
        545                  550                  555                  560

Pro Arg

<210> SEQ ID NO 35
<211> LENGTH: 1688
<212> TYPE: DNA
<213> ORGANISM: Thermus aquaticus

<400> SEQUENCE: 35
ccatggcctc tggtggcggt ggctgtggtg gcggtggcag ccccaaggcc ctggaggagg      60
ccccctggcc ccgccggaa ggggccttcg tgggctttgt gctttccgc aaggagccca      120 tgtgggccga tcttctggcc ctggccgccg ccagggggg ccgggtccac cgggcccccg      180
agccttataa agccctcagg gacctgaagg aggcgcgggg gcttctcgcc aaagacctga      240
gcgttctggc cctgagggaa ggccttggcc tcccgcccgg cgacgacccc atgctcctcg      300
cctacctcct ggaccctccc aacaccaccc ccgaggggt ggcccggcgc tacggcgggg      360
agtggacgga ggaggcgggg gagcgggccc cctttccga gaggctcttc gccaacctgt      420
gggggaggct tgagggggag gagaggctcc tttggcttta ccgggaggtg gagaggcccc      480
tttccgctgt cctggcccac atggaggcca cggggtgcg cctggacgtg gcctatctca      540
gggccttgtc cctggaggtg gccgaggaga tcgcccgcct cgaggccgag gtcttccgcc      600
tggccggcca ccccttcaac ctcaactccc gggaccagct ggaaagggtc ctctttgacg      660
agctagggct tcccgccatc ggcaagacgg agaagaccgg caagcgctcc accagcgccg      720
ccgtcctgga ggccctccgc gaggccaccc ccatcgtgga agatcctg cagtaccggg      780 agctcaccaa gctgaagagc acctacattg accccttgca ggacctcatc accccagta      840 cgggccgcct ccacacccgc ttcaaccaga cggccacggc cacgggcagg ctaagtagct      900
ccgatcccaa cctccagaac atccccgtcc gcacccccgt tgggcagagg atcgccgggg      960
ccttcatcgc cgaggagggg tggctattgg tggccctgga ctatagccag atagagctca     1020
gggtgctggc ccacctctcc ggcgacgaga acctgatccg ggtcttccag gaggggcggg     1080
acatccacac ggagaccgcc agctggatgt tcggcgtccc ccgggaggcc gtggaccccc     1140
tgatgcgccg ggcggccaag accatcaact tcgggtcct ctacggcatg tcggcccacc     1200
gcctctccca ggagctagcc atcccttacg aggaggccca ggccttcatt gagcgctact     1260
ttcagagctt ccccaaggtg cgggcctgga ttgagaagac cctagaggag gcaggaggc     1320 gggggtacgt ggagaccctc ttcggccgcc gccgctacgt gccagaccta gaggcccggg     1380
tgaagagcga gcgggaggcg gccgagcgca tggcctacaa catgcccgtc cagggcaccg     1440
ccgccgacct catgaagctg gctatggtga agctcttccc caggctggag gaaatggggg     1500
cccggatgct ccttcaggtc cacgacgagc tggtcctcga ggccccaaaa gagggggcgg     1560
aggccgtggc ccggctggcc aaggaggtca tggagggggt gtatcccctg gccgtgcccc     1620
tggaggcgga ggtggggata ggggaggatt ggctctccgc caaggaggcg gccgcactgg     1680
tgccgcgc                                                             1688
```

<210> SEQ ID NO 36
<211> LENGTH: 562
<212> TYPE: PRT
<213> ORGANISM: Thermus aquaticus

<400> SEQUENCE: 36

```
Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
                35                  40                  45

Ala Ala Arg Gly Gly Arg Val His Arg Ala Pro Glu Pro Tyr Lys Ala
            50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
            100                 105                 110

Val Ala Arg Arg Tyr Gly Gly Glu Trp Thr Glu Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
            180                 185                 190

Leu Glu Ala Glu Val Phe Arg Leu Ala Gly His Pro Phe Asn Leu Asn
        195                 200                 205

Ser Arg Asp Gln Leu Glu Arg Val Leu Phe Asp Glu Leu Gly Leu Pro
    210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255

Gln Tyr Arg Glu Leu Thr Lys Leu Lys Ser Thr Tyr Ile Asp Pro Leu
            260                 265                 270

Gln Asp Leu Ile His Pro Ser Thr Gly Arg Leu His Thr Arg Phe Asn
        275                 280                 285

Gln Thr Ala Thr Ala Thr Gly Arg Leu Ser Ser Ser Asp Pro Asn Leu
    290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
            340                 345                 350

Arg Val Phe Gln Glu Gly Arg Asp Ile His Thr Glu Thr Ala Ser Trp
        355                 360                 365

Met Phe Gly Val Pro Arg Glu Ala Val Asp Pro Leu Met Arg Arg Ala
    370                 375                 380
```

```
Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
            405                 410                 415

Glu Arg Tyr Phe Gln Ser Phe Pro Lys Val Arg Ala Trp Ile Glu Lys
        420                 425                 430

Thr Leu Glu Glu Gly Arg Arg Arg Gly Tyr Val Glu Thr Leu Phe Gly
        435                 440                 445

Arg Arg Arg Tyr Val Pro Asp Leu Glu Ala Arg Val Lys Ser Glu Arg
        450                 455                 460

Glu Ala Ala Glu Arg Met Ala Tyr Asn Met Pro Val Gln Gly Thr Ala
465                 470                 475                 480

Ala Asp Leu Met Lys Leu Ala Met Val Lys Leu Phe Pro Arg Leu Glu
                485                 490                 495

Glu Met Gly Ala Arg Met Leu Leu Gln Val His Asp Glu Leu Val Leu
            500                 505                 510

Glu Ala Pro Lys Glu Gly Ala Glu Ala Val Ala Arg Leu Ala Lys Glu
        515                 520                 525

Val Met Glu Gly Val Tyr Pro Leu Ala Val Pro Leu Glu Ala Glu Val
        530                 535                 540

Gly Ile Gly Glu Asp Trp Leu Ser Ala Lys Glu Ala Ala Ala Leu Val
545                 550                 555                 560

Pro Arg

<210> SEQ ID NO 37
<211> LENGTH: 1688
<212> TYPE: DNA
<213> ORGANISM: Thermus aquaticus

<400> SEQUENCE: 37
ccatggcctc tggtggcggt ggctgtggtg gcggtggcag ccccaaggcc ctggaggagg    60
cccccctggc cccgccggaa ggggccttcg tgggctttgt gctttcccgc aaggagccca   120
tgtgggccga tcttctggcc ctggccgccg ccaggggggg ccgggtccac cgggcccccg   180
agccttataa agccctcagg gacctgaagg aggcgcgggg gcttctcgcc aaagacctga   240
gcgttctggc cctgagggaa ggccttggcc tcccgccccg cgacgacccc atgctcctcg   300
cctacctcct ggaccgttcc aacaccacce cgagggggt ggcccggcgc tacgcgggg    360
agtggacgga ggaggcgggg gagcggccg cccttccga gaggctcttc gccaacctgt    420
gggggaggct tgaggggag gagaggctcc tttggcttta ccgggaggtg agaggcccc     480
tttccgctgt cctggcccac atggaggcca cgggggtgcg cctggacgtg gcctatctca    540
gggccttgtc cctggaggtg gccgaggaga tcgcccgcct cgaggccgag gtcttccgcc    600
tggccggcca ccccttcaac ctcaactccc gggaccagct ggaaagggtc ctctttgacg    660
agctagggct tcccgccatc ggcaagacgg agaagaccgg caagcgctcc accagcgccg    720
ccgtcctgga ggcctccgc gagcccacc ccatcgtgga aagatcctg cagtaccggg      780
agctcaccaa gctgaagagc acctacattg acccttgcc ggacctcatc caccccagga    840
cgggccgcct ccacacccgc ttcaaccaga cggccacggc cacgggcagg ctaagtagct    900
ccgatcccaa cctccagaac atccccgtcc gcaccccgct gggcagagg atccgccggg    960
ccttcatcgc cgaggagggg tggctattgg tggccctgga ctatagccag atagagctca   1020
ggtgctggc ccacctctcc ggcgacgaga acctgatccg ggtcttccag gaggggcggg   1080
```

-continued

```
acatccacac ggagaccgcc agctggatgt tcggcgtccc ccggggaggcc gtggaccccc    1140 tgatgcgccg gcggccaag  accatcaact tcggggtcct ctacggcatg tcggcccacc     1200
gcctctccca ggagctagcc atcccttacg aggaggccca ggccttcatt gagcgctact    1260
ttcagagctt ccccaaggtg cgggcctgga ttgagaagac cctggaggag gcaggaggc    1320 gggggtacgt ggagaccctc ttcggccgcc gccgctacgt gccagaccta gaggcccggg    1380
tgaagagcgt gcgggaggcg gccgagcgca tggccttcaa catgcccgtc cagggcaccg    1440
ccgccgacct cgtgaagctg gctatggtga agctcttccc caggctggag gaaatgggg    1500 ccaggatgct ccttcaggtc cacgacgagc tggtcctcga ggccccaaaa gagggggcgg    1560
aggccgtggc ccggctggcc aaggaggtca tggaggggt gtatcccctg gccgtgcccc    1620
tggaggtgga ggtggggata ggggaggact ggctctccgc caaggaggcg gccgcactgg    1680
tgccgcgc                                                              1688
```

<210> SEQ ID NO 38
<211> LENGTH: 562
<212> TYPE: PRT
<213> ORGANISM: Thermus aquaticus

<400> SEQUENCE: 38

```
Met Ala Ser Gly Gly Gly Cys Gly Gly Gly Ser Pro Lys Ala
1               5                   10                  15

Leu Glu Glu Ala Pro Trp Pro Pro Glu Gly Ala Phe Val Gly Phe
                20                  25                  30

Val Leu Ser Arg Lys Glu Pro Met Trp Ala Asp Leu Leu Ala Leu Ala
            35                  40                  45

Ala Ala Arg Gly Gly Arg Val His Arg Ala Pro Glu Pro Tyr Lys Ala
        50                  55                  60

Leu Arg Asp Leu Lys Glu Ala Arg Gly Leu Leu Ala Lys Asp Leu Ser
65                  70                  75                  80

Val Leu Ala Leu Arg Glu Gly Leu Gly Leu Pro Pro Gly Asp Asp Pro
                85                  90                  95

Met Leu Leu Ala Tyr Leu Leu Asp Pro Ser Asn Thr Thr Pro Glu Gly
                100                 105                 110

Val Ala Arg Arg Tyr Gly Gly Glu Trp Thr Glu Ala Gly Glu Arg
            115                 120                 125

Ala Ala Leu Ser Glu Arg Leu Phe Ala Asn Leu Trp Gly Arg Leu Glu
        130                 135                 140

Gly Glu Glu Arg Leu Leu Trp Leu Tyr Arg Glu Val Glu Arg Pro Leu
145                 150                 155                 160

Ser Ala Val Leu Ala His Met Glu Ala Thr Gly Val Arg Leu Asp Val
                165                 170                 175

Ala Tyr Leu Arg Ala Leu Ser Leu Glu Val Ala Glu Glu Ile Ala Arg
                180                 185                 190

Leu Glu Ala Glu Val Phe Arg Leu Ala Gly His Pro Phe Asn Leu Asn
            195                 200                 205

Ser Arg Asp Gln Leu Glu Arg Val Leu Phe Asp Glu Leu Gly Leu Pro
        210                 215                 220

Ala Ile Gly Lys Thr Glu Lys Thr Gly Lys Arg Ser Thr Ser Ala Ala
225                 230                 235                 240

Val Leu Glu Ala Leu Arg Glu Ala His Pro Ile Val Glu Lys Ile Leu
                245                 250                 255
```

```
Gln Tyr Arg Glu Leu Thr Lys Leu Lys Ser Thr Tyr Ile Asp Pro Leu
                260                 265                 270

Pro Asp Leu Ile His Pro Arg Thr Gly Arg Leu His Thr Arg Phe Asn
            275                 280                 285

Gln Thr Ala Thr Ala Thr Gly Arg Leu Ser Ser Asp Pro Asn Leu
290                 295                 300

Gln Asn Ile Pro Val Arg Thr Pro Leu Gly Gln Arg Ile Arg Arg Ala
305                 310                 315                 320

Phe Ile Ala Glu Glu Gly Trp Leu Leu Val Ala Leu Asp Tyr Ser Gln
                325                 330                 335

Ile Glu Leu Arg Val Leu Ala His Leu Ser Gly Asp Glu Asn Leu Ile
                340                 345                 350

Arg Val Phe Gln Glu Gly Arg Asp Ile His Thr Glu Thr Ala Ser Trp
                355                 360                 365

Met Phe Gly Val Pro Arg Glu Ala Val Asp Pro Leu Met Arg Arg Ala
370                 375                 380

Ala Lys Thr Ile Asn Phe Gly Val Leu Tyr Gly Met Ser Ala His Arg
385                 390                 395                 400

Leu Ser Gln Glu Leu Ala Ile Pro Tyr Glu Glu Ala Gln Ala Phe Ile
                405                 410                 415

Glu Arg Tyr Phe Gln Ser Phe Pro Lys Val Arg Ala Trp Ile Glu Lys
                420                 425                 430

Thr Leu Glu Glu Gly Arg Arg Arg Gly Tyr Val Glu Thr Leu Phe Gly
                435                 440                 445

Arg Arg Arg Tyr Val Pro Asp Leu Glu Ala Arg Val Lys Ser Val Arg
450                 455                 460

Glu Ala Ala Glu Arg Met Ala Phe Asn Met Pro Val Gln Gly Thr Ala
465                 470                 475                 480

Ala Asp Leu Val Lys Leu Ala Met Val Lys Leu Phe Pro Arg Leu Glu
                485                 490                 495

Glu Met Gly Ala Arg Met Leu Leu Gln Val His Asp Glu Leu Val Leu
                500                 505                 510

Glu Ala Pro Lys Glu Gly Ala Glu Ala Val Ala Arg Leu Ala Lys Glu
                515                 520                 525

Val Met Glu Gly Val Tyr Pro Leu Ala Val Pro Leu Glu Val Glu Val
530                 535                 540

Gly Ile Gly Glu Asp Trp Leu Ser Ala Lys Glu Ala Ala Ala Leu Val
545                 550                 555                 560

Pro Arg

<210> SEQ ID NO 39
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 39

Met Ala Ser Gly Gly Gly Gly Cys Gly Gly Gly Gly
1               5                   10

<210> SEQ ID NO 40
<211> LENGTH: 17
<212> TYPE: PRT
<213> ORGANISM: Artificial Sequence
<220> FEATURE:
<223> OTHER INFORMATION: Synthetic Peptide
```

```
<400> SEQUENCE: 40

Ala Ala Ala Leu Val Pro Arg Gly Ser Leu Glu His His His His
1               5                   10                  15

His

<210> SEQ ID NO 41
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 41

Met Lys Tyr Leu Leu Pro Thr Ala Ala Ala Gly Leu Leu Leu Leu Ala
1               5                   10                  15

Ala Gln Pro Ala Met Ala
            20

<210> SEQ ID NO 42
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 42

Met Lys Thr Leu Leu Ala Met Val Leu Val Gly Leu Leu Leu Leu Pro
1               5                   10                  15

Pro Gly Pro Ser Met Ala
            20

<210> SEQ ID NO 43
<211> LENGTH: 22
<212> TYPE: PRT
<213> ORGANISM: Artificial Sequence
<220> FEATURE:
<223> OTHER INFORMATION: Synthetic Peptide

<400> SEQUENCE: 43

Met Arg Gly Leu Leu Ala Met Leu Val Ala Gly Leu Leu Leu Leu Pro
1               5                   10                  15

Ile Ala Pro Ala Met Ala
            20

<210> SEQ ID NO 44
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 44

Met Arg Arg Leu Leu Val Ile Ala Ala Gly Leu Leu Leu Leu Ala
1               5                   10                  15

Pro Pro Thr Met Ala
            20

<210> SEQ ID NO 45
<211> LENGTH: 33
<212> TYPE: DNA
<213> ORGANISM: Artificial Sequence
<220> FEATURE:
<223> OTHER INFORMATION: Synthetic DNA
```

<400> SEQUENCE: 45
gcggccgcac tggtgccgcg cggcagcctc gag        33

<210> SEQ ID NO 46
<211> LENGTH: 148
<212> TYPE: PRT
<213> ORGANISM: Homo sapiens

<400> SEQUENCE: 46

Ala Asp Gln Leu Thr Glu Glu Gln Ile Ala Glu Phe Lys Glu Ala Phe
1               5                   10                  15

Ser Leu Phe Asp Lys Asp Gly Asp Gly Thr Ile Thr Thr Lys Glu Leu
            20                  25                  30

Gly Thr Val Met Arg Ser Leu Gly Gln Asn Pro Thr Glu Ala Glu Leu
        35                  40                  45

Gln Asp Met Ile Asn Glu Val Asp Ala Asp Gly Asn Gly Thr Ile Asp
    50                  55                  60

Phe Pro Glu Phe Leu Thr Met Met Ala Arg Lys Met Lys Asp Thr Asp
65                  70                  75                  80

Ser Glu Glu Glu Ile Arg Glu Ala Phe Arg Val Phe Asp Lys Asp Gly
                85                  90                  95

Asn Gly Tyr Ile Ser Ala Ala Glu Leu Arg His Val Met Thr Asn Leu
            100                 105                 110

Gly Glu Lys Leu Thr Asp Glu Glu Val Asp Glu Met Ile Arg Glu Ala
        115                 120                 125

Asp Ile Asp Gly Asp Gly Gln Val Asn Tyr Glu Glu Phe Val Gln Met
    130                 135                 140

Met Thr Ala Lys
145

<210> SEQ ID NO 47
<211> LENGTH: 114
<212> TYPE: PRT
<213> ORGANISM: Artificial Sequence
<220> FEATURE:
<223> OTHER INFORMATION: Synthetic DNA

<400> SEQUENCE: 47

Gln Val Gln Leu Gln Gln Ser Gly Pro Glu Asp Val Lys Pro Gly Ala
1               5                   10                  15

Ser Val Lys Ile Ser Cys Lys Ala Ser Gly Tyr Thr Phe Thr Asp Tyr
            20                  25                  30

Tyr Met Asn Trp Val Lys Gln Ser Pro Gly Lys Gly Leu Glu Trp Ile
        35                  40                  45

Gly Asp Ile Asn Pro Asn Asn Gly Gly Thr Ser Tyr Asn Gln Lys Phe
    50                  55                  60

Lys Gly Arg Ala Thr Leu Thr Val Asp Lys Ser Ser Thr Ala Tyr
65                  70                  75                  80

Met Glu Leu Arg Ser Leu Thr Ser Glu Asp Ser Val Tyr Tyr Cys
                85                  90                  95

Glu Ser Gln Ser Gly Ala Tyr Trp Gly Gln Gly Thr Thr Val Thr Val
            100                 105                 110

Ser Ala

<210> SEQ ID NO 48
<211> LENGTH: 20

```
<212> TYPE: PRT
<213> ORGANISM: Artificial Sequence
<220> FEATURE:
<223> OTHER INFORMATION: Synthetic Peptide

<400> SEQUENCE: 48

Gly Gly Gly Gly Ser Gly Gly Gly Ser Gly Gly Gly Ser Gly
1               5                   10                  15

Gly Gly Gly Ser
            20

<210> SEQ ID NO 49
<211> LENGTH: 116
<212> TYPE: PRT
<213> ORGANISM: Artificial Sequence
<220> FEATURE:
<223> OTHER INFORMATION: Synthetic Peptide

<400> SEQUENCE: 49

Asp Tyr Lys Asp Ile Leu Met Thr Gln Thr Pro Ser Ser Leu Pro Val
1               5                   10                  15

Ser Leu Gly Asp Gln Ala Ser Ile Ser Cys Arg Ser Ser Gln Ser Ile
            20                  25                  30

Val His Ser Asn Gly Asn Thr Tyr Leu Glu Trp Tyr Leu Gln Lys Pro
        35                  40                  45

Gly Gln Ser Pro Lys Leu Leu Ile Tyr Lys Val Ser Asn Arg Phe Ser
    50                  55                  60

Gly Val Pro Asp Arg Phe Ser Gly Ser Gly Ser Gly Thr Asp Phe Thr
65                  70                  75                  80

Leu Lys Ile Ser Arg Val Glu Ala Glu Asp Leu Gly Val Tyr Tyr Cys
                85                  90                  95

Phe Gln Gly Ser His Val Pro Phe Thr Phe Gly Ser Gly Thr Lys Leu
            100                 105                 110

Glu Ile Lys Arg
        115

<210> SEQ ID NO 50
<211> LENGTH: 291
<212> TYPE: PRT
<213> ORGANISM: Thermus thermophilus

<400> SEQUENCE: 50

Met Glu Ala Met Leu Pro Leu Phe Glu Pro Lys Gly Arg Val Leu Leu
1               5                   10                  15

Val Asp Gly His His Leu Ala Tyr Arg Thr Phe Phe Ala Leu Lys Gly
            20                  25                  30

Leu Thr Thr Ser Arg Gly Glu Pro Val Gln Ala Val Tyr Gly Phe Ala
        35                  40                  45

Lys Ser Leu Leu Lys Ala Leu Lys Glu Asp Gly Tyr Lys Ala Val Phe
    50                  55                  60

Val Val Phe Asp Ala Lys Ala Pro Ser Phe Arg His Glu Ala Tyr Glu
65                  70                  75                  80

Ala Tyr Lys Ala Gly Arg Ala Pro Thr Pro Glu Asp Phe Pro Arg Gln
                85                  90                  95

Leu Ala Leu Ile Lys Glu Leu Val Asp Leu Leu Gly Phe Thr Arg Leu
            100                 105                 110

Glu Val Pro Gly Tyr Glu Ala Asp Asp Val Leu Ala Thr Leu Ala Lys
        115                 120                 125
```

```
Lys Ala Glu Lys Glu Gly Tyr Glu Val Arg Ile Leu Thr Ala Asp Arg
    130                 135                 140

Asp Leu Tyr Gln Leu Val Ser Asp Arg Val Ala Val Leu His Pro Glu
145                 150                 155                 160

Gly His Leu Ile Thr Pro Glu Trp Leu Trp Glu Lys Tyr Gly Leu Arg
                165                 170                 175

Pro Glu Gln Trp Val Asp Phe Arg Ala Leu Val Gly Asp Pro Ser Asp
            180                 185                 190

Asn Leu Pro Gly Val Lys Gly Ile Gly Glu Lys Thr Ala Leu Lys Leu
        195                 200                 205

Leu Lys Glu Trp Gly Ser Leu Glu Asn Leu Leu Lys Asn Leu Asp Arg
    210                 215                 220

Val Lys Pro Glu Asn Val Arg Glu Lys Ile Lys Ala His Leu Glu Asp
225                 230                 235                 240

Leu Arg Leu Ser Leu Glu Leu Ser Arg Val Arg Thr Asp Leu Pro Leu
                245                 250                 255

Glu Val Asp Leu Ala Gln Gly Arg Glu Pro Asp Arg Glu Gly Leu Arg
            260                 265                 270

Ala Phe Leu Glu Arg Leu Glu Phe Gly Ser Leu Leu His Glu Phe Gly
        275                 280                 285

Leu Leu Glu
    290

<210> SEQ ID NO 51
<211> LENGTH: 196
<212> TYPE: PRT
<213> ORGANISM: Escherichia coli

<400> SEQUENCE: 51

Val Ile Ser Tyr Asp Asn Tyr Val Thr Ile Leu Asp Glu Glu Thr Leu
1               5                   10                  15

Lys Ala Trp Ile Ala Lys Leu Glu Lys Ala Pro Val Phe Ala Phe Asp
            20                  25                  30

Thr Glu Thr Asp Ser Leu Asp Asn Ile Ser Ala Asn Leu Val Gly Leu
        35                  40                  45

Ser Phe Ala Ile Glu Pro Gly Val Ala Ala Tyr Ile Pro Val Ala His
    50                  55                  60

Asp Tyr Leu Asp Ala Pro Asp Gln Ile Ser Arg Glu Arg Ala Leu Glu
65                  70                  75                  80

Leu Leu Lys Pro Leu Leu Glu Asp Glu Lys Ala Leu Lys Val Gly Gln
                85                  90                  95

Asn Leu Lys Tyr Asp Arg Gly Ile Leu Ala Asn Tyr Gly Ile Glu Leu
                100                 105                 110

Arg Gly Ile Ala Phe Asp Thr Met Leu Glu Ser Tyr Ile Leu Asn Ser
            115                 120                 125

Val Ala Gly Arg His Asp Met Asp Ser Leu Ala Glu Arg Trp Leu Lys
    130                 135                 140

His Lys Thr Ile Thr Phe Glu Glu Ile Ala Gly Lys Gly Lys Asn Gln
145                 150                 155                 160

Leu Thr Phe Asn Gln Ile Ala Leu Glu Glu Ala Gly Arg Tyr Ala Ala
                165                 170                 175

Glu Asp Ala Asp Val Thr Leu Gln Leu His Leu Lys Met Trp Pro Asp
            180                 185                 190

Leu Gln Lys His
    195
```

```
<210> SEQ ID NO 52
<211> LENGTH: 686
<212> TYPE: PRT
<213> ORGANISM: Bacillus circulans

<400> SEQUENCE: 52

Ala Pro Asp Thr Ser Val Ser Asn Lys Gln Asn Phe Ser Thr Asp Val
1               5                   10                  15

Ile Tyr Gln Ile Phe Thr Asp Arg Phe Ser Asp Gly Asn Pro Ala Asn
            20                  25                  30

Asn Pro Thr Gly Ala Ala Phe Asp Gly Thr Cys Thr Asn Leu Arg Leu
        35                  40                  45

Tyr Cys Gly Gly Asp Trp Gln Gly Ile Ile Asn Lys Ile Asn Asp Gly
    50                  55                  60

Tyr Leu Thr Gly Met Gly Val Thr Ala Ile Trp Ile Ser Gln Pro Val
65                  70                  75                  80

Glu Asn Ile Tyr Ser Ile Ile Asn Tyr Ser Gly Val Asn Asn Thr Ala
                85                  90                  95

Tyr His Gly Tyr Trp Ala Arg Asp Phe Lys Lys Thr Asn Pro Ala Tyr
            100                 105                 110

Gly Thr Ile Ala Asp Phe Gln Asn Leu Ile Ala Ala His Ala Lys
        115                 120                 125

Asn Ile Lys Val Ile Ile Asp Phe Ala Pro Asn His Thr Ser Pro Ala
    130                 135                 140

Ser Ser Asp Gln Pro Ser Phe Ala Glu Asn Gly Arg Leu Tyr Asp Asn
145                 150                 155                 160

Gly Thr Leu Leu Gly Gly Tyr Thr Asn Asp Thr Gln Asn Leu Phe His
                165                 170                 175

His Asn Gly Gly Thr Asp Phe Ser Thr Thr Glu Asn Gly Ile Tyr Lys
            180                 185                 190

Asn Leu Tyr Asp Leu Ala Asp Leu Asn His Asn Asn Ser Thr Val Asp
        195                 200                 205

Val Tyr Leu Lys Asp Ala Ile Lys Met Trp Leu Asp Leu Gly Ile Asp
    210                 215                 220

Gly Ile Arg Met Asp Ala Val Lys His Met Pro Phe Gly Trp Gln Lys
225                 230                 235                 240

Ser Phe Met Ala Ala Val Asn Asn Tyr Lys Pro Val Phe Thr Phe Gly
                245                 250                 255

Glu Trp Phe Leu Gly Val Asn Glu Val Ser Pro Glu Asn His Lys Phe
            260                 265                 270

Ala Asn Glu Ser Gly Met Ser Leu Leu Asp Phe Arg Phe Ala Gln Lys
        275                 280                 285

Val Arg Gln Val Phe Arg Asp Asn Thr Asp Asn Met Tyr Gly Leu Lys
    290                 295                 300

Ala Met Leu Glu Gly Ser Ala Ala Asp Tyr Ala Gln Val Asp Asp Gln
305                 310                 315                 320

Val Thr Phe Ile Asp Asn His Asp Met Glu Arg Phe His Ala Ser Asn
                325                 330                 335

Ala Asn Arg Arg Lys Leu Glu Gln Ala Leu Ala Phe Thr Leu Thr Ser
            340                 345                 350

Arg Gly Val Pro Ala Ile Tyr Tyr Gly Thr Glu Gln Tyr Met Ser Gly
        355                 360                 365

Gly Thr Asp Pro Asp Asn Arg Ala Arg Ile Pro Ser Phe Ser Thr Ser
```

```
                370             375             380
Thr Thr Ala Tyr Gln Val Ile Gln Lys Leu Ala Pro Leu Arg Lys Cys
385                 390                 395                 400

Asn Pro Ala Ile Ala Tyr Gly Ser Thr Gln Glu Arg Trp Ile Asn Asn
                405                 410                 415

Asp Val Leu Ile Tyr Glu Arg Lys Phe Gly Ser Asn Val Ala Val Val
            420                 425                 430

Ala Val Asn Arg Asn Leu Asn Ala Pro Ala Ser Ile Ser Gly Leu Val
        435                 440                 445

Thr Ser Leu Pro Gln Gly Ser Tyr Asn Asp Val Leu Gly Gly Leu Leu
    450                 455                 460

Asn Gly Asn Thr Leu Ser Val Gly Ser Gly Ala Ala Ser Asn Phe
465                 470                 475                 480

Thr Leu Ala Ala Gly Gly Thr Ala Val Trp Gln Tyr Thr Ala Ala Thr
                485                 490                 495

Ala Thr Pro Thr Ile Gly His Val Gly Pro Met Met Ala Lys Pro Gly
                500                 505                 510

Val Thr Ile Thr Ile Asp Gly Arg Gly Phe Gly Ser Ser Lys Gly Thr
            515                 520                 525

Val Tyr Phe Gly Thr Thr Ala Val Ser Gly Ala Asp Ile Thr Ser Trp
        530                 535                 540

Glu Asp Thr Gln Ile Lys Val Lys Ile Pro Ala Val Ala Gly Gly Asn
545                 550                 555                 560

Tyr Asn Ile Lys Val Ala Asn Ala Ala Gly Thr Ala Ser Asn Val Tyr
                565                 570                 575

Asp Asn Phe Glu Val Leu Ser Gly Asp Gln Val Ser Val Arg Phe Val
            580                 585                 590

Val Asn Asn Ala Thr Thr Ala Leu Gly Gln Asn Val Tyr Leu Thr Gly
        595                 600                 605

Ser Val Ser Glu Leu Gly Asn Trp Asp Pro Ala Lys Ala Ile Gly Pro
    610                 615                 620

Met Tyr Asn Gln Val Val Tyr Gln Tyr Pro Asn Trp Tyr Tyr Asp Val
625                 630                 635                 640

Ser Val Pro Ala Gly Lys Thr Ile Glu Phe Lys Phe Leu Lys Lys Gln
                645                 650                 655

Gly Ser Thr Val Thr Trp Glu Gly Gly Ser Asn His Thr Phe Thr Ala
            660                 665                 670

Pro Ser Ser Gly Thr Ala Thr Ile Asn Val Asn Trp Gln Pro
        675                 680                 685

<210> SEQ ID NO 53
<211> LENGTH: 399
<212> TYPE: PRT
<213> ORGANISM: Bordetella pertussis

<400> SEQUENCE: 53

Met Gln Gln Ser His Gln Ala Gly Tyr Ala Asn Ala Ala Asp Arg Glu
1               5                   10                  15

Ser Gly Ile Pro Ala Ala Val Leu Asp Gly Ile Lys Ala Val Ala Lys
                20                  25                  30

Glu Lys Asn Ala Thr Leu Met Phe Arg Leu Val Asn Pro His Ser Thr
            35                  40                  45

Ser Leu Ile Ala Glu Gly Val Ala Thr Lys Gly Leu Gly Val His Ala
        50                  55                  60
```

-continued

Lys Ser Ser Asp Trp Gly Leu Gln Ala Gly Tyr Ile Pro Val Asn Pro
65                  70                  75                  80

Asn Leu Ser Lys Leu Phe Gly Arg Ala Pro Glu Val Ile Ala Arg Ala
                85                  90                  95

Asp Asn Asp Val Asn Ser Ser Leu Ala His Gly His Thr Ala Val Asp
            100                 105                 110

Leu Thr Leu Ser Lys Glu Arg Leu Asp Tyr Leu Arg Gln Ala Gly Leu
        115                 120                 125

Val Thr Gly Met Ala Asp Gly Val Ala Ser Asn His Ala Gly Tyr
    130                 135                 140

Glu Gln Phe Glu Phe Arg Val Lys Glu Thr Ser Asp Gly Arg Tyr Ala
145                 150                 155                 160

Val Gln Tyr Arg Arg Lys Gly Gly Asp Asp Phe Glu Ala Val Lys Val
                165                 170                 175

Ile Gly Asn Ala Ala Gly Ile Pro Leu Thr Ala Asp Ile Asp Met Phe
            180                 185                 190

Ala Ile Met Pro His Leu Ser Asn Phe Arg Asp Ser Ala Arg Ser Ser
        195                 200                 205

Val Thr Ser Gly Asp Ser Val Thr Asp Tyr Leu Ala Arg Thr Arg Arg
    210                 215                 220

Ala Ala Ser Glu Ala Thr Gly Gly Leu Asp Arg Glu Arg Ile Asp Leu
225                 230                 235                 240

Leu Trp Lys Ile Ala Arg Ala Gly Ala Arg Ser Ala Val Gly Thr Glu
                245                 250                 255

Ala Arg Arg Gln Phe Arg Tyr Asp Gly Asp Met Asn Ile Gly Val Ile
            260                 265                 270

Thr Asp Phe Glu Leu Glu Val Arg Asn Ala Leu Asn Arg Arg Ala His
        275                 280                 285

Ala Val Gly Ala Gln Asp Val Val Gln His Gly Thr Glu Gln Asn Asn
    290                 295                 300

Pro Phe Pro Glu Ala Asp Glu Lys Ile Phe Val Val Ser Ala Thr Gly
305                 310                 315                 320

Glu Ser Gln Met Leu Thr Arg Gly Gln Leu Lys Glu Tyr Ile Gly Gln
                325                 330                 335

Gln Arg Gly Glu Gly Tyr Val Phe Tyr Glu Asn Arg Ala Tyr Gly Val
            340                 345                 350

Ala Gly Lys Ser Leu Phe Asp Asp Gly Leu Gly Ala Ala Pro Gly Val
        355                 360                 365

Pro Ser Gly Arg Ser Lys Phe Ser Pro Asp Val Leu Glu Thr Val Pro
    370                 375                 380

Ala Ser Pro Gly Leu Arg Arg Pro Ser Leu Gly Ala Val Glu Arg
385                 390                 395

<210> SEQ ID NO 54
<211> LENGTH: 275
<212> TYPE: PRT
<213> ORGANISM: Bacillus amyloliquefaciens

<400> SEQUENCE: 54

Ala Gln Ser Val Pro Tyr Gly Val Ser Gln Ile Lys Ala Pro Ala Leu
1               5                   10                  15

His Ser Gln Gly Tyr Thr Gly Ser Asn Val Lys Val Ala Val Ile Asp
            20                  25                  30

Ser Gly Ile Asp Ser Ser His Pro Asp Leu Lys Val Ala Gly Gly Ala
        35                  40                  45

```
Ser Met Val Pro Ser Glu Thr Asn Pro Phe Gln Asp Asn Asn Ser His
    50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
            100                 105                 110

Trp Ala Ile Ala Asn Asn Met Asp Val Ile Asn Met Ser Leu Gly Gly
        115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
            180                 185                 190

Gly Pro Glu Leu Asp Val Met Ala Pro Gly Val Ser Ile Gln Ser Thr
        195                 200                 205

Leu Pro Gly Asn Lys Tyr Gly Ala Tyr Asn Gly Thr Ser Met Ala Ser
210                 215                 220

Pro His Val Ala Gly Ala Ala Ala Leu Ile Leu Ser Lys His Pro Asn
225                 230                 235                 240

Trp Thr Asn Thr Gln Val Arg Ser Ser Leu Glu Asn Thr Thr Thr Lys
                245                 250                 255

Leu Gly Asp Ser Phe Tyr Tyr Gly Lys Gly Leu Ile Asn Val Gln Ala
            260                 265                 270

Ala Ala Gln
        275

<210> SEQ ID NO 55
<211> LENGTH: 182
<212> TYPE: PRT
<213> ORGANISM: Bacillus subtilis

<400> SEQUENCE: 55

Ala Ala Glu His Asn Pro Val Val Met Val His Gly Ile Gly Gly Ala
1               5                   10                  15

Ser Phe Asn Phe Ala Gly Ile Lys Ser Tyr Leu Val Ser Gln Gly Trp
                20                  25                  30

Ser Arg Asp Lys Leu Tyr Ala Val Asp Phe Trp Asp Lys Thr Gly Thr
            35                  40                  45

Asn Tyr Asn Asn Gly Pro Val Leu Ser Arg Phe Val Gln Lys Val Leu
        50                  55                  60

Asp Glu Thr Gly Ala Lys Lys Val Asp Ile Val Ala His Ser Met Gly
65                  70                  75                  80

Gly Ala Asn Thr Leu Tyr Tyr Ile Lys Asn Leu Asp Gly Gly Asn Lys
                85                  90                  95

Val Ala Asn Val Val Thr Leu Gly Gly Ala Asn Arg Leu Thr Thr Gly
            100                 105                 110

Lys Ala Leu Pro Gly Thr Asp Pro Asn Gln Lys Ile Leu Tyr Thr Ser
        115                 120                 125

Ile Tyr Ser Ser Ala Asp Met Ile Val Met Asn Tyr Leu Ser Arg Leu
```

```
                130               135               140
Asp Gly Ala Arg Asn Val Gln Ile His Gly Val Gly His Ile Gly Leu
145                 150                 155                 160

Leu Tyr Ser Ser Gln Val Asn Ser Leu Ile Lys Glu Gly Leu Asn Gly
                165                 170                 175

Gly Gly Gln Asn Thr Asn
            180

<210> SEQ ID NO 56
<211> LENGTH: 444
<212> TYPE: DNA
<213> ORGANISM: Homo sapiens

<400> SEQUENCE: 56
gctgaccaac tgactgaaga gcagattgca gaattcaaag aagcttttc actatttgac      60 aaagatggtg atggaactat aacaacaaag gaattgggaa ctgtaatgag atctcttggg    120
cagaatccca cagaagcaga gttacaggac atgattaatg aagtagatgc tgatggtaat    180
ggcacaattg acttccctga atttctgaca atgatggcaa gaaaaatgaa agacacagac    240
agtgaagaag aaattagaga agcattccgt gtgtttgata aggatggcaa tggctatatt    300
agtgctgcag aacttcgcca tgtgatgaca aaccttggag agaagttaac agatgaagaa    360
gttgatgaaa tgatcaggga agcagatatt gatggtgatg gtcaagtaaa ctatgaagag    420
tttgtacaaa tgatgacagc aaag                                           444

<210> SEQ ID NO 57
<211> LENGTH: 2058
<212> TYPE: DNA
<213> ORGANISM: Bacillus circulans

<400> SEQUENCE: 57
gcgccggata cctcggtatc caacaagcaa aatttcagca ccgacgtcat ctatcaaatt      60
ttcaccgaca ggttttcgga cggcaatccc gccaacaatc cgaccggcgc ggcgtttgac    120
ggaacctgca cgaacctccg gctgtattgc ggcggcgact gcagggcat catcaacaaa     180 atcaacgacg gttacctgac cgggatgggc gttaccgcca tctggatctc ccagccggtc    240
gaaaacatct acagcatcat caattattcc ggcgtaaaca cacgggccta tcacggctac    300
tgggcccggg acttcaagaa gacgaatccg gcctacggca cgattgcgga cttccagaac    360
ctgatcgccg ccgcgcatgc aaaaaacatc aaagtcatta tcgactttgc cccgaaccat    420
acgtcgcccg cctcgtccga ccagccttcc tttgcggaaa acggccggct gtacgataac    480
ggcacgctgc tcgggggata cacgaacgat acgcagaacc tgttccacca taacggcggc    540
acggactttt ccacgaccga aaacggcatc tacaaaaacc tgtacgatct cgccgacctg    600
aaccataaca cacagcaccgt ggacgtctac ttgaaggacg cgatcaaaat gtggctggac    660
ctcggcatcg acggcatccg catggatgcg gtgaagcata tgccgttcgg ctggcagaag    720
agctttatgg ctgccgtcaa caactataag ccggtcttta ccttcggcga atggttcctg    780
ggcgtaaatg aagtgagccc ggaaaaccat aagtttgcca acgaatccgg catgagcctg    840
cttgatttcc gttttgccca aaaggtgcgg caggtgttcc gggacaacac cgacaatatg    900
tacgccctga aggcgatgct ggagggctcc gcagccgatt acgcccaggt ggatgaccag    960
gtgacgttca tcgacaacca tgacatggag cgtttccacg caagcaatgc aaaccgccgc   1020
aagctggagc aagcgcttgc gttcacgctg acctcgcgcg gcgtcccgc catttattac   1080
```

```
ggcaccgagc agtacatgtc gggcgggacc gatccggaca accgggcgcg gatcccttcc    1140
ttctccacgt cgacgaccgc ctatcaggtc attcaaaagc tggcgccgct gcgcaagtgc    1200
aacccggcca tcgcctacgg atcgacgcag gagcgctgga tcaacaacga cgtgctcatt    1260
tatgagcgca aattcggcag caacgttgcc gtcgttgccg tcaaccgcaa tttaaacgcg    1320
ccggcttcca tttcgggact tgtcacttcc ctgccgcaag gcagctacaa cgacgtcctt    1380
ggcggccttc tgaacggcaa cacgttatcg gtaggctccg gcggggccgc ctccaatttc    1440
acgcttgcgg ccggcggcac ggcggtgtgg cagtacaccg cggctacggc gacgccgacc    1500
atcgggcatg tcgggccgat gatggccaag ccgggcgtga cgatcacgat cgacggccgc    1560
ggcttcggct ctagcaaagg caccgtctac ttcggtacga cggcggtgag cggggcggac    1620
atcacgtctt gggaagacac gcagatcaaa gtgaaaattc cggccgtcgc aggcggcaac    1680
tacaacatta agtcgcaaa cgctgccgga acggcaagca atgtgtatga caacttcgag    1740
gtattgtccg gagaccaggt cagcgtccgc ttcgtggtca acaacgcgac gacggccctt    1800
gggcaaaatg tgtacctgac gggcagtgtc agcgagctgg ggaactggga cccggcaaaa    1860
gcaatcgggc cgatgtacaa tcaggtcgtt taccaatatc cgaactggta ttatgacgtc    1920
agcgttccgg ccggcaaaac gatcgagttc aagttttga aaaaacaagg ctccaccgtc    1980
acgtgggaag cggcagcaa ccacaccttc accgcgccgt ccagcggcac cgcgaccatt    2040
aacgtgaatt ggcagcca                                                  2058

<210> SEQ ID NO 58
<211> LENGTH: 1197
<212> TYPE: DNA
<213> ORGANISM: Bordetella pertussis

<400> SEQUENCE: 58
atgcagcaat cgcatcaggc tggttacgca aacgccgccg accgggagtc tggcatcccc      60
gcagccgtac tcgatggcat caaggccgtg gcgaaggaaa aaacgccac attgatgttc      120 cgcctggtca accccattc caccagcctg attgccgaag gggtggccac caaaggattg      180
ggcgtgcacg ccaagtcgtc cgattggggg ttgcaggcgg gctacattcc cgtcaacccg      240
aatctttcca aactgttcgg ccgtgcgccc gaggtgatcg cgcgggccga caacgacgtc      300
aacagcagcc tggcgcatgg ccataccgcg gtcgacctga cgctgtcgaa agagcggctt      360
gactatctgc ggcaagcggg cctggtcacc ggcatggccg atggcgtggt cgcgagcaac      420
cacgcaggct acgagcagtt cgagtttcgc gtgaaggaaa cctcggacgg cgcgctatgcc      480 gtgcagtatc gccgcaaggg cggcgacgat ttcgaggcgg tcaaggtgat cggcaatgcc      540
gccggtattc cactgacggc ggatatcgac atgttcgcca ttatgccgca tctgtccaac      600
ttccgcgact cggcgcgcag ttcggtgacc agcggcgatt cggtgaccga ttacctggcg      660
cgcacgcggc gggccgccag cgaggccacg gcggcctgg atcgcgaacg catcgacttg      720
ttgtggaaaa tcgctcgcgc cggcgcccgt tccgcagtgg caccgaggc gcgtcgccag      780 ttccgctacg acggcgacat gaatatcggc gtgatcaccg atttcgagct ggaagtgcgc      840
aatgcgctga acaggcgggc gcacgccgtc ggcgcgcagg acgtggtcca gcatggcact      900
gagcagaaca atccttcccc ggaggcagat gagaagattt cgtcgtatc ggccaccggt      960 gaaagccaga tgctcacgcg cgggcaactg aaggaataca ttggccagca gcgcggcgag     1020
ggctatgtct ctctacgagaa ccgtgcatac ggcgtggcgg ggaaaagcct gttcgacgat     1080
gggctgggag ccgcgcccgg cgtgccgagc ggacgttcga agttctcgcc ggatgtactg     1140
```

```
gaaacggtgc cggcgtcacc cggattgcgg cggccgtcgc tgggcgcagt ggaacgc      1197

<210> SEQ ID NO 59
<211> LENGTH: 825
<212> TYPE: DNA
<213> ORGANISM: Bacillus amyloliquefaciens

<400> SEQUENCE: 59
gcgcagtccg tgccttacgg cgtatcacaa attaaagccc ctgctctgca ctctcaaggc     60
tacactggat caaatgttaa agtagcggtt atcgacagcg gtatcgattc ttctcatcct    120
gatttaaagg tagcaggcgg agccagcatg gttccttctg aaacaaatcc tttccaagac    180
aacaactctc acggaactca cgttgccggc acagttgcgg ctcttaataa ctcaatcggt    240
gtattaggcg ttgcgccaag cgcatcactt tacgctgtaa aagttctcgg tgctgacggt    300
tccggccaat acagctggat cattaacgga atcgagtggg cgatcgcaaa caatatggac    360
gttattaaca tgagcctcgg cggaccttct ggttctgctg ctttaaaagc ggcagttgat    420
aaagccgttg catccggcgt cgtagtcgtt gcggcagccg taacgaagg cacttccggc     480 agctcaagca cagtgggcta ccctggtaaa taccttctg tcattgcagt aggcgctgtt     540
gacagcagca accaaagagc atctttctca agcgtaggac ctgagcttga tgtcatggca    600
cctggcgtat ctatccaaag cacgcttcct ggaaacaaat acggggcgta caacggtacg    660
tcaatggcat ctccgcacgt tgccggagcg gctgctttga ttctttctaa gcacccgaac    720
tggacaaaca ctcaagtccg cagcagttta gaaaacacca ctacaaaact tggtgattct    780
ttctactatg aaaagggct gatcaacgta caggcggcag ctcag                    825

<210> SEQ ID NO 60
<211> LENGTH: 873
<212> TYPE: DNA
<213> ORGANISM: Thermus thermophilus

<400> SEQUENCE: 60
atggaggcga tgcttccgct ctttgaaccc aaaggccggg tcctcctggt ggacggccac     60
cacctggcct accgcacctt cttcgccctg aagggcctca ccacgagccg ggcgaaccg    120 gtgcaggcgg tctacggctt cgccaagagc ctcctcaagg ccctgaagga ggacgggtac    180
aaggccgtct tcgtggtctt tgacgccaag gcccctcct tccgccacga ggcctacgag    240
gcctacaagg cggggagggc cccgacccc gaggacttcc ccggcagct cgccctcatc    300 aaggagctgg tggacctcct ggggtttacc cgcctcgagg tccccggcta cgaggcggac    360
gacgttctcg ccaccctggc caagaaggcg aaaaggagg ggtacgaggt gcgcatcctc    420
accgccgacc gcgacctcta ccaactcgtc tccgaccgcg tcgccgtcct ccaccccgag    480
ggccacctca tcaccccgga gtggctttgg gagaagtacg gcctcaggcc ggagcagtgg    540
gtggacttcc gcgccctcgt gggggacccc tccgacaacc tccccgggt caagggcatc    600 ggggagaaga ccgccctcaa gctcctcaag gagtggggaa gctggaaaa cctcctcaag    660 aacctggacc gggtaaagcc agaaaacgtc cgggagaaga tcaaggccca cctggaagac    720
ctcaggctct ccttggagct ctcccggtgt cgcaccgacc tccccctgga ggtggacctc    780 gcccagggc gggagcccga ccgggagggg cttagggcct cctggagag gctggagttc    840 ggcagcctcc tccacgagtt cggcctcctg gag                               873

<210> SEQ ID NO 61
```

```
<211> LENGTH: 588
<212> TYPE: DNA
<213> ORGANISM: Escherichia coli

<400> SEQUENCE: 61
gtgatttctt atgacaacta cgtcaccatc cttgatgaag aaacactgaa agcgtggatt        60
gcgaagctgg aaaaagcgcc ggtatttgca tttgataccg aaaccgacag ccttgataac       120
atctctgcta acctggtcgg gctttctttt gctatcgagc caggcgtagc ggcatatatt       180
ccggttgctc atgattatct tgatgcgccc gatcaaatct ctcgcgagcg tgcactcgag       240
ttgctaaaac cgctgctgga agatgaaaag gcgctgaagg tcgggcaaaa cctgaaatac       300
gatcgcggta ttctggcgaa ctacggcatt gaactgcgtg ggattgcgtt tgataccatg       360
ctggagtcct acattctcaa tagcgttgcc gggcgtcacg atatggacag cctcgcggaa       420
cgttggttga agcacaaaac catcactttt gaagagattg ctggtaaagg caaaaatcaa       480
ctgaccttta accagattgc cctcgaagaa gccggacgtt acgccgccga agatgcagat       540
gtcaccttgc agttgcatct gaaaatgtgg ccggatctgc aaaaacac                    588
```